US008597360B2

(12) United States Patent
McLuen et al.

(10) Patent No.: US 8,597,360 B2
(45) Date of Patent: Dec. 3, 2013

(54) BONE FUSION DEVICE

(75) Inventors: Gary R. McLuen, Port Townsend, WA (US); Benjamin J. Remington, Modesto, CA (US); Daniel R. Baker, Seattle, WA (US); Joseph N. Logan, Trumbull, CT (US); Gregory C. Stalcup, Columbia City, IN (US)

(73) Assignee: Neuropro Technologies, Inc., Modesto, CA (US)

( * ) Notice: Subject to any disclaimer, the term of this patent is extended or adjusted under 35 U.S.C. 154(b) by 0 days.

(21) Appl. No.: 13/482,778

(22) Filed: May 29, 2012

(65) Prior Publication Data

US 2012/0303124 A1 Nov. 29, 2012

Related U.S. Application Data

(63) Continuation-in-part of application No. 11/484,379, filed on Jul. 10, 2006, now Pat. No. 8,187,332, which is a continuation-in-part of application No. 11/357,319, filed on Feb. 16, 2006, now Pat. No. 7,727,280, which is a continuation-in-part of application No. 11/264,958, filed on Nov. 1, 2005, now abandoned.

(60) Provisional application No. 60/624,836, filed on Nov. 3, 2004, provisional application No. 61/624,155, filed on Apr. 13, 2012.

(51) Int. Cl.
*A61F 2/44* (2006.01)
(52) U.S. Cl.
USPC ..................................................... 623/17.16
(58) Field of Classification Search
USPC ......... 623/17.11–17.16; 606/60, 246–249, 99
See application file for complete search history.

(56) References Cited

U.S. PATENT DOCUMENTS

| 4,767,040 A | | 8/1988 | Miller et al. | |
|---|---|---|---|---|
| 4,863,476 A | * | 9/1989 | Shepperd | 623/17.15 |
| 4,961,740 A | * | 10/1990 | Ray et al. | 606/247 |
| 5,015,247 A | * | 5/1991 | Michelson | 606/247 |
| 5,059,193 A | * | 10/1991 | Kuslich | 606/247 |
| 5,443,514 A | * | 8/1995 | Steffee | 128/898 |
| 5,522,899 A | * | 6/1996 | Michelson | 606/279 |
| 5,653,763 A | * | 8/1997 | Errico et al. | 623/17.11 |

(Continued)

FOREIGN PATENT DOCUMENTS

| JP | 2274243 | 11/1990 |
|---|---|---|
| WO | WO9117723 | 11/1991 |

(Continued)

*Primary Examiner* — Alvin J. Stewart
(74) *Attorney, Agent, or Firm* — Haverstock & Owens LLP

(57) ABSTRACT

A bone fusion device provides stability to bones during a bone fusion period. The bones include, for example, the vertebrae of a spinal column. The bone fusion device comprises one or more extendable tabs attached to the bone fusion device by associated rotating means. The bone fusion device is preferably inserted by using an arthroscopic surgical procedure. During arthroscopic insertion of the device, the tabs are pre-configured for compactness. In this compact configuration, the tabs are preferably deposed along and/or within an exterior surface of the bone fusion device. After the bone fusion device has been positioned between the bones, one or more tab(s) are extended. In the preferred embodiment, the position of each tab is related to a positioning element and extending blocks. Typically, the tabs advantageously position and brace the bone fusion device in the confined space between the bones until the bones have fused.

8 Claims, 32 Drawing Sheets

(56) References Cited

U.S. PATENT DOCUMENTS

| | | | |
|---|---|---|---|
| 5,658,335 A * | 8/1997 | Allen | 623/17.16 |
| 5,665,122 A * | 9/1997 | Kambin | 623/17.16 |
| 5,693,100 A * | 12/1997 | Pisharodi | 623/17.16 |
| 5,702,391 A * | 12/1997 | Lin | 623/17.11 |
| 5,716,415 A * | 2/1998 | Steffee | 623/17.16 |
| 5,800,547 A * | 9/1998 | Schafer et al. | 623/17.16 |
| 5,800,550 A * | 9/1998 | Sertich | 623/17.16 |
| 5,865,848 A * | 2/1999 | Baker | 623/17.15 |
| 5,885,287 A * | 3/1999 | Bagby | 623/16.11 |
| 5,980,522 A * | 11/1999 | Koros et al. | 623/17.11 |
| 6,045,579 A * | 4/2000 | Hochshuler et al. | 623/17.16 |
| 6,080,158 A * | 6/2000 | Lin | 606/247 |
| 6,080,193 A | 6/2000 | Hochshuler et al. | 623/17.16 |
| 6,102,949 A * | 8/2000 | Biedermann et al. | 623/17.16 |
| 6,102,950 A * | 8/2000 | Vaccaro | 623/17.16 |
| 6,117,174 A * | 9/2000 | Nolan | 623/17.11 |
| 6,129,763 A * | 10/2000 | Chauvin et al. | 623/17.11 |
| 6,156,067 A * | 12/2000 | Bryan et al. | 623/17.15 |
| 6,159,244 A * | 12/2000 | Suddaby | 623/17.11 |
| 6,174,334 B1* | 1/2001 | Suddaby | 623/17.11 |
| 6,176,882 B1* | 1/2001 | Biedermann et al. | 623/17.15 |
| 6,179,873 B1* | 1/2001 | Zientek | 623/17.11 |
| 6,183,517 B1* | 2/2001 | Suddaby | 623/17.16 |
| 6,190,414 B1* | 2/2001 | Young et al. | 623/17.15 |
| 6,325,827 B1 | 12/2001 | Lin | |
| 6,342,074 B1* | 1/2002 | Simpson | 623/17.11 |
| 6,371,968 B1* | 4/2002 | Kogasaka et al. | 606/190 |
| 6,371,987 B1* | 4/2002 | Weiland et al. | 623/17.11 |
| 6,375,655 B1* | 4/2002 | Zdeblick et al. | 623/17.16 |
| 6,375,683 B1* | 4/2002 | Crozet et al. | 623/17.15 |
| 6,409,766 B1* | 6/2002 | Brett | 623/17.16 |
| 6,419,705 B1* | 7/2002 | Erickson | 623/17.16 |
| 6,436,140 B1* | 8/2002 | Liu et al. | 623/17.11 |
| 6,443,989 B1* | 9/2002 | Jackson | 623/17.15 |
| 6,454,806 B1* | 9/2002 | Cohen et al. | 623/17.15 |
| 6,454,807 B1* | 9/2002 | Jackson | 623/17.15 |
| 6,464,727 B1* | 10/2002 | Sharkey et al. | 623/17.16 |
| 6,488,710 B2* | 12/2002 | Besselink | 623/17.15 |
| 6,491,695 B1* | 12/2002 | Roggenbuck | 606/86 A |
| 6,527,803 B1* | 3/2003 | Crozet et al. | 623/17.11 |
| 6,562,041 B1* | 5/2003 | Yonemura et al. | 606/279 |
| 6,572,619 B2* | 6/2003 | Santilli | 623/17.11 |
| 6,576,016 B1* | 6/2003 | Hochshuler et al. | 623/17.15 |
| 6,582,431 B1* | 6/2003 | Ray | 606/86 A |
| 6,582,467 B1* | 6/2003 | Teitelbaum et al. | 623/17.11 |
| 6,595,995 B2* | 7/2003 | Zdeblick et al. | 606/80 |
| 6,613,091 B1* | 9/2003 | Zdeblick et al. | 623/17.16 |
| 6,645,249 B2* | 11/2003 | Ralph et al. | 623/17.13 |
| 6,652,584 B2* | 11/2003 | Michelson | 623/17.11 |
| 6,666,888 B1* | 12/2003 | Jackson | 623/17.16 |
| 6,685,742 B1* | 2/2004 | Jackson | 623/17.11 |
| 6,706,070 B1 | 3/2004 | Wagner et al. | |
| 6,709,458 B2* | 3/2004 | Michelson | 623/17.15 |
| 6,723,128 B2* | 4/2004 | Uk | 623/17.15 |
| 6,746,454 B2* | 6/2004 | Winterbottom et al. | 606/99 |
| 6,767,367 B1* | 7/2004 | Michelson | 623/17.16 |
| 6,770,095 B2* | 8/2004 | Grinberg et al. | 623/17.14 |
| 6,770,096 B2* | 8/2004 | Bolger et al. | 623/17.16 |
| 6,821,298 B1* | 11/2004 | Jackson | 623/17.15 |
| 6,830,589 B2* | 12/2004 | Erickson | 623/17.15 |
| 6,835,206 B2* | 12/2004 | Jackson | 623/17.11 |
| 6,902,568 B2* | 6/2005 | Serhan | 606/79 |
| 6,923,830 B2* | 8/2005 | Michelson | 623/17.16 |
| 6,942,698 B1 | 9/2005 | Jackson | |
| 6,962,606 B2* | 11/2005 | Michelson | 623/17.16 |
| 6,989,011 B2* | 1/2006 | Paul et al. | 606/250 |
| 7,008,453 B1* | 3/2006 | Michelson | 623/17.16 |
| 7,018,415 B1* | 3/2006 | McKay | 623/17.15 |
| 7,094,257 B2* | 8/2006 | Mujwid et al. | 623/17.15 |
| 7,118,598 B2* | 10/2006 | Michelson | 623/17.11 |
| 7,128,760 B2* | 10/2006 | Michelson | 623/17.15 |
| 7,166,130 B2* | 1/2007 | Ferree | 623/17.15 |
| 7,195,643 B2 | 3/2007 | Jackson | |
| 7,217,291 B2* | 5/2007 | Zucherman et al. | 623/17.15 |
| 7,217,293 B2* | 5/2007 | Branch, Jr. | 623/17.16 |
| 7,220,282 B2 | 5/2007 | Kuslich | |
| 7,235,103 B2* | 6/2007 | Rivin | 623/17.13 |
| 7,238,186 B2* | 7/2007 | Zdeblick et al. | 623/17.16 |
| 7,323,011 B2 | 1/2008 | Shepard et al. | |
| 7,331,996 B2* | 2/2008 | Sato et al. | 623/17.16 |
| 7,445,636 B2* | 11/2008 | Michelson | 623/17.15 |
| 7,479,160 B2* | 1/2009 | Branch et al. | 623/17.11 |
| 7,537,612 B2* | 5/2009 | Kunzler | 623/17.13 |
| 7,588,573 B2 | 9/2009 | Berry | |
| 7,621,956 B2* | 11/2009 | Paul et al. | 623/17.15 |
| 7,674,296 B2* | 3/2010 | Rhoda et al. | 623/17.15 |
| 7,727,280 B2* | 6/2010 | McLuen | 623/17.16 |
| 7,758,617 B2* | 7/2010 | Iott et al. | 606/246 |
| D626,233 S * | 10/2010 | Cipoletti et al. | D24/155 |
| 7,811,327 B2* | 10/2010 | Hansell et al. | 623/17.15 |
| 7,837,688 B2* | 11/2010 | Boyer et al. | 606/86 A |
| 7,837,734 B2* | 11/2010 | Zucherman et al. | 623/17.15 |
| 8,002,834 B2* | 8/2011 | de Villiers et al. | 623/17.14 |
| 8,062,375 B2* | 11/2011 | Glerum et al. | 623/17.16 |
| 8,110,004 B2* | 2/2012 | Valdevit et al. | 623/17.16 |
| 8,187,332 B2* | 5/2012 | McLuen | 623/17.16 |
| 8,262,736 B2* | 9/2012 | Michelson | 623/17.16 |
| 8,303,658 B2* | 11/2012 | Peterman | 623/17.11 |
| 8,343,222 B2* | 1/2013 | Cope | 623/17.14 |
| 2004/0024461 A1* | 2/2004 | Ferree | 623/17.13 |
| 2004/0039448 A1* | 2/2004 | Pisharodi | 623/17.15 |
| 2004/0106998 A1* | 6/2004 | Ferree | 623/17.16 |
| 2004/0127993 A1* | 7/2004 | Kast et al. | 623/17.16 |
| 2004/0138750 A1* | 7/2004 | Mitchell | 623/17.11 |
| 2005/0015149 A1* | 1/2005 | Michelson | 623/17.11 |
| 2005/0278036 A1* | 12/2005 | Leonard et al. | 623/23.47 |
| 2005/0283236 A1* | 12/2005 | Razian | 623/17.11 |
| 2006/0069436 A1* | 3/2006 | Sutton et al. | 623/17.13 |
| 2006/0116769 A1* | 6/2006 | Marnay et al. | 623/17.15 |
| 2006/0241774 A1* | 10/2006 | Attali et al. | 623/17.16 |
| 2007/0093897 A1* | 4/2007 | Gerbec et al. | 623/17.11 |
| 2007/0270968 A1* | 11/2007 | Baynham et al. | 623/17.11 |
| 2008/0009880 A1* | 1/2008 | Warnick et al. | 606/99 |
| 2008/0015701 A1* | 1/2008 | Garcia et al. | 623/17.16 |
| 2008/0132949 A1* | 6/2008 | Aferzon et al. | 606/246 |
| 2008/0140207 A1* | 6/2008 | Olmos et al. | 623/17.16 |
| 2008/0183293 A1 | 7/2008 | Parry et al. | |
| 2008/0243125 A1 | 10/2008 | Guzman et al. | |
| 2008/0269905 A1* | 10/2008 | Link | 623/17.16 |
| 2008/0288076 A1* | 11/2008 | Soo et al. | 623/17.16 |
| 2008/0306489 A1 | 12/2008 | Altarac et al. | |
| 2009/0099601 A1* | 4/2009 | Aferzon et al. | 606/246 |
| 2009/0164020 A1* | 6/2009 | Janowski et al. | 623/17.16 |
| 2009/0222100 A1* | 9/2009 | Cipoletti et al. | 623/17.16 |
| 2009/0222101 A1* | 9/2009 | de Villiers et al. | 623/17.16 |
| 2010/0042219 A1 | 2/2010 | Antonacci et al. | |
| 2010/0256768 A1* | 10/2010 | Lim et al. | 623/17.16 |
| 2010/0298939 A1* | 11/2010 | Delfosse et al. | 623/17.16 |
| 2011/0172774 A1* | 7/2011 | Varela | 623/17.16 |
| 2011/0282453 A1* | 11/2011 | Greenhalgh et al. | 623/17.16 |

FOREIGN PATENT DOCUMENTS

| | | |
|---|---|---|
| WO | 2008035849 A1 | 3/2008 |
| WO | 2010045301 A1 | 4/2010 |
| WO | 2010121030 A2 | 10/2010 |

* cited by examiner

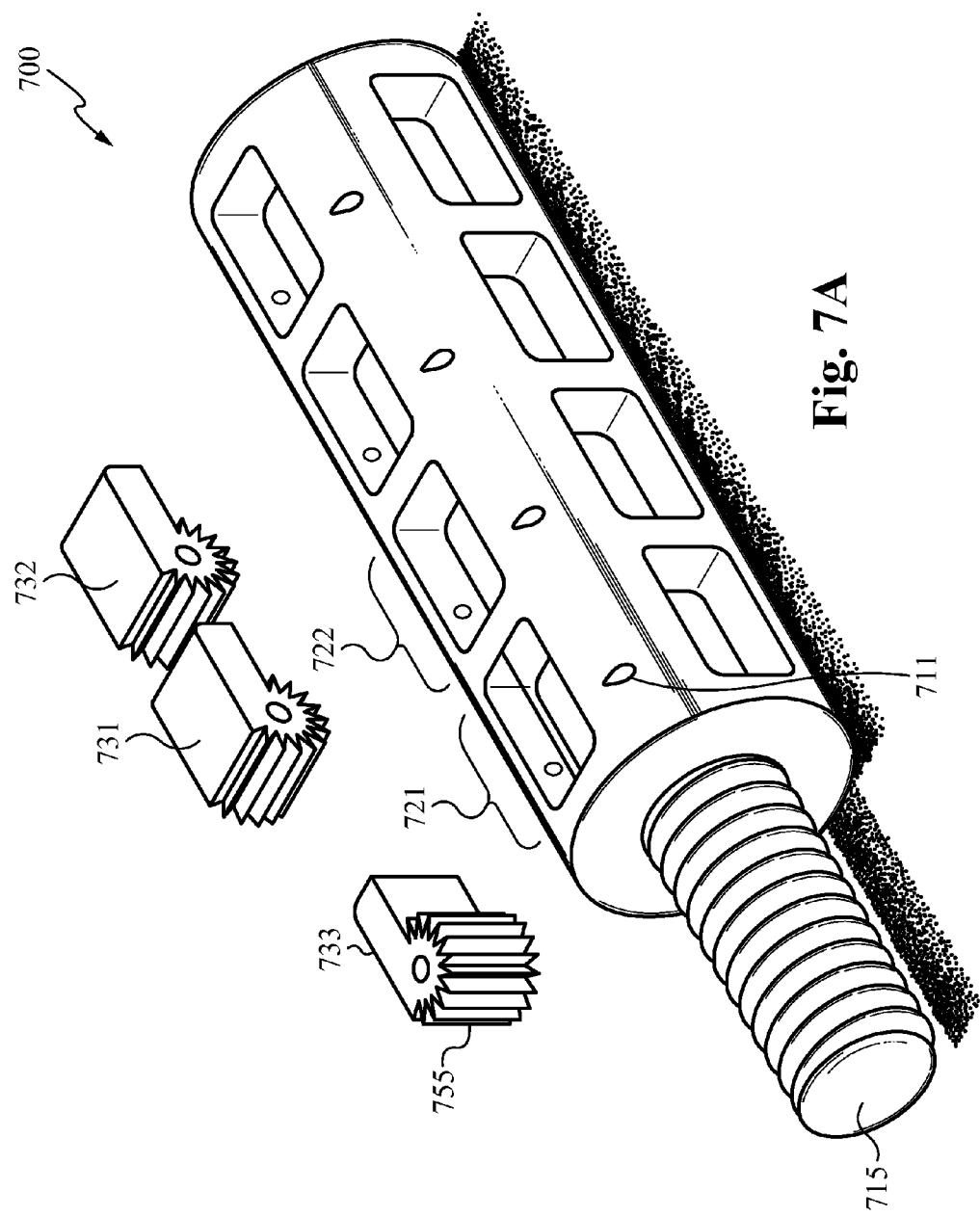

BONE FUSION DEVICE

RELATED APPLICATIONS

This application is a continuation-in-part of U.S. patent application Ser. No. 11/484,379, filed on Jul. 10, 2006 and entitled "BONE FUSION DEVICE," which is a continuation-in-part of U.S. Pat. No. 7,727,280, issued on Jun. 1, 2010 and entitled "BONE FUSION DEVICE," which is a continuation-in-part of abandoned U.S. patent application Ser. No. 11/264, 958, filed on Nov. 1, 2005 and entitled "BONE FUSION DEVICE," and which claims priority under 35 U.S.C. §119 (e) of the expired U.S. Provisional Patent Application Ser. No. 60/624,836, filed Nov. 3, 2004, and entitled "BONE FUSION DEVICE," all of which are hereby incorporated by reference. Additionally, this application claims priority under 35 U.S.C. §119(e) of U.S. Provisional Patent Application Ser. No. 61/624,155, filed Apr. 13, 2012, and entitled "BONE FUSION DEVICE," which is hereby incorporated by reference.

FIELD OF THE INVENTION

This invention relates generally to bone fusion devices. More specifically, the present invention relates to devices for fusing vertebrae of the spine that can be inserted arthroscopically.

BACKGROUND OF THE INVENTION

The spinal column is made up of vertebrae stacked on top of one another. Between the vertebrae are discs which are gel-like cushions that act as shock-absorbers and keep the spine flexible. Injury, disease, or excessive pressure on the discs can cause degenerative disc disease or other disorders where the disc becomes thinner and allows the vertebrae to move closer together or become misaligned. As a result, nerves may become pinched, causing pain that radiates into other parts of the body, or instability of the vertebrae may ensue.

One method for correcting disc-related disorders is to insert a fusion cage between the vertebrae to act as a structural replacement for the deteriorated disc. The fusion cage is typically a hollow metal device usually made of titanium. Once inserted, the fusion cage maintains the proper separation between the vertebrae to prevent nerves from being pinched and provides structural stability to the spine. Also, the inside of the cage is filled with bone graft material which eventually fuses permanently with the adjacent vertebrae into a single unit.

The use of fusion cages for fusion and stabilization of vertebrae in the spine is known in the prior art. U.S. Pat. No. 4,961,740 to Ray, et al. entitled, "V-Thread Fusion Cage and Method of Fusing a Bone Joint," discloses a fusion cage with a threaded outer surface, where the crown of the thread is sharp and cuts into the bone. Perforations are provided in valleys between adjacent turns of the thread. The cage can be screwed into a threaded bore provided in the bone structure at the surgical site and then packed with bone chips which promote fusion.

U.S. Pat. No. 5,015,247 to Michelson entitled, "Threaded Spinal Implant," discloses a fusion implant comprising a cylindrical member having a series of threads on the exterior of the cylindrical member for engaging the vertebrae to maintain the implant in place and a plurality of openings in the cylindrical surface.

U.S. Pat. No. 6,342,074 to Simpson entitled, "Anterior Lumbar Underbody Fusion Implant and Method For Fusing Adjacent Vertebrae," discloses a one-piece spinal fusion implant comprising a hollow body having an access passage for insertion of bone graft material into the intervertebral space after the implant has been affixed to adjacent vertebrae. The implant provides a pair of screw-receiving passages that are oppositely inclined relative to a central plane. In one embodiment, the screw-receiving passages enable the head of an orthopaedic screw to be retained entirely within the access passage.

U.S. Pat. No. 5,885,287 to Bagby entitled, "Self-tapping Interbody Bone Implant," discloses a bone joining implant with a rigid, implantable base body having an outer surface with at least one bone bed engaging portion configured for engaging between a pair of bone bodies to be joined, wherein at least one spline is provided by the bone bed engaging portion, the spline being constructed and arranged to extend outwardly of the body and having an undercut portion.

U.S. Pat. No. 6,582,467 to Teitelbaum et al. entitled, "Expandable Fusion Cage," discloses an expandable fusion cage where the surfaces of the cage have multiple portions cut out of the metal to form sharp barbs. As the cage is expanded, the sharp barbs protrude into the subcortical bone of the vertebrae to secure the cage in place. The cage is filled with bone or bone matrix material.

U.S. Pat. No. 5,800,550 to Sertich entitled, "Interbody Fusion Cage," discloses a prosthetic device which includes an inert generally rectangularly shaped support body adapted to be seated on hard end plates of vertebrae. The support body has top and bottom faces. A first peg is movably mounted in a first aperture located in the support body, and the first aperture terminates at one of the top and bottom faces of the support body. Further, the first peg projects away from the one of the top and bottom faces and into an adjacent vertebra to secure the support body in place relative to the vertebra.

U.S. Pat. No. 6,436,140 to Liu et al. entitled, "Expandable Interbody Fusion Cage and Method for Insertion," discloses an expandable hollow interbody fusion device, wherein the body is divided into a number of branches connected to one another at a fixed end and separated at an expandable end. The expandable cage may be inserted in its substantially cylindrical form and may be expanded by movement of an expansion member to establish lordosis of the spine. An expansion member interacts with the interior surfaces of the device to maintain the cage in the expanded condition and provide a large internal chamber for receiving bone in-growth material.

These patents all disclose fusion cage devices that can be inserted between vertebrae of the spine in an invasive surgical procedure. Such an invasive surgical procedure requires a long recovery period.

SUMMARY OF THE INVENTION

The present invention is a bone fusion device for insertion between bones that are to be fused together, such as, for example, the vertebrae of a spinal column. The bone fusion device comprises one or more extendable tabs. The bone fusion device is in its most compact state when the tabs are aligned with the body of the device such that the tabs lie within the exterior of the device. In this compact form, the bone fusion device is preferably inserted between the vertebrae by using an arthroscopic procedure. The bone fusion device of some embodiments is filled with bone graft material. In these embodiments, the bone graft material is typically relocated from the interior to the exterior of the bone fusion device by using a lead screw. After the device has been positioned between the vertebrae, and the lead screw is inserted to optionally deliver the bone graft material, selected tabs are extended. Preferably, two tabs are extended upon rotating a rotating means wherein extending blocks travel up the screw pushing out the angled tabs as the extending blocks approach the ends of the bone fusion device. The position of each tab relative to the bone fusion device is adjustable depending upon the configuration of the associated rotating means. In this way, the tabs are advantageously positioned in the confined space between the vertebrae to help brace the device until the bone has fused. Further, the tabs of the bone fusion device provide a larger surface area to which the bones attach and fuse during a healing period.

In some embodiments, the body of the bone fusion device is a round cylinder with end faces. The bone fusion device has conduits or holes that allow the bone graft material within the device to flow to the exterior of the device where the material contacts and grafts to the vertebrae. The extendable tabs are arranged in various configurations on the exterior of the bone fusion device, including the end faces. Preferably, the bone fusion device is rectangular and the tabs are attached to the body of the device on more than one side to optimally brace the device from multiple directions between the adjacent vertebrae. Alternatively, the bone fusion device has a rectangular shape with end faces and extendable tabs attached to multiple exterior surfaces. In some embodiments, the bone fusion device of some embodiments includes protrusions, threading, and/or sharp features on the exterior surface and/or the extendable tabs. These features are configured to engage the adjacent vertebrae to provide a tighter interface between the device and the vertebrae. In some embodiments, the tabs comprise stops to prevent the tabs from extending too far out of the body. In some embodiments, the device comprises a radio frequency identifier chip for providing information about the device and/or other information. In some embodiments, the device comprises one or more retention springs for biasing the tabs in the retracted position. In some embodiments, the tabs comprise a plurality of nested levels that enable the extending of the tabs to comprise the telescoping of the levels in order to increase stability and the amount of extension. In some embodiments, the tabs comprise one or more tongues that increase the top surface area of the tabs such that there is more surface area to contact and fuse to the bones.

One aspect of the application is directed to a bone fusion device for insertion into a desired location. The bone fusion device comprises a body having a first end and an interior cavity, one or more tabs configured to selectively move from a retracted position within the body to an extended position extending out of the body in order to brace the bone fusion device in the desired location, a positioning element positioned through the first end of the body and substantially within the interior cavity of the body, one or more extending blocks coupled to the positioning element for moving the one or more tabs between the retracted position and the extended position and one or more retention springs configured to apply a force to the tabs biasing the tabs in the retracted position. In some embodiments, the retention springs comprise one or more wires coupled to the body and positioned such that the wires impede a portion of the tabs from moving to the extended position thereby biasing the tabs in the retracted position. In some embodiments, the portion of each of the tabs comprise one or more channels that receive a portion of the wires in order to prevent the wires from slipping off of the portion of the tabs. In some embodiments, the portion of each of the tabs comprise one or more apertures through which the wires are threaded in order to secure wires to the portion of the tabs. In some embodiments, the retention springs comprise one or more wires each surrounding the tabs such that the wires resist separation of the tabs thereby biasing the tabs in the retracted position. In some embodiments, the retention springs comprise one or more wires coupled to the body and the tabs such that the wires resist movement of the tabs with respect to the body thereby biasing the tabs in the retracted position. In some embodiments, the retention springs comprise one or more wires each coupled to two or more of the tabs such that the wires resist separation of the two or more tabs thereby biasing the tabs in the retracted position. In some embodiments, the retention springs comprise one or more flexible portions of the body positioned such that the flexible portions of the body impede a portion of the tabs from moving to the extended position thereby biasing the tabs in the retracted position.

A second aspect of the application is directed to a bone fusion device for insertion into a desired location. The bone fusion device comprises a body having a first end, an interior cavity and an inner surface having one or more recesses, one or more tabs each having one or more stops protruding from the perimeter of the tabs, wherein the tabs are configured to selectively move from a retracted position within the body to an extended position extending out of the body in order to brace the bone fusion device in the desired location, a positioning element positioned through the first end of the body and substantially within the interior cavity of the body and one or more extending blocks coupled to the positioning element for moving the one or more tabs between the retracted position and the extended position, wherein the recesses are configured to receive the stops when the tabs are inserted into the body and to prevent the tabs from separating from the body by blocking the outward movement of the stops when the tabs are in the extended position. In some embodiments, the bottom of the outward surface of each of the stops is closer to the perimeter of the tabs than the top of the outward surface of each of the stops such that each the stop comprises an angled outward face with respect to the perimeter of the tabs in order to facilitate the insertion of the stops into the recesses of the body. In some embodiments, a top portion of each of the stops is separated from the perimeter of the tabs such that the top portion is able to flex toward the perimeter of the tabs in order to facilitate the insertion of the stops into the recesses of the body. In some embodiments, the device further comprises one or more retention springs configured to apply a force to the stops of the tabs thereby biasing the tabs in the retracted position. In some embodiments, the retention springs comprise one or more wires coupled to the body and positioned such that the wires impede the stops of the tabs from moving to the extended position thereby biasing the tabs in the retracted position. In some embodiments, the retention springs comprise one or more wires coupled to the body and the stops of the tabs such that the wires resist movement of the tabs with respect to the body thereby biasing the tabs in the retracted position. In some embodiments, the retention springs comprise one or more wires each coupled to the stops of two or more of the tabs such that the wires resist separation of the two or more tabs thereby biasing the tabs in the retracted position. In some embodiments, the retention springs comprise one or more flexible portions of the body positioned such that the flexible portions of the body impede the stops of the tabs from moving within the recesses when the tabs are moving toward the extended position thereby biasing the tabs in the retracted position.

Yet another aspect of the application is directed to a telescoping bone fusion device for insertion into a desired location. The telescoping bone fusion device comprises a body having a first end and an interior cavity, one or more tabs each having a plurality of nested levels configured to selectively telescope between a retracted position within the body and extended positions extending out of the body in order to brace the bone fusion device in the desired location, a positioning element positioned through the first end of the body and substantially within the interior cavity of the body and one or more extending blocks coupled to the positioning element for moving the nested levels of the one or more tabs between the retracted position and the extended positions. In some embodiments, each of the nested levels of each tab has a maximum extended position that is different than the maximum extended position of the other nested levels of the tab. In some embodiments, the distance from the body of the maximum extended position for each of the nested levels of each tab increases from the outermost nested level to the innermost nested level. In some embodiments, each of the nested levels of each tab include an inner surface having a profile that is different than the inner surface profile of the other nested levels of the tab, and further wherein at least one of the extending blocks is configured to contact the inner surfaces when moving the nested levels between the retracted position and the extended positions. In some embodiments, the one or more extending blocks comprise a plurality of upper surfaces at different heights, and further wherein the upper surfaces at each height are associated with one or more of the nested levels such that the upper surfaces of that height contact the associated nested levels when moving the nested levels between the retracted position and the extended positions. In some embodiments, the innermost nested level of each tab comprises one or more tongues that extend from the top surface of the innermost nested level to the perimeter of the tab. In some embodiments, the non-innermost nested levels of each tab comprise one or more recesses that align with the one or more tongues such that when the innermost nested level is nested within one or more of the non-innermost nested levels the tongues slide within the recesses.

Another aspect of the application is directed to a method of implanting a telescoping bone fusion device. The method comprises inserting the bone fusion device into a desired location, wherein the bone fusion device comprises a body, a positioning element, one or more extending blocks and one or more moveable tabs each having a plurality of nested levels configured to selectively telescope between a retracted position within the body and extended positions extending out of the body in order to brace the bone fusion device in the desired location, pre-configuring the one or more moveable tabs to the retracted position with the positioning element and the plurality of extending blocks such that the bone fusion device has a minimized form factor and telescoping each of the nested levels of the one or more tabs to desired extended positions by moving the plurality of extending blocks with the positioning element. In some embodiments, rotating the positioning element moves the plurality of extending blocks. In some embodiments, each of the nested levels of each tab has a maximum extended position that is different than the maximum extended position of the other nested levels of the tab. In some embodiments, the distance from the body of the maximum extended position for each of the nested levels of each tab increases from the outermost nested level to the innermost nested level. In some embodiments, each of the nested levels of each tab include an inner surface having a profile that is different than the inner surface profile of the other nested levels of the tab, and further wherein the telescoping comprises at least one of the extending blocks contacting the inner surfaces of each of the nested levels when being moved by the positioning element. In some embodiments, the one or more extending blocks comprise a plurality of upper surfaces at different heights and the upper surfaces at each height are associated with one or more of the nested levels, and further wherein the telescoping comprises the upper surfaces of the extending blocks at a height contacting the associated nested levels when being moved by the positioning element. In some embodiments, the innermost nested level of each tab comprises one or more tongues that extend from the top surface of the innermost nested level to the perimeter of the tab. In some embodiments, the non-innermost nested levels of each tab comprise one or more recesses that align with the one or more tongues such that when the innermost nested level is nested within one or more of the non-innermost nested levels the tongues slide within the recesses. In some embodiments, the method further comprises inserting a distraction instrument having an indicator and a pair of distraction plates into the desired location, separating the distraction plates and displaying information corresponding to the separation of the distraction plates with the indicator.

Another aspect of the application is directed to a bone fusion device for insertion into a desired location. The bone fusion device comprises a housing comprising first and second ends, one or more tabs for bracing the bone fusion device in a space in the desired location, each tab comprising a first tab end proximate the first end and a second tab end distal from the first end and proximate the second end, a positioning element positioned through the first end and a plurality of extending blocks coupled to the positioning element and in contact with the one or more tabs for moving the one or more tabs, wherein as the positioning element moves in a first direction the plurality of extending blocks raise the tabs toward an extended position and directly support the first tab end or the second tab end when in the extended position. In some embodiments, the device further comprises a radio frequency identification device that uniquely identifies the bone fusion device.

Another aspect of the application is directed to a method of implanting a bone fusion device in a desired location. The method comprises inserting the bone fusion device in the desired location, wherein the bone fusion device comprises a first end, a second end, an internal cavity, a positioning element, a plurality of extending blocks and one or more moveable tabs each in contact with one of the extending blocks and comprising a first tab end proximate the first end and a second tab end distal from the first end and proximate the second end and extending the one or more tabs to an extended position by moving at least one of the plurality of extending blocks toward the first end or the second end of one or more of the tabs by rotating the positioning element, wherein the at least one extending block directly supports the first tab end or the second tab end of the one or more of the tabs when the tabs are in the extended position. In some embodiments, the method further comprises inserting a distraction instrument having an indicator and a pair of distraction plates into the desired location, separating the distraction plates and displaying information corresponding to the separation of the distraction plates with the indicator.

Yet another aspect of the application is directed to a method of operating the retraction instrument for implanting a bone fusion device having one or more tabs and a positioning element. The method comprises inserting a distraction instrument having an indicator and a pair of distraction plates into a desired location, separating the distraction plates and displaying information corresponding to the separation of the distraction plates with the indicator. In some embodiments, the displayed information indicates the amount of separation between the distraction plates. In some embodiments, the displayed information indicates the amount of force resisting the distraction of the plates. In some embodiments, the displayed information indicates a size or type of bone fusion device. In some embodiments, the displayed information indicates a number of rotations that the positioning element of the bone fusion device will require in order to extend the one or more tabs such that the height of the bone fusion device equal the amount of distraction of the distraction plates. In some embodiments, the desired position comprises between one or more vertebrae. In some embodiments, the method further comprises collapsing the distraction plates together and removing the distraction instrument from the desired location.

BRIEF DESCRIPTION OF THE DRAWINGS

FIGS. 7A-B are perspective drawings illustrating the tabs and tab bays of some embodiments.

DETAILED DESCRIPTION

In the following description, numerous details and alternatives are set forth for purpose of explanation. However, one of ordinary skill in the art will realize that the invention can be practiced without the use of these specific details. For instance, the figures and description below often refer to the vertebral bones of a spinal column. However, one of ordinary skill in the art will recognize that some embodiments of the invention are practiced for the fusion of other bones, including broken bones and/or joints. In other instances, well-known structures and devices are shown in block diagram form in order not to obscure the description of the invention with unnecessary detail.

Figure 1:
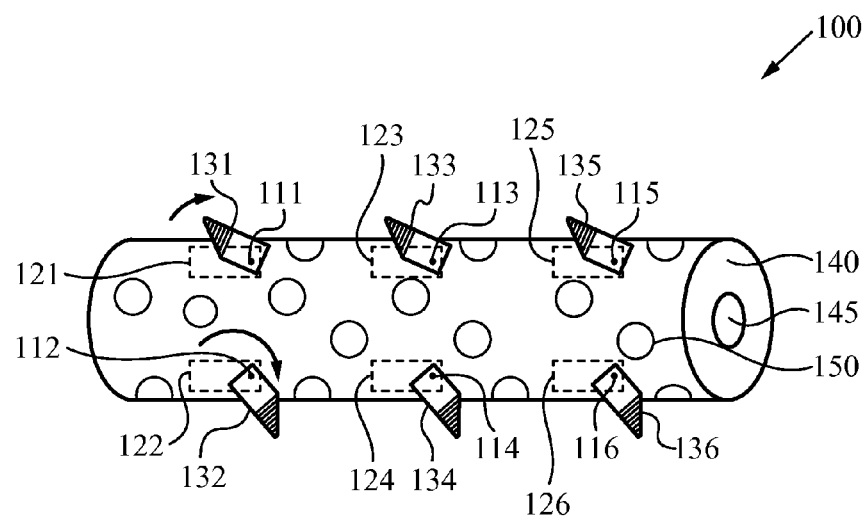
FIG. 1 illustrates a bone fusion device in accordance with some embodiments of the invention.

FIG. 1 illustrates a bone fusion device 100 in accordance with some embodiments of the invention. As shown in this figure, the bone fusion device 100 has a round cylindrical shape and has two end faces, including the end face 140. In some embodiments, the bone fusion device 100 is constructed from a high strength biocompatible material, such as titanium, which has the strength to withstand compressive and shear forces in the spine that are generated by a patient's body weight and daily movements. The base biocompatible material is often textured or coated with a porous material conducive to the growth of new bone cells on the bone fusion device 100.

Also shown in FIG. 1, the end face 140 has an opening 145 which allows the insertion of bone graft material into the bone fusion device 100. The bone graft material includes bone chips from the same patient (autograft), bone chips from a donor (allograft or xenograft), and/or a synthetic bone matrix. The bone graft material typically promotes bone growth during a recovery period after the patient receives bone fusion surgery. As further illustrated in FIG. 1, the bone fusion device 100 has several conduits or holes 150, which permit the bone graft material to contact the vertebral bone after the device 100 has been inserted between the vertebrae of the patient. The bone graft material and the surface texturing of the device 100 encourage the growth and fusion of bone from the neighboring vertebrae. The fusion and healing process will result in the bone fusion device 100 becoming embedded within the two adjacent vertebrae of the spine which eventually fuse together during the healing period.

As further illustrated in FIG. 1, several tabs 131, 132, 133, 134, 135, and 136 are distributed along the round cylindrical body of the bone fusion device 100. These tabs 131-136 are each attached to the bone fusion device 100 by a respective rotating means 111, 112, 113, 114, 115, and 116. The rotating means 111-116 is typically a turn screw type assembly. When the bone fusion device 100 is inserted into the patient's body, the tabs 131-136 lie along the body of the device 100, as shown by the dotted outlines 121-126 of the tabs. Thus, the unextended tabs 121-126 of the bone fusion device 100 provide a compact assembly that is suitable for insertion into the patient's body through an arthroscopic surgical procedure. An arthroscopic procedure is considered minimally invasive and has certain advantages over more invasive conventional surgical procedures. In an arthroscopic procedure, a smaller surgical incision is employed as compared to the size of the incision required for conventional invasive surgery. Moreover, arthroscopic procedures minimize or eliminate the need for excessive retraction of a patient's tissues such as muscles and nerves, thereby minimizing trauma and injury to the muscles and nerves and further reducing the patient's recovery time.

After insertion of the device 100 into the space between the patient's vertebrae, the surgeon selectively extends particular tabs 131-136 by rotating each selected tab's respective rotating means 111-116. The more each rotating means 111-116 is rotated, the farther its respective tab 131-136 elevates and extends outward from its initial position 121-126 along the body of the device 100. Each tab's 131-136 position is individually adjustable so as to optimally brace the device 100 between the vertebrae. Due to the compressive forces commonly associated with spinal column vertebrae, some embodiments include a range of motion for each tab that is slightly greater than 90 degrees. It was particularly discovered during the reduction to practice of this aspect of the present invention, that the tabs of these embodiments are rotated to an angle that is slightly more than about 90 degrees with respect to the surface of the bone fusion device. The tabs extended in this configuration were found to be capable of withstanding the greatest amount of compressive force.

The tabs 131-136, when extended, abut tightly against the surfaces of the vertebrae that are immediately adjacent to the bone fusion device 100. In some embodiments, the tabs 131-136 have sharp protrusions along the length of the tab for engaging the adjacent vertebrae, while the tabs 131-136 of some embodiments have screw-type threads for screwing into and engaging the vertebrae. Optionally, the tabs of some embodiments have surface texturing to encourage and enhance the growth of new bone on the tabs 131-136. This surface texturing is often similar to the surface texturing used on the main body of the device 100. Regardless of their texturing and/or particular physical characteristics, the tabs 131-136 advantageously wedge the bone fusion device 100 in a fixed position between the vertebrae and provide a larger surface area with which the adjacent vertebrae fuses during the healing period. Moreover, bone growth material, such as protein, is typically applied to the tabs 131-136 to stimulate the regeneration of bone cells needed for bone fusion. The application of bone growth material is described further in relation to FIG. 4.

In an alternative embodiment of the invention, the tabs of the device 100 have sharp ridges or threads which bite into the adjacent vertebrae, further helping to brace the device between the vertebrae. It will be readily apparent to one skilled in the art that there are a number of variations for the body and the tabs 131-136 of the bone fusion device 100. For instance, the bone fusion device 100 employs different numbers and/or configurations of tabs in different embodiments. Hence, the tabs 131-136 depicted in FIG. 1 are merely exemplary. Moreover, the tabs 131-136 are located anywhere over the exterior surface of the bone fusion device 100, in a variety of orientations. Specifically, the tabs 131-136 are arranged such that when they are extended, the tabs 131-136 act to stabilize the bone fusion device 100 against the vertebrae from several points and directions. Typically, the tighter the bone fusion device 100 is wedged between the adjacent vertebrae by the tabs 131-136, the more stability the device 100 provides to the vertebrae and the spine of the patient. The tabs 131-136 of the embodiments described above are critical to insure that the device 100 is not dislodged, since movement of the device 100 could cause serious injury to the patient, and especially because the inserted device is situated near the patient's spinal cord.

Figure 2:
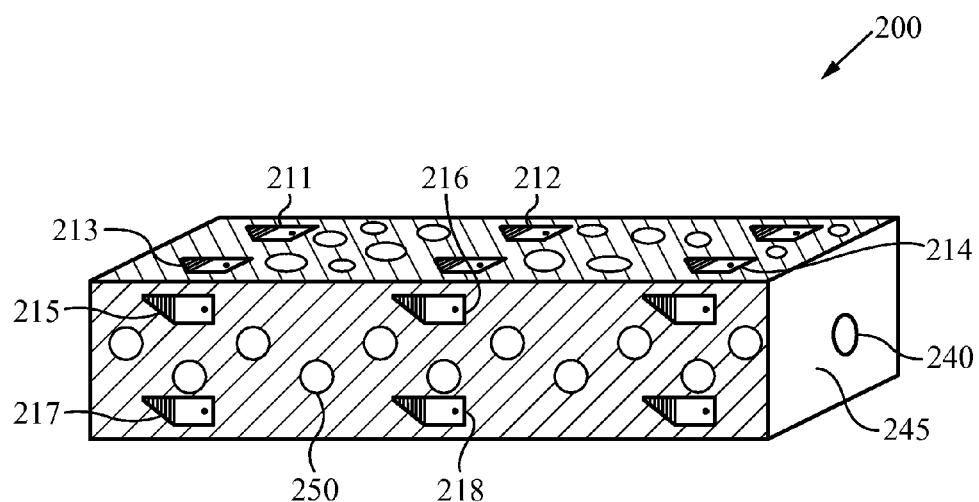
FIG. 2 illustrates a bone fusion device according to an alternative embodiment of the present invention.

FIG. 2 shows an alternative embodiment of the bone fusion device 200. As shown in this figure, the bone fusion device 200 of some embodiments has a rectangular shape. Similar to the round cylindrical shaped bone fusion device 100 shown in FIG. 1, the rectangular bone fusion device 200 has two end faces, including the end face 245 visible in FIG. 2, and multiple tabs 211, 212, 213, 214, 215, 216, 217, and 218 that are attached by rotating means to the exterior surface. The rotating means are screw type assemblies in some embodiments. The tabs 211-218 are also selectively extended after insertion of the bone fusion device 200 between the vertebrae. As before, the insertion of the bone fusion device 200 and the extension of the selected tabs 211-218, are typically performed by a surgeon during an arthroscopic surgical procedure. The procedure of some embodiments is further described in relation to FIG. 8. The rotation of a respective rotating means associated with each tab 211-218, individually adjusts the position of the associated tab 211-218 such that the device 200 is firmly braced between the two adjacent vertebrae. One skilled in the art will recognize that the tabs 211-218 are distributed over the exterior surfaces of the bone fusion device 200 in a variety of configurations, which include the ends and the surfaces of the device 200 that are not readily visible in FIG. 2. Moreover, as mentioned above, different numbers of tabs 211-218 are distributed over each surface of the bone fusion device 200 of different embodiments. In some embodiments, the surfaces of the bone fusion device 200 and/or the tabs 211-218, are coated with a porous surface texturing which promotes bone growth.

The end face 245 has an opening 240, which provides access to a cavity within the interior of the bone fusion device 200. In some embodiments, bone graft materials, such as the bone chips and/or the synthetic bone matrix that were mentioned above, are pre-loaded into the cavity within the bone fusion device 200 through the opening 240. Several conduits or holes 250 in the bone fusion device 200 permit the bone graft material to flow from the interior cavity to the exterior surfaces of the device 200 that are in contact with the vertebral bone. Typically, the bone graft material is relocated from the interior cavity to the exterior of the bone fusion device 200, after the device 200 has been positioned between the vertebrae. However, in some embodiments the bone graft material is delivered to the site of the bone fusion device 200 by arthroscopic means that originate external to the device 200. Regardless of the delivery means, the bone graft material and the surface texturing of the bone fusion device 200 encourage bone growth and fusion with the adjacent vertebrae that are in contact with the device 200. As bone fusion and healing progresses, the bone fusion device 200 becomes embedded within the two fused vertebrae of the spine.

Figure 3A:
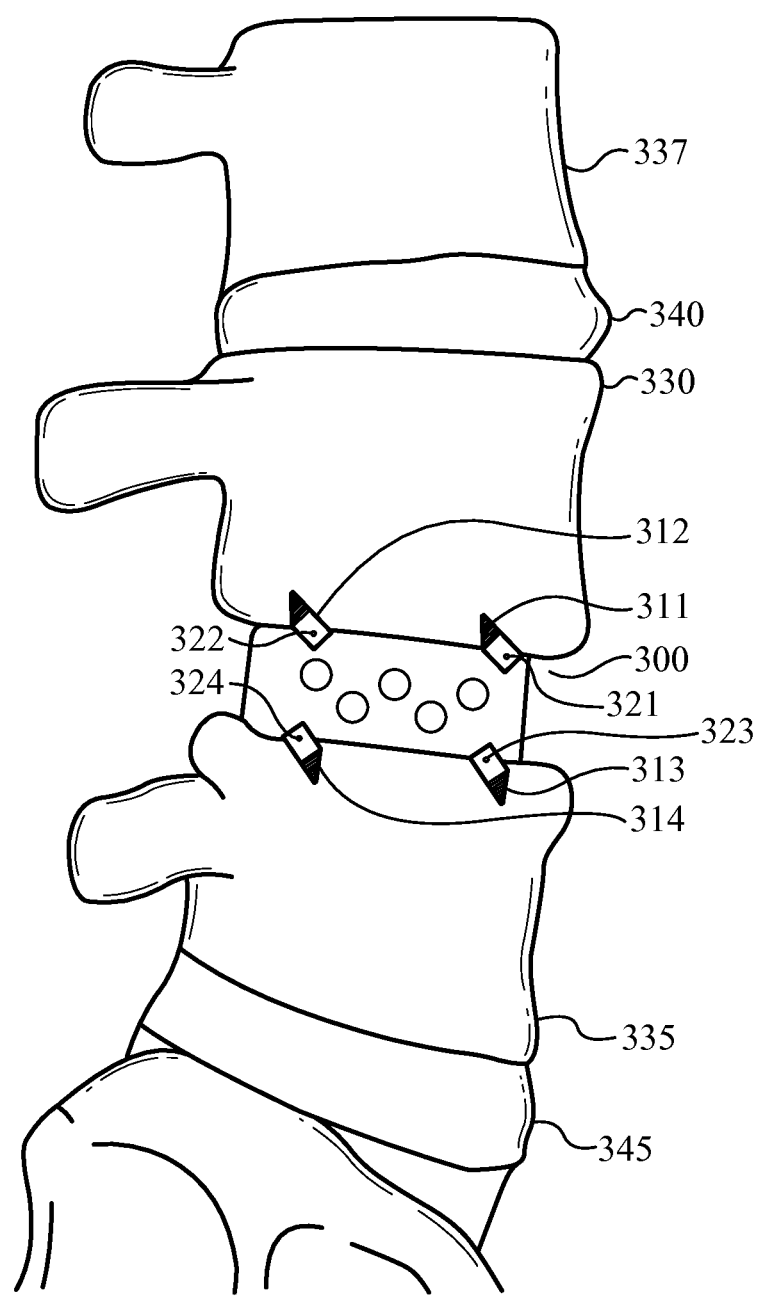
FIGS. 3A-B illustrate a section of a vertebral column showing the bone fusion device inserted between two adjacent vertebrae in place of an intervertebral disc.

FIG. 3A illustrates a section of a vertebral column that has a bone fusion device 300 positioned between two vertebrae 330 and 335. As shown in this figure, the bone fusion device 300 is positioned in a location where an intervertebral disc would normally reside. A flexible disc is typically sandwiched between the two vertebrae of a normal healthy spinal column. For instance, the normal, healthy disc 340 is sandwiched between the vertebrae 337 and 330. However, for the spinal column illustrated in FIG. 3, the intervertebral disc that normally resides between the vertebrae 330 and 335 has been excised and surgical insertion of the bone fusion device 300 has replaced the disc as the supporting structure between the vertebrae 330 and 335.

FIG. 3A further illustrates that the damaged disc that is normally sandwiched between vertebrae 330 and 335 has been totally removed. However, complete removal of the disc is not necessary in order to use the bone fusion device 300 of some embodiments. Typically, only as much of the disc needs to be excised as is required to permit the placement and positioning of the bone fusion device 300. Additionally, a sufficient amount of the disc is typically removed that allows access to the rotating means 311, 312, 313, and 314, which control the extension of the tabs 321, 322, 323, and 324, of the bone fusion device 300. As mentioned above, additional numbers and configurations of the tabs are distributed over the exterior surfaces of the bone fusion device 300, including the surfaces that are not visible in FIG. 3A.

During the insertion and placement of the bone fusion device 300, the tabs 321-324 are deposed in a position aligned along the body of the bone fusion device 300, such that the tabs 321-324 lie substantially within the exterior surfaces of the device 300. In some embodiments, the tabs 321-324 are flush with the exterior surface. In these embodiments, the form factor of the bone fusion device 300 is configured to be as compact as possible. For instance, the form factor of some embodiments has a diameter of approximately 0.28 inches and a length of approximately 1.0 inch. In contrast, the form factor of these same embodiments has a diameter of approximately 0.48 inches when the tabs 321-324 are fully extended.

By minimizing the space occupied, the bone fusion device 300 is advantageously inserted arthroscopically into the patient's body. If instead, the device 300 were inserted in its fully extended form, a larger surgical incision would be required, and a greater displacement of the muscles and nerves would be needed. However, its compact form factor allows the bone fusion device 300 to be inserted by advantageously utilizing minimally invasive arthroscopic techniques. Then, the tabs 321-324 of the bone fusion device 300 are extended after arthroscopic insertion to optimally increase the form factor and brace the device 300 between the vertebrae 330 and 335. In some embodiments, selected tabs 321-324 are extended.

Figure 3B:
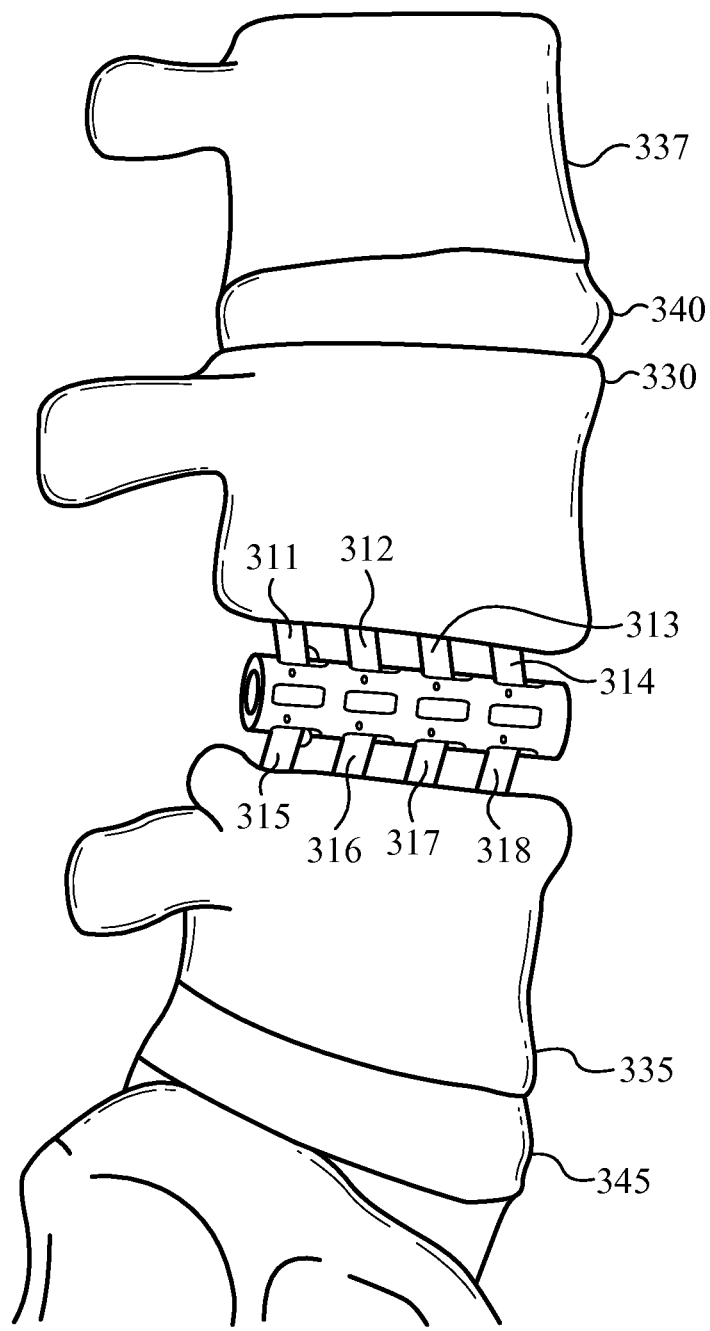

While the particular embodiment described above has a rectangular shape, it will be readily apparent to one skilled in the art that the cross-section of the bone fusion device 300 has different shapes in various embodiments. For instance, a more circular bone fusion device such as the device 100 illustrated in FIG. 1, or a device having another shape is employed in conjunction with a set of extendable tabs that are located in various configurations in additional embodiments of the invention. For instance, some embodiments have four rows of tabs, where each row is positioned on a side of the bone fusion device. In some of these embodiments, each row has four tabs. Such an embodiment is further described in relation to FIG. 7 and is illustrated in its inserted form in FIG. 3B. As shown in FIG. 3B, a first set of four tabs 311-314 lock the bone fusion device 300 against the vertebra 330, while a second set of tabs 315-318 lock the bone fusion device 300 against the vertebra 335.

Figure 4A:
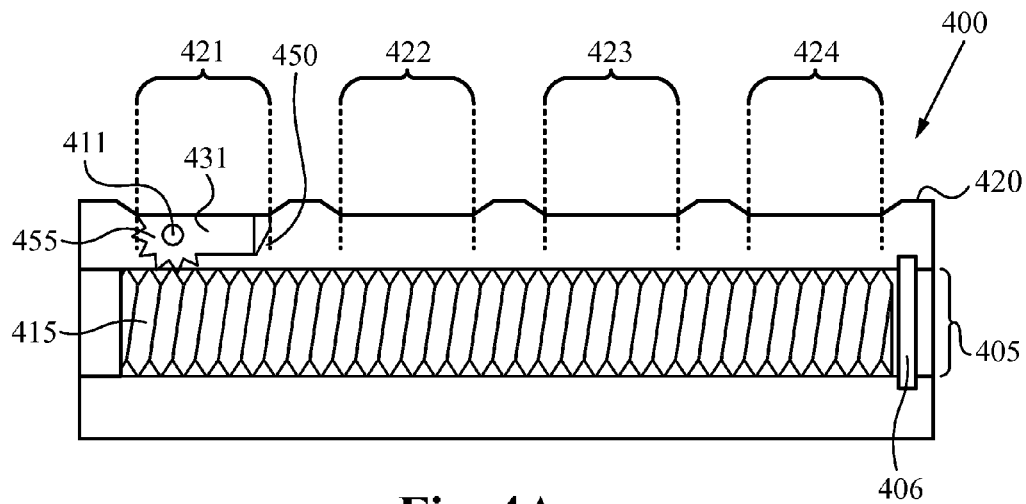
FIGS. 4A-B illustrate a detailed view of the worm screw drive and the extendable tabs of some embodiments.

FIG. 4A illustrates the bone fusion device 400 of some embodiments in further detail. As shown in this figure, the bone fusion device 400 includes an interior cavity 405 for the insertion of a lead screw 415, and one or more tabs 431 each deposed in a tab bay 421, 422, 423, 424.

The tab bays 421-424 allow the tabs 431 to lie flush and/or within the exterior surface 420 of the bone fusion device 400 when not extended. Also when not extended, the tab 431 and tab bay 421 provides a conduit 450 from the interior cavity 405 to the exterior surface 420 of the bone fusion device 400, such that the bone graft and/or growth material within the interior cavity 405 has a directed path to the exterior surface 420. Typically, the insertion of the lead screw 415 forces the material within the interior cavity 405 to relocate to the exterior surface 420.

The tab 431 includes a rotating means 411 and gear teeth 455. When the tab 431 is not extended, the gear teeth 455 provide a series of passive grooves by which the lead screw 415 traverses the interior cavity 405. Typically, the tab 431 remains fixed as the lead screw 415 is screwed into the interior cavity 405. In these embodiments, the threading of the lead screw 415 does not address or affect the gear teeth 455 during the insertion of the lead screw 415.

However, the gear teeth 455 do employ the threading of the lead screw 415 when the lead screw 415 has been fully inserted into the cavity 405, in some embodiments. For instance, in a particular implementation of the invention, the lead screw 415 is driven into the cavity 405, until it reaches an endcap 406. The endcap 406 allows the lead screw 415 to continue rotating in place, but does not allow the lead screw 415 to continue its forward progress through the cavity 405. When the lead screw 415 of these embodiments rotates without making forward progress, the rotating lead screw's threading contacts and engages the gear teeth 455 of each tab 431. Accordingly, the motion and angle of the spiraling threads, when applied against the gear teeth 455, causes the tabs 431 to elevate and extend. The combination of the gear teeth 455 on the tabs 431 and the inserted lead screw 415, is referred to, in some embodiments, as a worm screw drive mechanism.

In an alternative embodiment of the worm screw drive mechanism, the rotating means 411 is turned to raise the tab 431. In these embodiments, the rotating means 411 for the tab 431 typically comprises a turn screw type mechanism such that when the rotating means 411 is turned, the gear teeth 455 drive or rotate against the stationary threads of the inserted lead screw 415. Similarly, due to the angle of the stationary lead screw's spiral threads, the gear teeth 455 cause the tab 431 to elevate and extend above the exterior surface 420 of the bone fusion device 400.

Figure 4B:
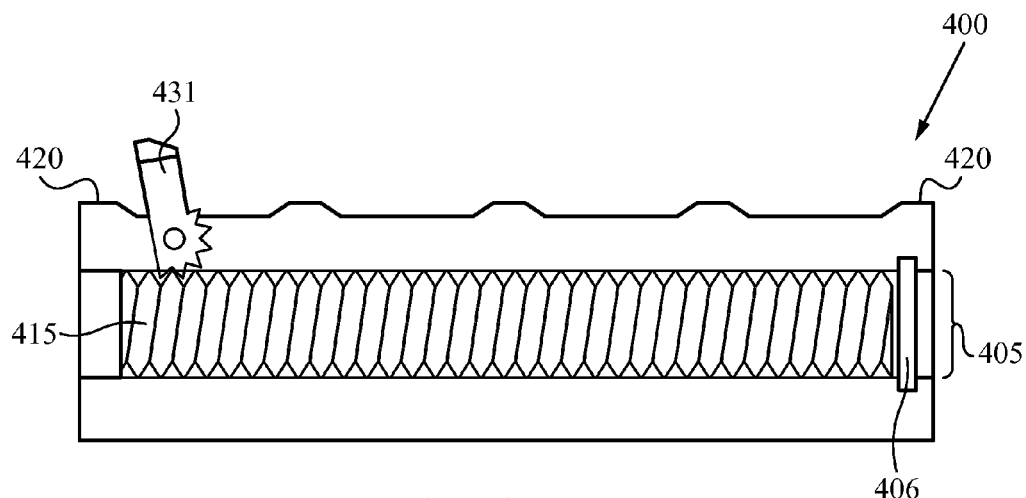

As mentioned above, the tabs 431 of some embodiments have a range of motion that exceeds 90 degrees with respect to the exterior surface 420 of the bone fusion device 400. Accordingly, FIG. 4B illustrates the tab 431 extended slightly past 90 degrees, which is the optimum position to withstand the compressive force exerted on the vertebrae of some embodiments.

Figures 5A, 5B:
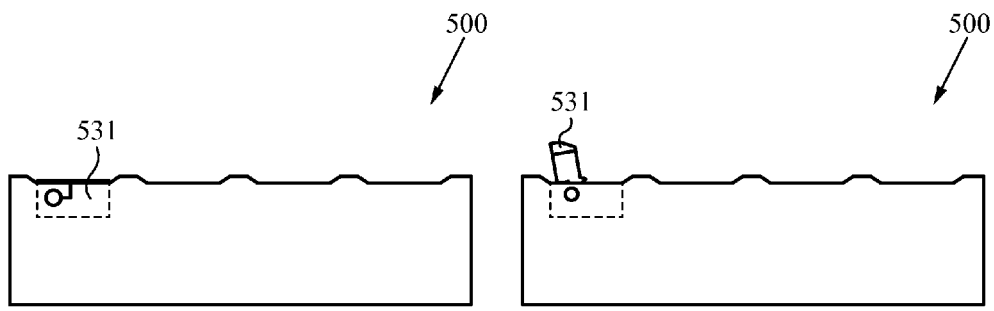
FIGS. 5A-B illustrate the small form factor of some embodiments.
Figures 6A, 6B:
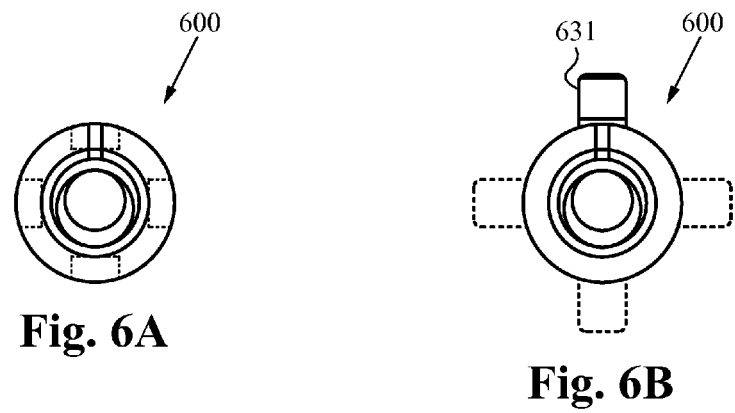
FIGS. 6A-B illustrate a cross section view of the small form factor of some embodiments.

FIG. 5A illustrates a closed view of the small form factor for a bone fusion device 500 in accordance with some embodiments. As shown in this figure, the bone fusion device 500 has a tab 531 that is not extended and lies within the exterior surface of the device 500. In contrast, FIG. 5B illustrates the form factor for the bone fusion device 500 with the tab 531 extended, as described above. Similarly, FIG. 6A illustrates a cross section view of the bone fusion device 600 having a small form factor, while FIG. 6B illustrates the cross section view with the tab 631 extended.

Figure 7B:
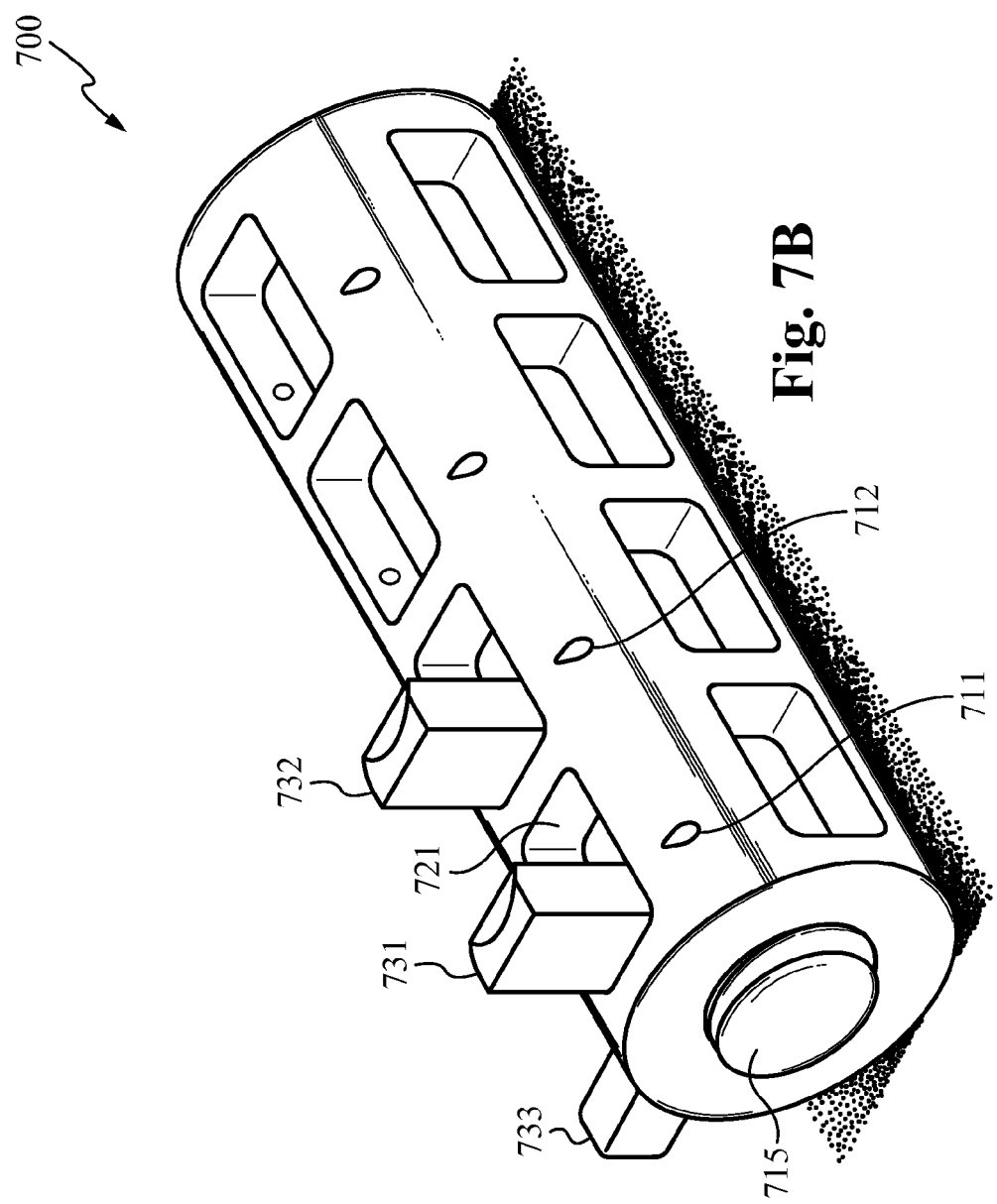

FIG. 7A is a perspective drawing illustrating the bone fusion device 700 with four tab bays on four opposite sides of the device 700, according to some embodiments of the invention. As described above, a tab is deposed in each tab bay and secured by a rotating means. For instance, the tab 731 is deposed in the tab bay 721 and secured by the rotating means 711. Also shown in FIG. 7A, a lead screw 715 is driven into the cavity. As described above, the lead screw 715 provides the thread by which the gear teeth 755 elevate the tabs 731-733. Accordingly, FIG. 7B illustrates the bone fusion device 700 with the tabs 731-733 elevated.

Figure 8:
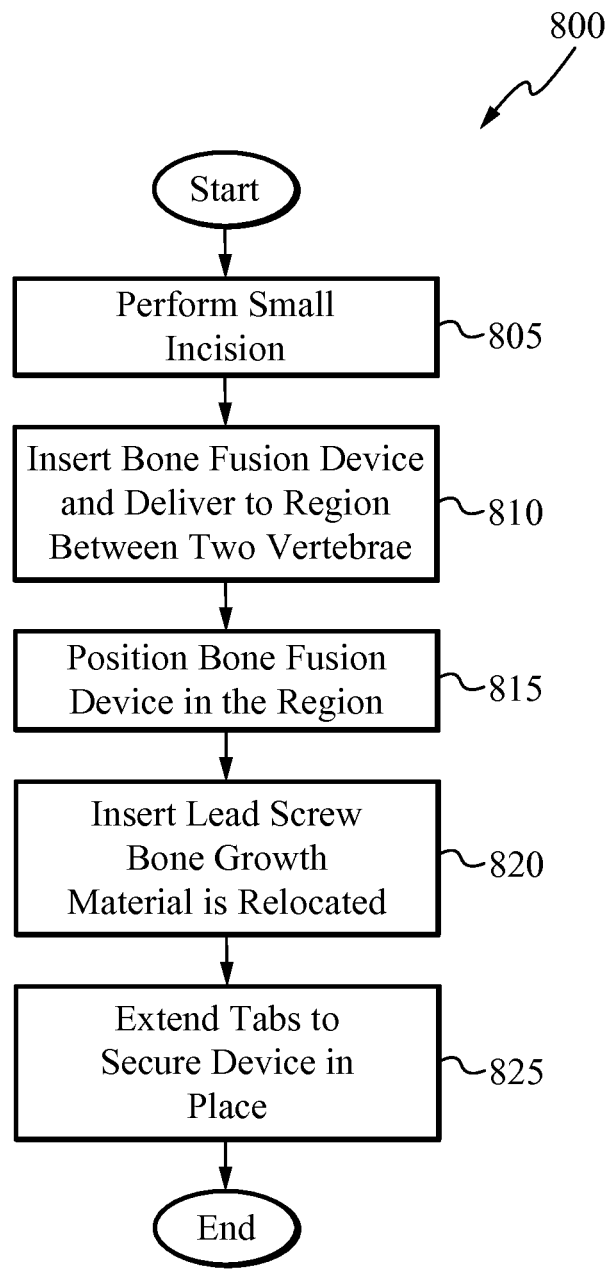
FIG. 8 illustrates a process flow in accordance with some embodiments of the invention.

FIG. 8 is a process flow diagram that summarizes the insertion and use of the bone fusion device according to some embodiments. As shown in this figure, the process 800 begins at the step 805 where a small, minimally invasive surgical incision is performed. The small incision is typically only large enough to permit entry of an arthroscopic surgical tool. Then, the process 800 transitions to the step 810, where the bone fusion device is inserted through the small incision and delivered to a region between two vertebrae that are to be fused together. Insertion and delivery of the bone fusion device are performed by using arthroscopic tool(s).

At the step 815, the bone fusion device is positioned in the region where bone fusion is to occur, also typically by using one or more arthroscopic tool(s). Once the bone fusion device is positioned in the region between the two vertebrae, the process 800 transitions to the step 820, where the lead screw is inserted and driven into the bone fusion device. The lead screw is typically driven into a cavity in the center of the bone fusion device. The cavity contains a bone growth material comprising collagen and/or a matrix for the promotion of bone growth. Accordingly, insertion of the lead screw into the cavity causes the bone growth material to be relocated from the interior cavity to the exterior surface of the bone growth device. The bone fusion device of some embodiments has a particular pattern of conduits or pores that extend from the interior cavity to the exterior surface for facilitating the relocation of bone growth material to particular locations at the exterior of the device. For instance, some embodiments have pores that facilitate the relocation of bone growth material to particular tabs.

At the step 825 of the FIG. 8, the tabs are selectively extended to lock the bone fusion device in place in the region between the two vertebrae. The tabs of some embodiments are extended by using the worm screw drive mechanism described above in relation to FIG. 4. Once the selected tabs are extended and the bone fusion device is secured in place at the step 825, the surgical tools are removed from the patient, and the small incision is sutured. Then, the process 800 concludes.

Figure 9:
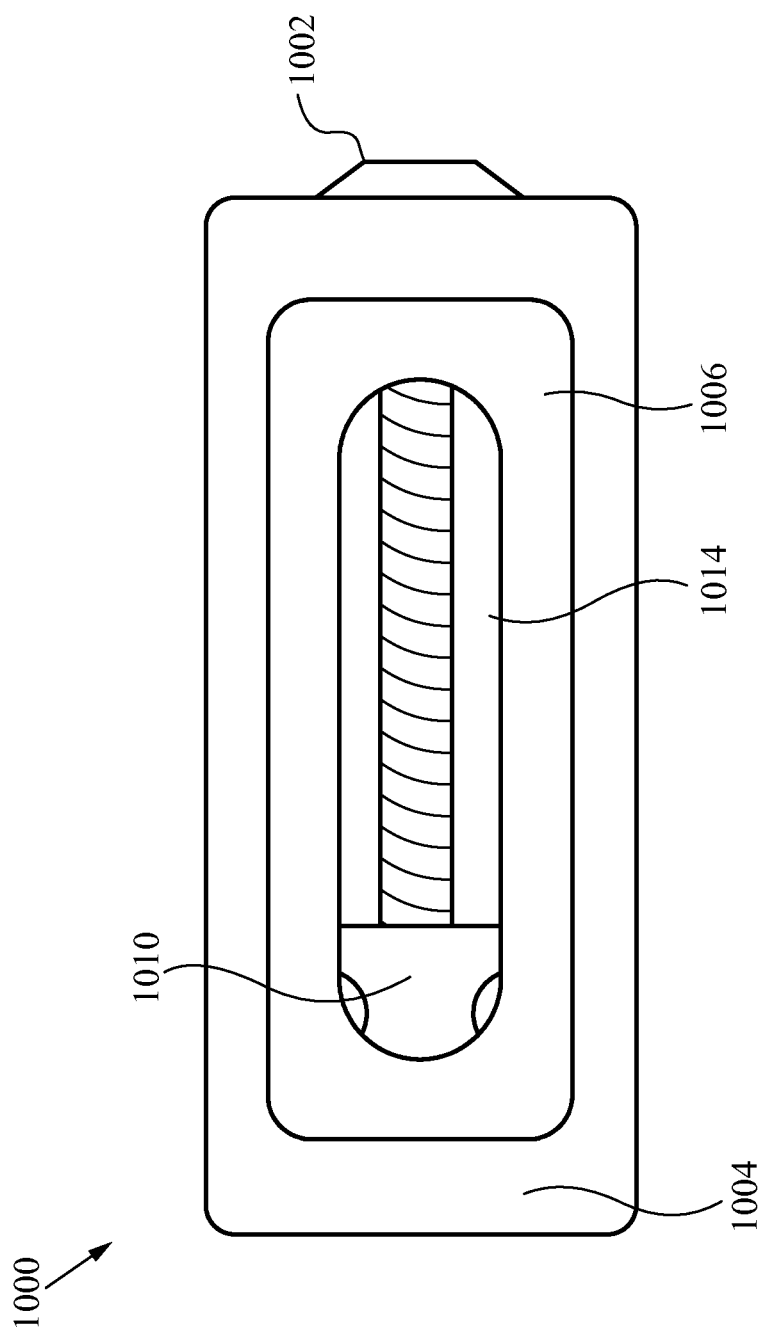
FIG. 9 illustrates a top perspective view of the bone fusion device in some embodiments of the invention.

FIG. 9 illustrates a top perspective view of the bone fusion device in some embodiments. As shown in this figure, the bone fusion device 1000 has a substantially rectangular shape and has two end faces. In some embodiments, the bone fusion device 1000 is constructed from a high strength biocompatible material, such as titanium, which has the strength to withstand compressive and shear forces in the spine that are generated by a patient's body weight and daily movements. The base biocompatible material is often textured or coated with a porous material conducive to the growth of new bone cells on the bone fusion device 1000. As further illustrated in FIG. 9, the bone fusion device 1000 has several conduits or holes 1014 which permit the bone graft material to contact the vertebral bone after the device 1000 has been inserted between the vertebrae of the patient. The bone graft material and the surface texturing of the device 1000 encourage the growth and fusion of bone from the neighboring vertebrae. The fusion and healing process will result in the bone fusion device 1000 becoming embedded within the two adjacent vertebrae of the spine which eventually fuse together during the healing period.

As further illustrated in FIG. 9, a first tab 1006 is located on a first side and a second tab 1006 (FIG. 14A) is located on an opposing second side. These tabs 1006 are shaped so that their outer surface is substantially flush with the frame 1004 of the bone fusion device 1000 in an unextended position. Internally, the tabs 1006 have an angled inner surface. Each tab 1006 is shaped such that one end is substantially larger than the opposing smaller end, and the size of the tab in between gradually decreases while going from the larger end to the opposing smaller end. A positioning means 1002 is coupled to an extending block or nut 1010 which travels up or down the positioning means 1002 depending on which way the positioning means 1002 is turned. The positioning means 1002 is typically a screw type assembly. Turning the positioning means 1002 clockwise causes the extending block 1010 to move up the positioning means 1002 towards the head of the positioning means 1002, whereas turning the positioning means 1002 counterclockwise moves the extending block 1010 away from the head of the positioning means 1002. When the extending block 1010 is positioned away from the head of the positioning means 1002, the angled tabs 1006 are compact and are within the frame 1004 of the bone fusion device 1000. Thus, the unextended tabs 1006 of the bone fusion device 1000 provide a compact assembly that is suitable for insertion into the patient's body through an arthroscopic surgical procedure. An arthroscopic procedure is considered minimally invasive and has certain advantages over more invasive conventional surgical procedures. In an arthroscopic procedure, a smaller surgical incision is employed as compared to the size of the incision required for conventional invasive surgery. Moreover, arthroscopic procedures minimize or eliminate the need for excessive retraction of a patient's tissues such as muscles and nerves, thereby minimizing trauma and injury to the muscles and nerves and further reducing the patient's recovery time. As the positioning means 1002 is rotated causing the extending block 1010 to move closer to the head of the positioning means 1002, the extending block 1010 pushes the angled tabs 1006 outward causing the tabs 1006 to assert pressure against surrounding bones and securing the bone fusion device 1000 in place. When the extending block 1006 reaches as close to the head of the positioning means 1002 as allowed, the tabs 1006 are fully extended. Furthermore, since the extending block 1010 travels along the positioning means 1002, such as along the threads of a screw, very precise positions of the tabs 1006 are able to be achieved.

Figure 10:
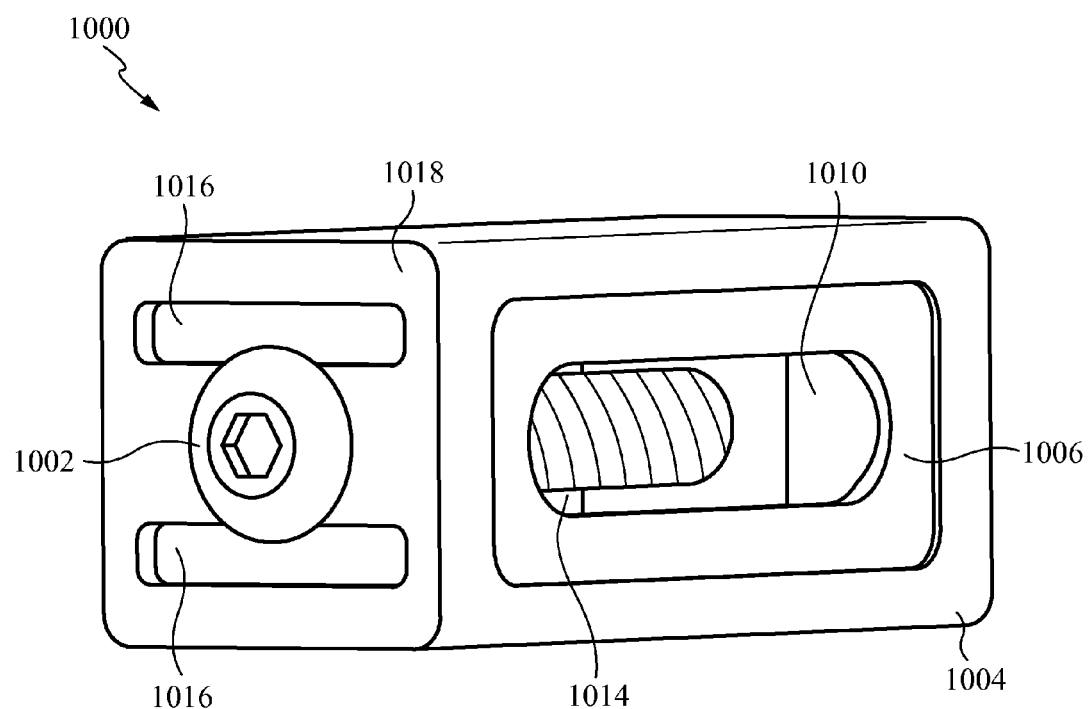
FIG. 10 illustrates a top/side perspective view of the bone fusion device in some embodiments of the invention.

FIG. 10 illustrates a top/side perspective view of the bone fusion device 1000 in some embodiments. As described above, the bone fusion device 1000 has tabs 1006 initially positioned so that they fit within the frame 1004 of the bone fusion device 1000. The positioning means 1002 is positioned through the first end face 1018 so that the extending block 1010 is able to travel along the positioning means 1002 causing the tabs 1006 to extend outwardly beyond the frame 1004 of the bone fusion device 1000. The positioning means 1002 is able to be any device that allows such functionality. Furthermore, if a screw or bolt is utilized as the positioning means 1002, any type of screw head is acceptable even though the exemplary screw slot shown in FIG. 10 requires the use of an allen wrench. Slotted, Phillips, Pozidriv, Torx, Robertson, Tri-Wing, Torq-Set, Spanner and any other heads are acceptable alternatives. Also located within the first end face 1018 are one or more apertures 1016 to allow bone graft material to contact the vertebral bone after the device 1000 has been inserted between the vertebrae of the patient. The holes 1014 within the tabs 1006 also permit the insertion of bone graft material.

Figure 11:
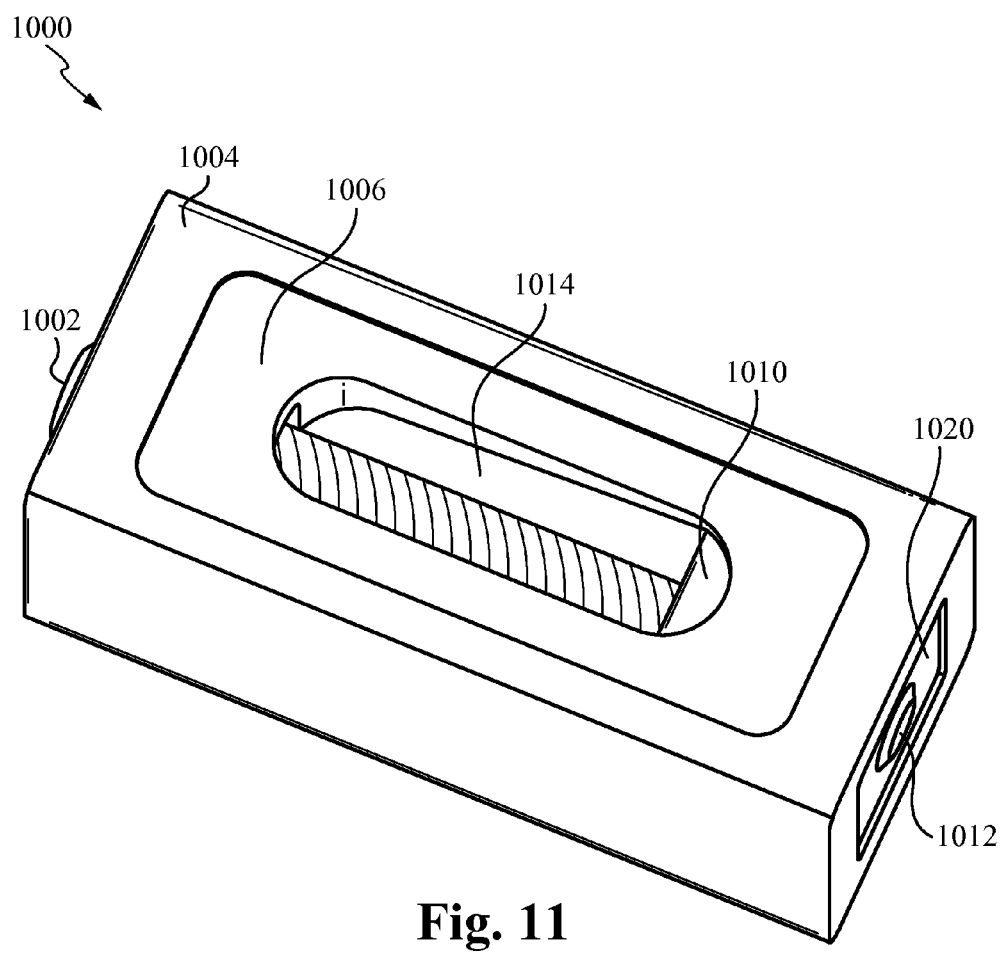
FIG. 11 illustrates a top/side perspective view of the bone fusion device in some embodiments of the invention.

FIG. 11 illustrates a top/side perspective view of the bone fusion device 1000 in some embodiments. As described before, the bone fusion device 1000 utilizes the positioning means 1002 to move the extending block 1010 up and down the body of the positioning means 1002 which forces the tabs 1006 to either extend or retract depending on the position of the extending block 1010. When the extending block 1010 is located near the head of the positioning means 1002, the extending block 1010 forces the tabs 1006 outward so that the tabs 1006 are extended beyond the frame 1000 to secure the bone fusion device 1000 in place. However, when the extending block 1010 is located away from the head of the positioning means 1002, the tabs 1006 are situated within the frame 1004, making the bone fusion device 1000 very compact. Opposing the end of the head of the positioning means is the second end face 1020 which contains an opening 1012 for providing access to a cavity within the interior of the bone fusion device 1000. In some embodiments, bone graft materials, such as the bone chips and/or the synthetic bone matrix that were mentioned above, are pre-loaded into the cavity within the bone fusion device 1000 through the opening 1012. The other holes 1014 within the tabs allow the bone graft material to contact the vertebral bone after the device 1000 has been inserted between the vertebrae of the patient.

Figure 12:
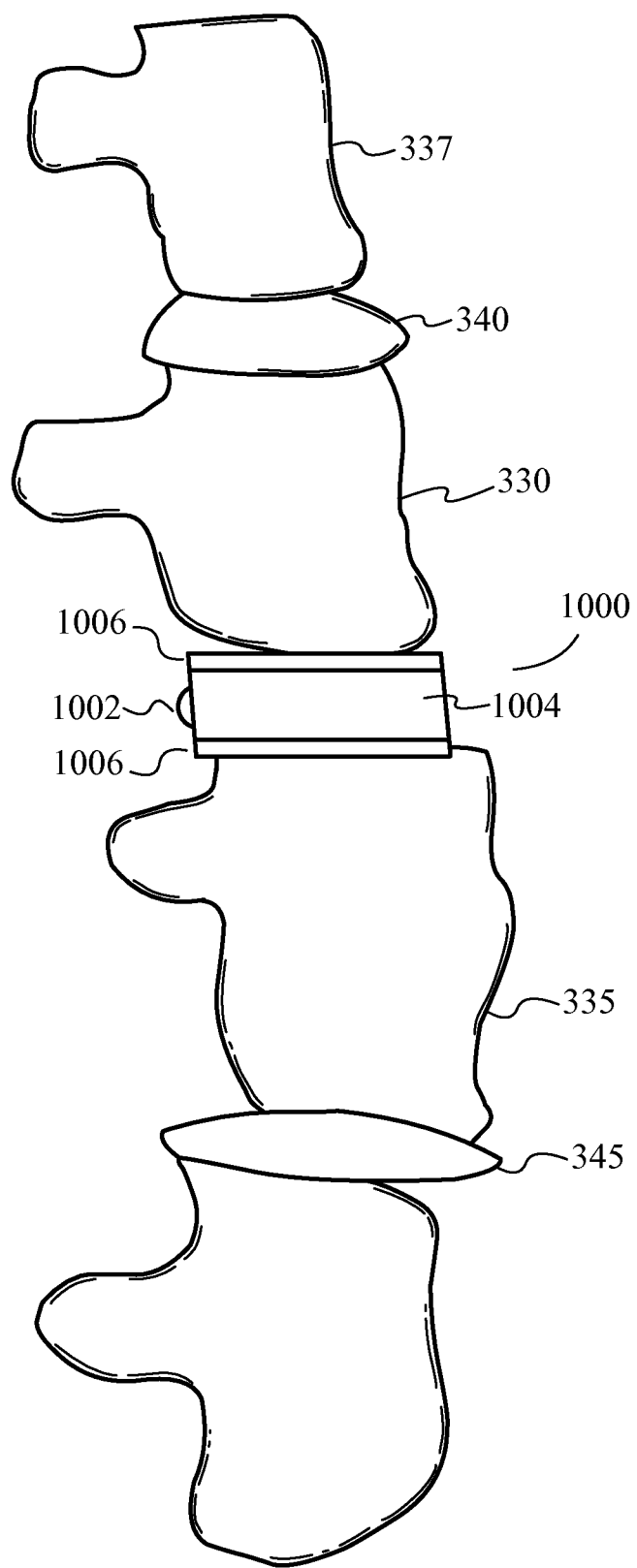
FIG. 12 illustrates a section of a vertebral column showing the bone fusion device inserted between two adjacent vertebrae in place of an intervertebral disc.

FIG. 12 illustrates a section of a vertebral column showing the bone fusion device 1000 inserted between two adjacent vertebrae 330 and 335 in place of an intervertebral disc. As shown in this figure, the bone fusion device 1000 is positioned in a location where an intervertebral disc would normally reside. A flexible disc is typically sandwiched between the two vertebrae of a normal healthy spinal column. For instance, the normal, healthy disc 340 is sandwiched between the vertebrae 337 and 330. However, for the spinal column illustrated in FIG. 12, the intervertebral disc that normally resides between the vertebrae 330 and 335 has been excised and surgical insertion of the bone fusion device 1000 has replaced the disc as the supporting structure between the vertebrae 330 and 335.

During the insertion and placement of the bone fusion device 1000, the tabs 1006 are deposed in a position aligned along the body of the bone fusion device 1000, such that the tabs lie substantially within the exterior surfaces of the device. In some embodiments, the tabs 1006 are flush with the exterior surface. In these embodiments, the form factor of the bone fusion device 1000 is configured to be as compact as possible. For example, the form factor of some embodiments has a diameter of approximately 0.28 inches and a length of approximately 1.0 inch. In contrast, the form factor of these same embodiments has a diameter of approximately 0.48 inches when the tabs 1006 are fully extended. In other embodiments the size could be larger or smaller as needed.

By minimizing the space occupied, the bone fusion device 1000 is advantageously inserted arthroscopically into the patient's body. If instead, the device 1000 were inserted in its fully extended form, a larger surgical incision would be required, and a greater displacement of the muscles and nerves would be needed. However, its compact form factor allows the bone fusion device 1000 to be inserted by advantageously utilizing minimally invasive arthroscopic techniques. Then, the tabs 1006 of the bone fusion device 1000 are extended after arthroscopic insertion to optimally increase the form factor and brace the device 1000 between the vertebrae 330 and 335.

Figure 13:
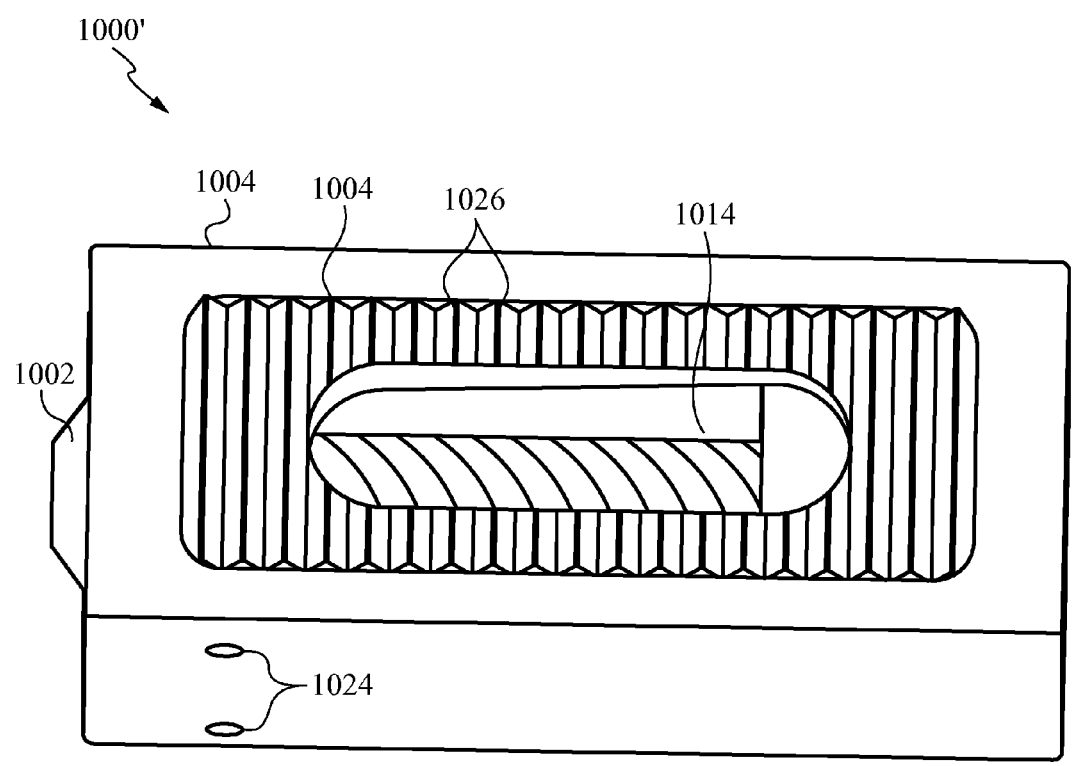
FIG. 13 illustrates a side perspective view of the bone fusion device in another embodiment of the present invention.

FIG. 13 illustrates a side view of another embodiment of the bone fusion device 1000'. The bone fusion device 1000' utilizes the positioning means 1002 to move the extending block 1010 (FIG. 9) up and down the body of the positioning means 1002 which forces the tabs 1006' to either extend or retract depending on the position of the extending block 1010 (FIG. 9). The tabs 1006' have serrated edges 1026 to further increase the bone fusion device's gripping ability to secure it in place between the bones. When the extending block 1010 (FIG. 9) is located near the head of the positioning means 1002, the extending block 1010 (FIG. 9) forces the tabs 1006' outward so that the tabs 1006' are extended beyond the frame 1000 to secure the bone fusion device 1000 in place. The tabs 1006' are each coupled to the frame 1004 of the bone fusion device 1000' by one or more slots 1028 and one or more pins 1024 wherein the one or more pins 1024 fit within the one or more slots 1028 and are able to travel along the interior of the one or more slots 1028. When the extending block 1010 (FIG. 9) is located away from the head of the positioning means 1002, the tabs 1006' are situated within the frame 1004, making the bone fusion device 1000' very compact. The holes 1014 within the tabs allow the bone graft material to contact the vertebral bone after the device 1000' has been inserted between the vertebrae of the patient.

Figure 14A:
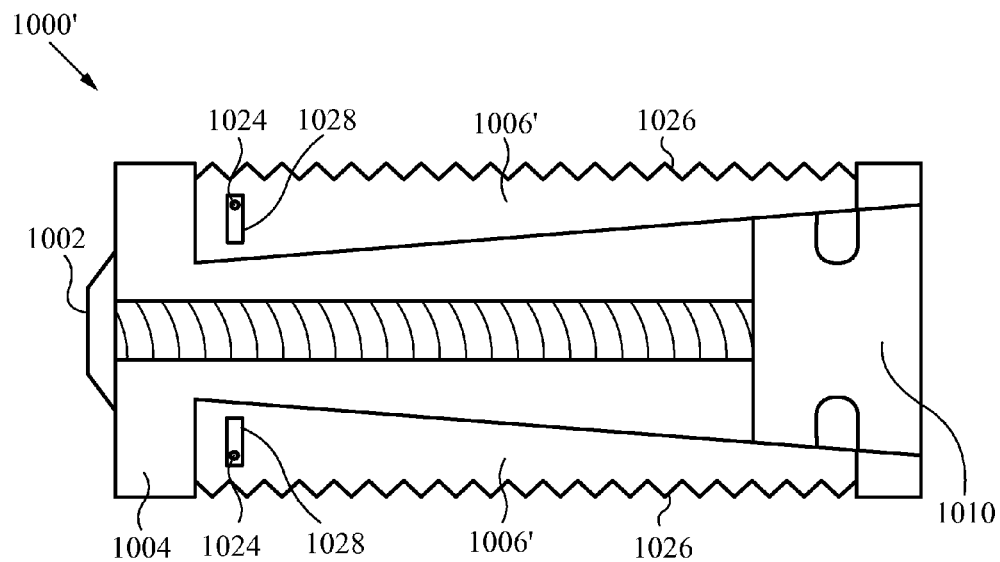
FIG. 14A illustrates a cross sectional view of the bone fusion device with the tabs compacted in another embodiment of the invention.

FIG. 14A illustrates a cross sectional view of the bone fusion device 1000' with the tabs 1006' with serrated edges 1026 compacted in another embodiment. When the extending block 1010 is positioned away from the head of the positioning means 1002 and close to the second end face 1020 (FIG. 11), the tabs 1006' are positioned within the frame 1004 of the bone fusion device 1000'. The tabs 1006' are coupled to the frame 1004 of the bone fusion device by the one or more slots 1028 and the one or more pins 1024 wherein the one or more pins 1024 fit within the one or more slots 1028 and are able to travel along the interior of the one or more slots 1028.

Figure 14B:
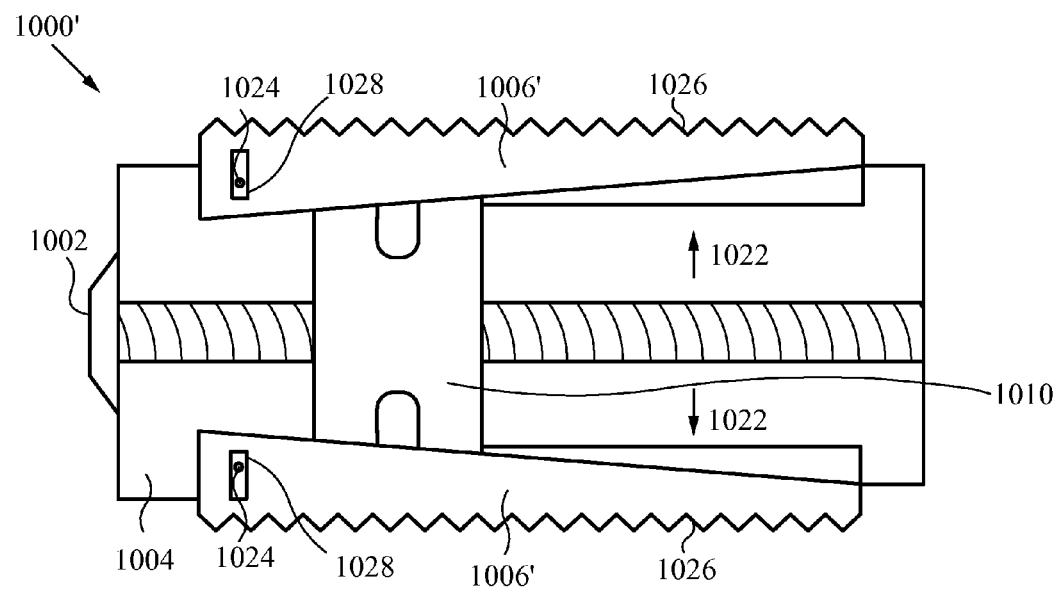
FIG. 14B illustrates a cross sectional view of the bone fusion device with the tabs extended in another embodiment of the invention.

FIG. 14B illustrates a cross sectional view of the bone fusion device 1000' with the tabs 1006' with serrated edges 1026 extended in another embodiment. When the extending block 1010 is positioned near the head of the positioning means 1002 and close to the first end face 1018 (FIG. 10), the tabs 1006' extend beyond the frame 1004 of the bone fusion device 1000' and ultimately secure the bone fusion device 1000' between two bones. The tabs 1006' extend because the extending block 1010 pushes the angled tabs 1006 outwardly as shown by the arrows 1022. The position of the extending block 1010 is changed by rotating the positioning means 1002 either clockwise or counterclockwise. The tabs 1006' are extended outward due to the force of the extending block 1010. With the tabs 1006' coupled to the frame 1004 of the bone fusion device by the one or more slots 1028 and the one or more pins 1024, the tabs 1006' are able to extend beyond the frame of the bone fusion device 1000' as the one or more pins 1024 travel within the interior of the one or more slots 1028.

Alternatively, the bone fusion device includes one or more pivots or any other rotating means that allows movement of the tabs wherein the one or more pivots are located at either end of the tabs.

To utilize the bone fusion device is some embodiments, it is initially configured in a compact position such that the extending block is located away from the head of the positioning means and towards the second end face thereby allowing the tabs to rest within the frame of the bone fusion device. The compact bone fusion device is then inserted into position within the patient. The surgeon is able to then the expand the bone fusion device by rotating the positioning means which moves the extending block towards the head of the positioning means and the first end face. As the extending block moves closer to the first end face, the tabs are pushed outwardly from the pressure of the extending block against the angled tabs. Eventually the extending block moves close enough to the first end face causing enough pressure between the extended tabs and the bones to be fused. At that point the bone fusion device is able to remain in place. Thereafter, material for fusing the bones together is inserted through the holes and openings within the bone fusion device.

Figure 15:
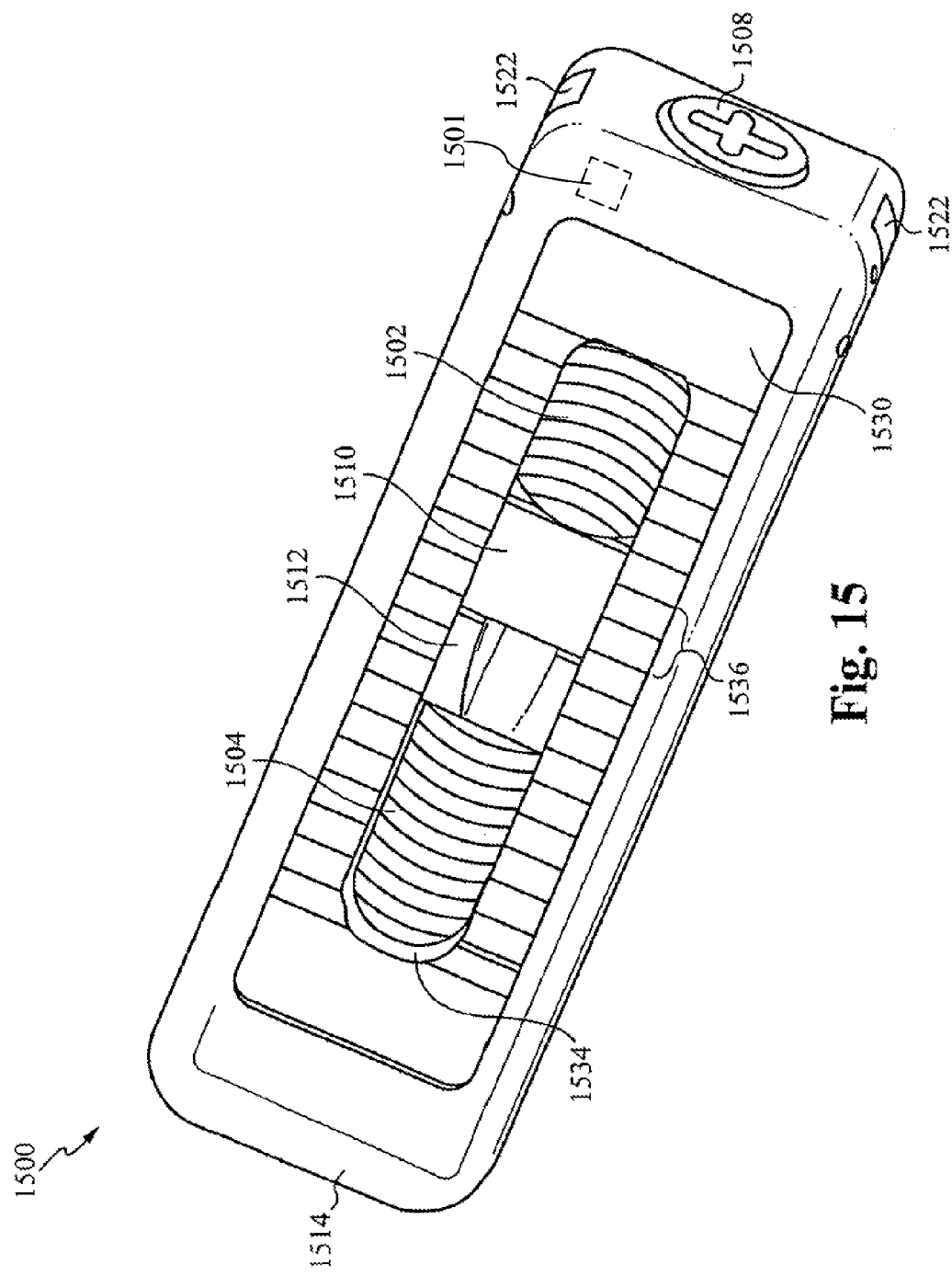
FIG. 15 illustrates a top perspective view of the bone fusion device in the preferred embodiment of the invention.

FIG. 15 illustrates a top perspective view of the bone fusion device in the preferred embodiment of the invention. As shown in this figure, the bone fusion device 1500 has a substantially rectangular shape and has two end faces. The bone fusion device 1500 is preferably constructed from a high strength biocompatible material, such as titanium, which has the strength to withstand compressive and shear forces in the spine that are generated by a patient's body weight and daily movements. The base biocompatible material is often textured or coated with a porous material conducive to the growth of new bone cells on the bone fusion device 1500. The bone fusion device 1500 has several conduits or holes 1520 (FIG. 16) and 1534 which permit the bone graft material to contact the vertebral bone after the device 1500 has been inserted between the vertebrae of the patient. The bone graft material and the surface texturing of the device 1500 encourage the growth and fusion of bone from the neighboring vertebrae. The fusion and healing process will result in the bone fusion device 1500 becoming embedded within the two adjacent vertebrae of the spine which eventually fuse together during the healing period. In some embodiments, the bone fusion device 1500 comprises a radio frequency identification (RFID) chip 1501 that uniquely identifies the bone fusion device 1500, provides information about the characteristics of the bone fusion device 1500, provides information about the patient in which the bone fusion device 1500 is implanted, provides information about the procedure used to implant the bone fusion device 1500 and/or other types of information. In some embodiments, the RFID chip 1501 is passive. Alternatively, the RFID chip 1501 is active. As a result, the bone fusion device 1500 is able to provide the benefit of enable the RFID chip 1501 to be scanned and the information contained on the chip 1501 to be accessed for beneficial use.

As further illustrated in FIG. 15, tabs 1530 are located on opposing sides of the bone fusion device 1500. The tabs 1530 are shaped so that their outer surface is substantially flush with the frame 1514 of the bone fusion device 1500 in a nonextended position. Internally, the tabs 1530 have an angled inner surface. Each tab 1530 is shaped such that the ends are larger than the middle, and the size of the tab 1530 gradually increases while going from the middle to the ends. A positioning means 1508 within the frame 1514 of the bone fusion device 1500 comprises a first screw 1502 and a second screw 1504 coupled together. The first screw 1502 is threaded opposite of the second screw 1504. For example, if the first screw 1502 is left threaded, the second screw 1504 is right threaded or visa versa. Furthermore, the first screw 1502 is of a slightly different size than the second screw 1504. The positioning means 1508 is coupled to a first extending block 1510 and a second extending block 1512. Specifically the first extending block 1510 is coupled to the first screw 1502 and the second extending block 1512 is coupled to the second screw 1504. The first extending block 1510 and the second extending block 1512 are positioned in the middle of the bone fusion device 1500 in the compact position. When the positioning means 1508 is turned appropriately, the extending blocks 1510 and 1512 each travel outwardly on their respective screws 1502 and 1504. As the extending blocks 1510 and 1512 travel outwardly, they push the tabs 1530 outward. To retract the tabs 1530, the positioning device 1508 is turned in the opposite direction and the extending blocks 1510 and 1512 will each travel back to the middle on their respective screws 1502 and 1504. When the extending blocks 1510 and 1512 are positioned in the middle of the bone fusion device 1500, the tabs 1530 are compact and are within the frame 1514 of the bone fusion device 1500. Thus, the nonextended tabs 1530 of the bone fusion device 1500 provide a compact assembly that is suitable for insertion into the patient's body through an arthroscopic surgical procedure. An arthroscopic procedure is considered minimally invasive and has certain advantages over more invasive conventional surgical procedures. In an arthroscopic procedure, a smaller surgical incision is employed as compared to the size of the incision required for conventional invasive surgery. Moreover, arthroscopic procedures minimize or eliminate the need for excessive retraction of a patient's tissues such as muscles and nerves, thereby minimizing trauma and injury to the muscles and nerves and further reducing the patient's recovery time.

As the positioning means 1508 is rotated causing the extending blocks 1510 and 1512 to move closer to the ends of the respective screws 1502 and 1504, the extending blocks 1510 and 1512 push the tabs 1530 outward causing the tabs 1530 to assert pressure against surrounding bones and securing the bone fusion device 1500 in place. When the extending blocks 1510 and 1512 reach as close to the head of the positioning means 1508 as allowed, the tabs 1530 are fully extended. Furthermore, since the extending blocks 1510 and 1512 travel along the positioning means 1508, along the threads of the screws 1502 and 1504, very precise positions of the tabs 1530 are able to be achieved. The tabs 1530 have serrated edges 1536 to further increase the bone fusion device's gripping ability to secure it in place between the bones.

To secure the bone fusion device 1500 in place, a user generally utilizes an implement such as a screw driver to turn the positioning means 1508. Screw drivers unfortunately have the ability to slip out of place. When performing surgery near someone's spine, it is preferable to prevent or at least minimize the slipping ability. To do so, channels 1522 are implemented to receive a tool (not shown). The tool (not shown) has attachments that fit within the channels 1522 to secure the tool (not shown) in place.

Figure 16:
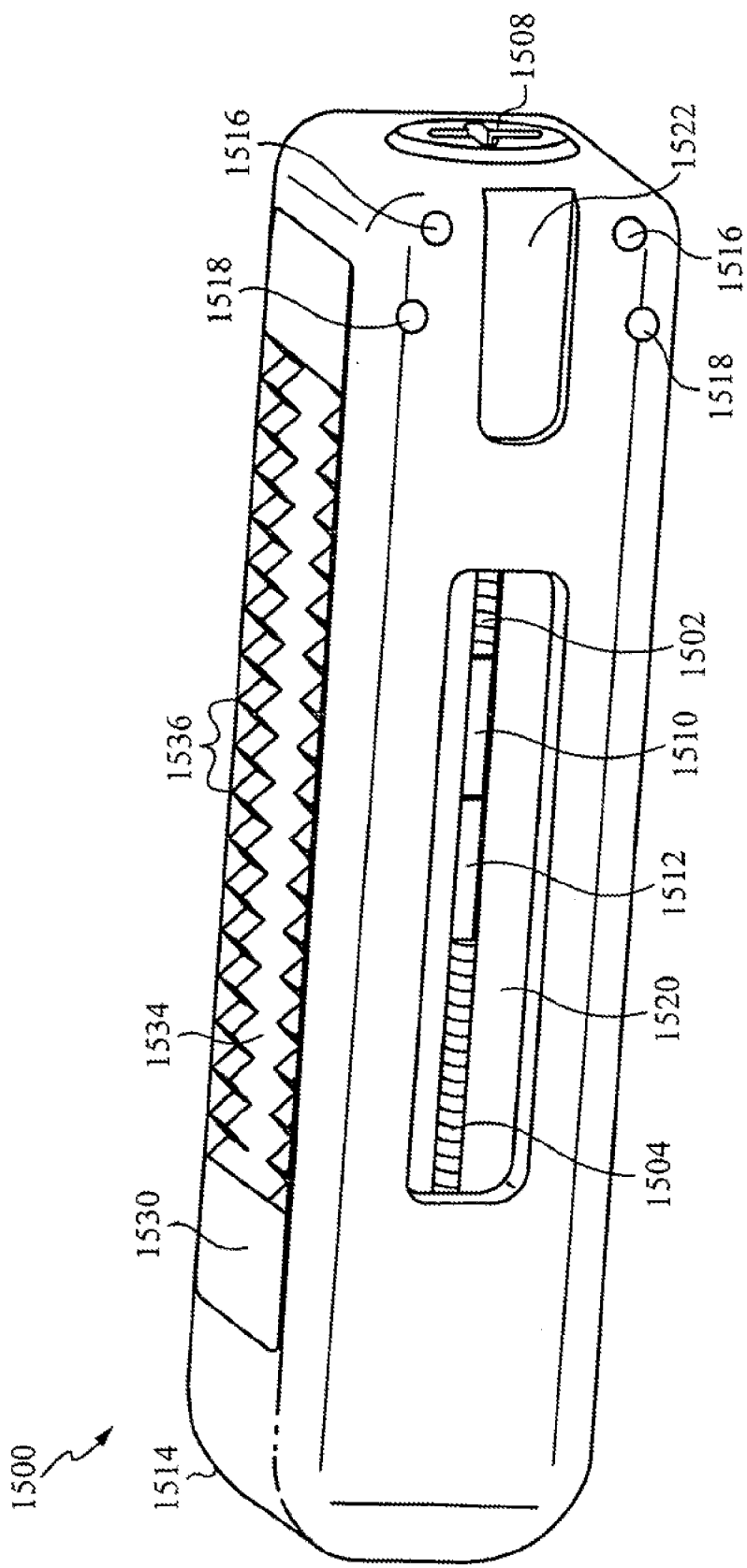
FIG. 16 illustrates a side perspective view of the bone fusion device in the preferred embodiment of the present invention.

FIG. 16 illustrates a side perspective view of the bone fusion device in the preferred embodiment of the present invention. The bone fusion device 1500 utilizes the positioning means 1508 comprising the first screw 1502 and the second screw 1504 to move the first extending block 1510 and the second extending block 1512 outwardly from the middle of the bone fusion device 1500 towards its ends. The positioning means 1508 is held in place but permitted to turn utilizing one or more first pins 1516. The one or more first pins 1516 are secured within a retaining groove 1506 (FIG. 17) of the positioning means 1508. The extending blocks 1510 and 1512 force the tabs 1530 to either extend or retract depending on where the extending blocks 1510 and 1512 are positioned. As described above, the tabs 1530 have serrated edges 1536 to further increase gripping ability. The tabs 1530 are each coupled to the frame 1514 of the bone fusion device 1500 by one or more slots 1532 (FIG. 18A) and one or more second pins 1518 wherein the one or more second pins 1518 fit within the one or more slots 1532 and are able to travel along the interior of the one or more slots 1532. The holes 1534 within the tabs 1530 allow the bone graft material to contact the vertebral bone after the device 1500 has been inserted between the vertebrae of the patient. A set of holes 1520 within the frame 1514 also allow bone graft material to be inserted within the bone fusion device 1500 after the bone fusion device 1500 has been placed. The channels 1522 implemented to receive a tool are shown as well.

Figure 17:
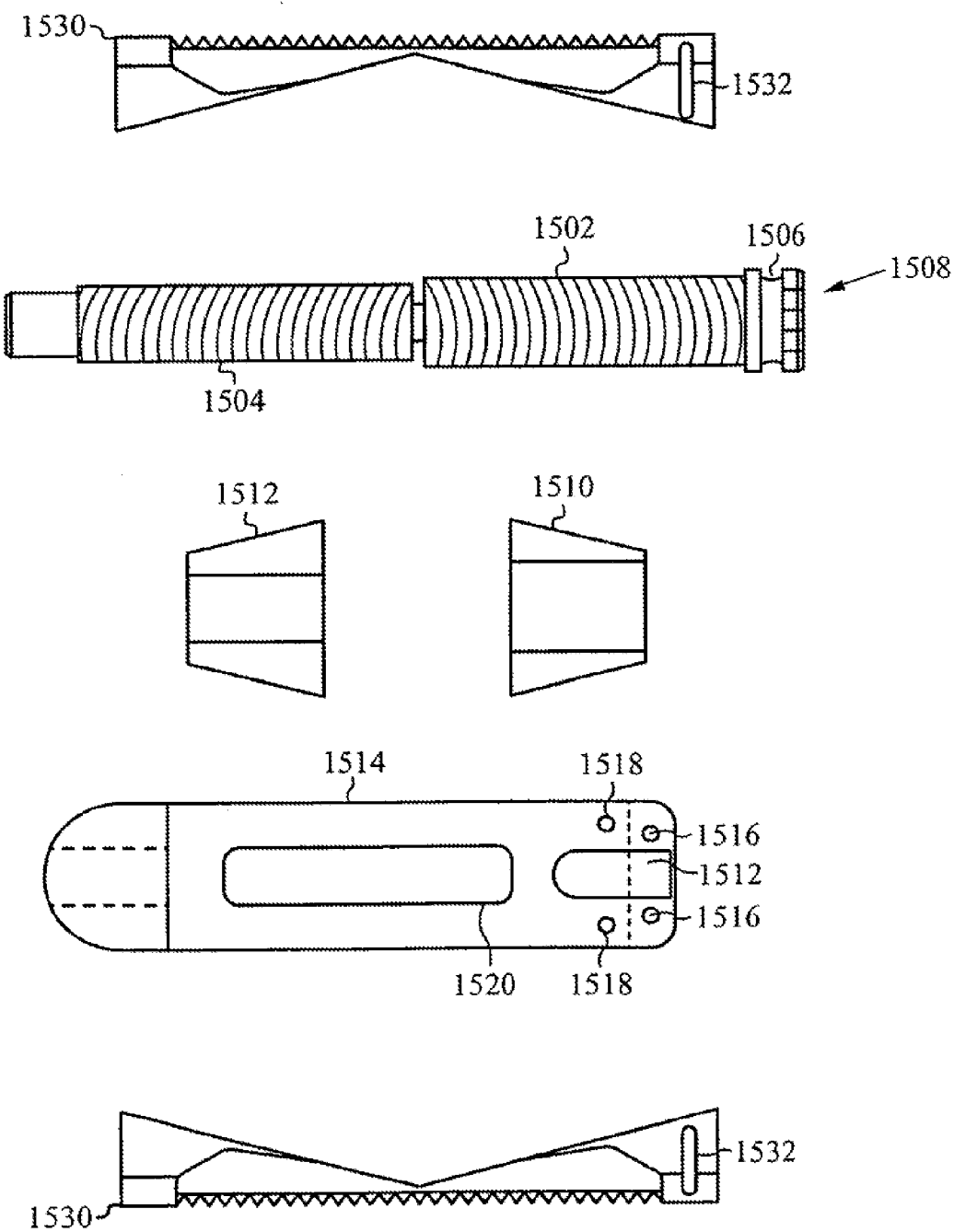
FIG. 17 illustrates a cross-sectional view of components of the bone fusion device in the preferred embodiment of the present invention.

FIG. 17 illustrates a cross-sectional view of components of the bone fusion device in the preferred embodiment of the present invention. As described above, the positioning means 1508 comprises a first screw 1502 and a second screw 1504 wherein the first screw 1502 is threaded differently than that of the second screw 1504. Furthermore, the first screw 1502 is of a slightly different size than the second screw 1504. For example, the first screw 1502 is an 8-32 screw and the second screw is a 6-32 screw. A retaining groove 1506 is utilized to secure the positioning means 1508 in place. To ensure that a device (not shown) does not slip while turning the positioning means 1508, channels 1522 are utilized to secure the device. A first extending block 1510 and a second extending block 1512 are utilized with the positioning means 1508 to extend and compact a plurality of tabs 1530. The first extending block 1510 has an internal opening to fit around the first screw 1502. The second extending block 1512 has an internal opening to fit around the second screw 1504. The frame 1514 of the bone fusion device 1500 contains a set of holes 1520 within the frame 1514 for allowing bone graft material to be inserted. Furthermore, one or more first pins 1516 secure the positioning means within the frame 1514. One or more second pins 1516 in conjunction with one or more slots 1532 secure the tabs 1530 to the frame 1514.

Figure 18A:
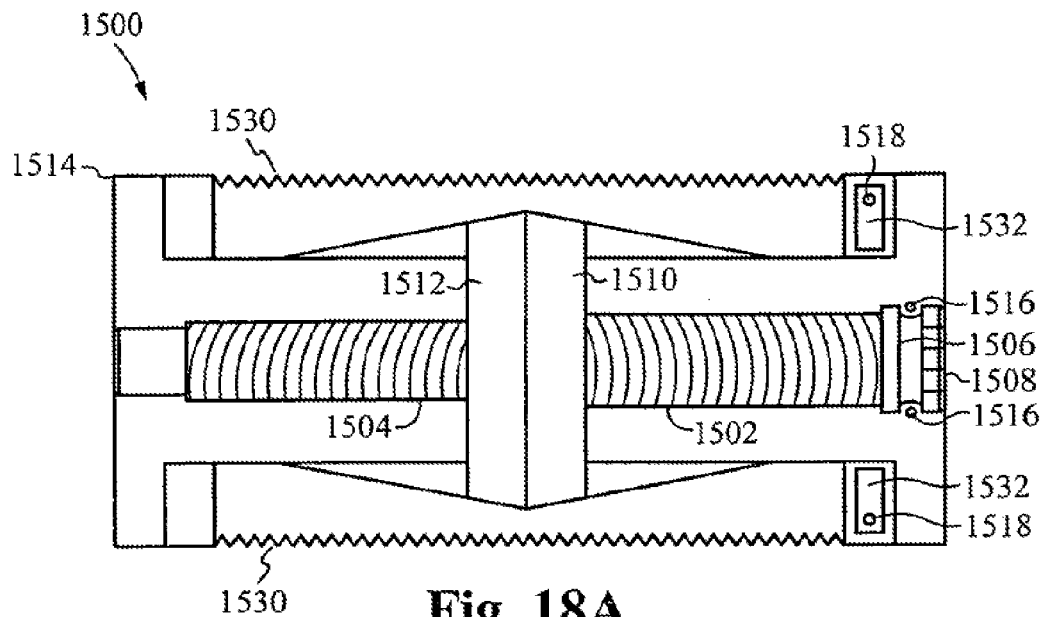
FIG. 18A illustrates a cross sectional view of the bone fusion device with the tabs compacted in the preferred embodiment of the invention.

FIG. 18A illustrates a cross sectional view of the bone fusion device with the tabs compacted in the preferred embodiment of the invention. When the extending blocks 1510 and 1512 are positioned in the middle of the positioning means 1508 with the first screw 1502 and the second screw 1504, the tabs 1530 are positioned within the frame 1514 of the bone fusion device 1500. The positioning means 1508 contains a retaining groove 1506 for holding the positioning means 1508 in place with one or more first pins 1516. The tabs 1530 are coupled to the frame 1514 of the bone fusion device 1500 using the one or more slots 1532 and the one or more second pins 1518 wherein the one or more second pins 1518 fit within the one or more slots 1532 and are able to travel along the interior of the one or more slots 1532.

Figure 18B:
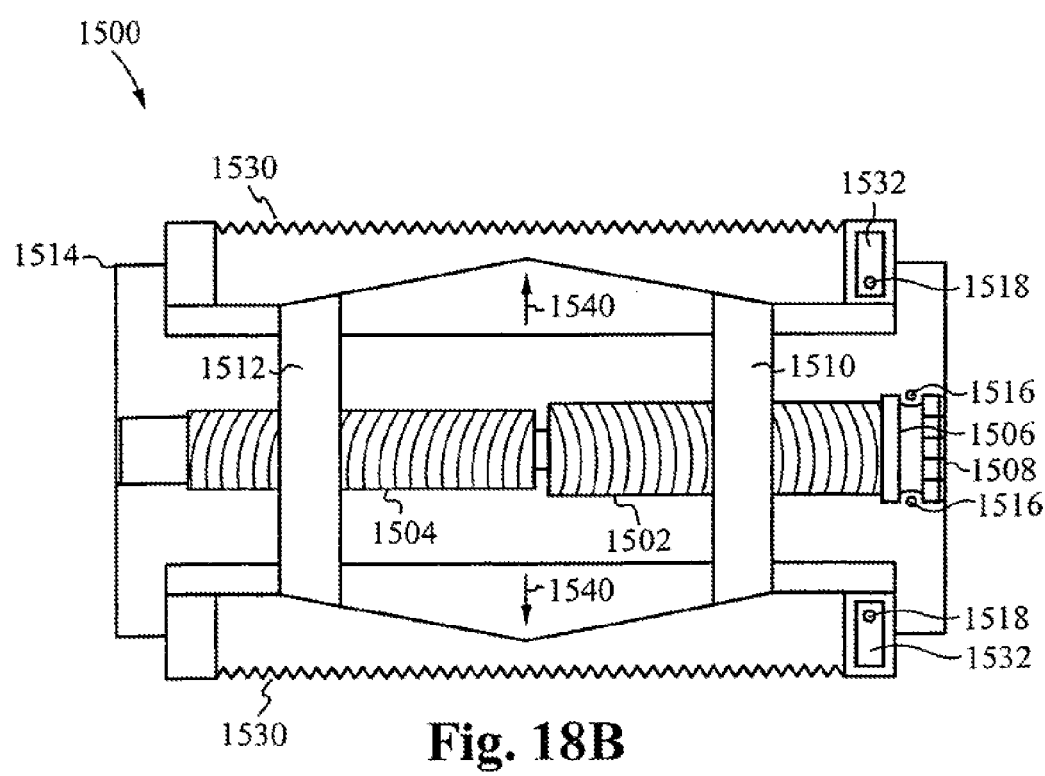
FIG. 18B illustrates a cross sectional view of the bone fusion device with the tabs extended in the preferred embodiment of the invention.

FIG. 18B illustrates a cross sectional view of the bone fusion device with the tabs extended in the preferred embodiment of the invention. As shown in FIG. 18A, the bone fusion device 1500 is compressed when the extending blocks 1510 and 1512 are in the middle of the bone fusion device 1500. As a user turns the positioning means 1508, the extending blocks 1510 and 1512 gradually move outward from the middle. If the user turns the positioning means 1508 in the opposite direction, the extending blocks move back towards the middle. As the extending blocks 1510 and 1512 are moving outward, they push on the tabs 1530. The tabs 1530 extend because the extending blocks 1510 and 1512 exert force the angled tabs 1530 outwardly as shown by the arrows 1540. When the extending blocks 1510 and 1512 are positioned near the ends of the bone fusion device 1500, the tabs 1530 extend beyond the frame 1514 of the bone fusion device 1500 and ultimately secure the bone fusion device 1500 between two bones. With the tabs 1530 coupled to the frame 1514 of the bone fusion device 1500 by the one or more slots 1532 and the one or more second pins 1518, the tabs 1530 are able to extend beyond the frame 1514 of the bone fusion device 1500 as the one or more second pins 1518 travel within the interior of the one or more slots 1532.

To utilize the bone fusion device in the preferred embodiment, it is initially configured in a compact position such that the extending blocks are located in the middle of the bone fusion device thereby allowing the tabs to rest within the frame of the bone fusion device. The compact bone fusion device is then inserted into position within the patient. The surgeon is able to then the expand the bone fusion device by rotating the positioning means which moves the extending blocks towards the opposing ends of the bone fusion device— one near the head of the positioning means and the other towards the tail of the positioning means. As the extending blocks move away from the middle, the tabs are pushed outwardly from the pressure of the extending block against the angled tabs. Eventually the extending blocks exert a satisfactory force between the extended tabs and the bones to be fused. At that point the bone fusion device is able to remain in place. Thereafter, material for fusing the bones together is inserted through the holes and openings within the bone fusion device.

Figure 19:
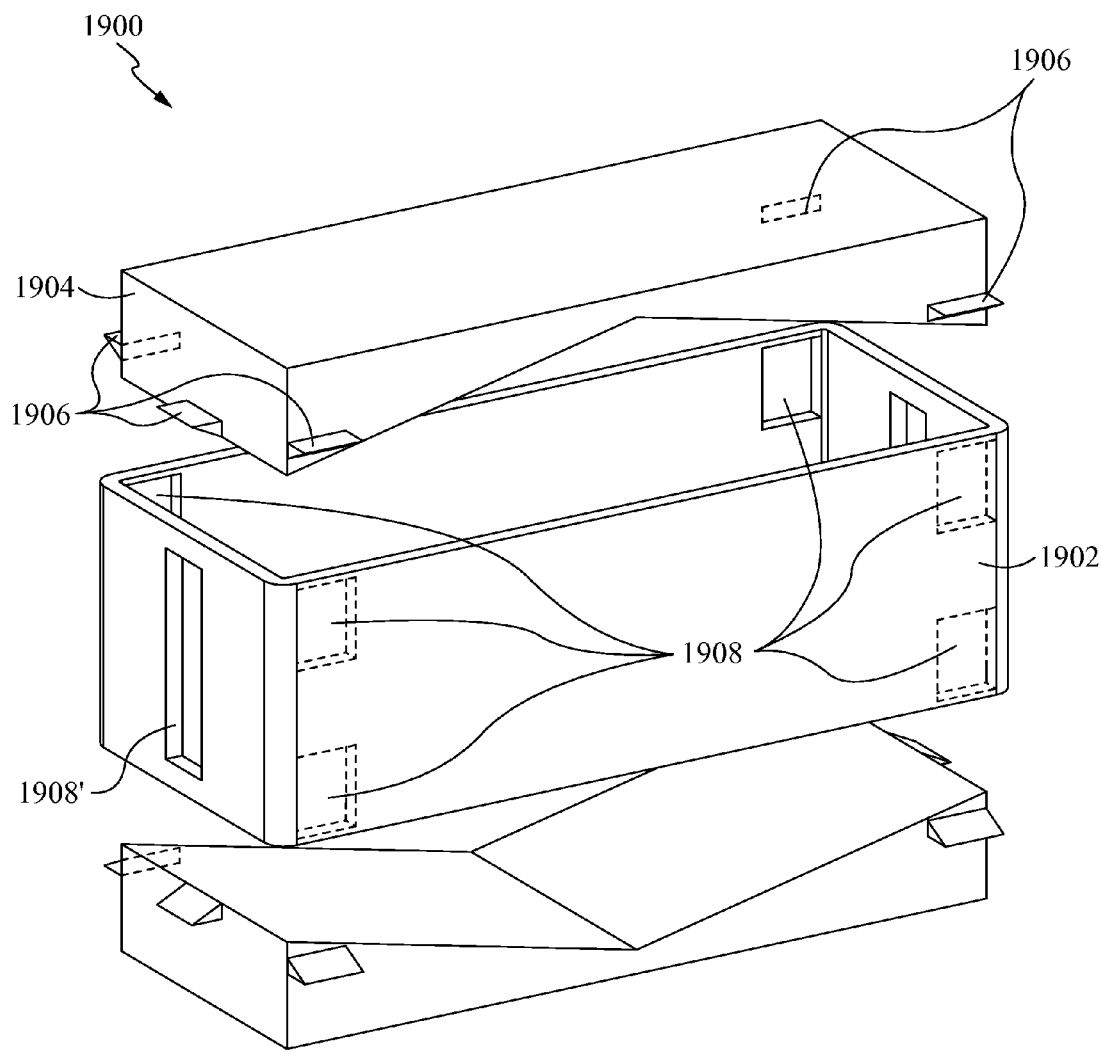
FIG. 19 illustrates a perspective view of a bone fusion device having one or more stops according to some embodiments.

FIG. 19 illustrates a perspective view of a bone fusion device 1900 having one or more stops according to some embodiments. The bone fusion device 1900 shown in FIG. 19 is substantially similar to the bone fusion device 1500 except for the differences described herein. Specifically, instead of the pin and slot system of the bone fusion device 1500, the bone fusion device 1900 comprises a body 1902 having one or more recesses 1908 and one or more tabs 1904 having one or more stops 1906. As shown in FIG. 19, the tabs 1904 each comprise five stops 1906 positioned along the bottom perimeter of the tabs 1904. However, it is understood that the tabs 1904 are each able to comprise any number of stops 1906 positioned anywhere along the perimeter of the tabs 1904. The recesses 1908 are sized and positioned within the body 1902 such that the recesses 1908 are each able to receive at least one of the stops 1906 when the tabs 1904 are inserted into the body 1902. In particular, once within the recesses 1908, the stops 1906 are able to slide up and down the recesses 1908 as the tabs 1904 are extended out and retracted within the body 1902. In this way, the recesses 1908 are able to be configured to block the outward/extension movement of the stops 1906 at a desired maximum extension point thereby preventing the tabs 1904 from extending beyond the maximum extension point and/or falling out of the body 1902. In some embodiments, each stop 1906 has a separate associated recess 1908 such that there is one recess 1908 for each stop 1906. Alternatively, as shown in FIG. 19, one or more of the stops 1906 are able to share a single recess 1908'.

Figure 20:
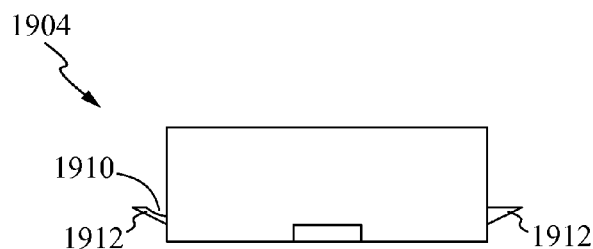
FIG. 20 illustrates a frontal view of a tab having one or more stops according to some embodiments.

FIG. 20 illustrates a frontal view of a tab 1904 having one or more stops 1906 according to some embodiments. Specifically, as shown in FIG. 20, the stops 1906 comprise a stop outer surface 1912 that is angled with respect to the surface of the perimeter of the tab 1904 such that the lower portion of the stop 1906 is closer to the perimeter of the tab 1904 than the upper portion of the stop 1906. As a result, the stop outer surface 1912 is able to facilitate the insertion of the tabs 1904 into the body 1902 by causing the tab 1904 to compress when entering the opening of the body 1902 and then decompress as the stops 1906 slide into the recesses 1908 within the body 1902. In some embodiments, one or more of the stops 1906 comprise a stop channel 1910 than enables the stops 1906 to flex inwardly when the tab 1904 is inserted into the body 1904 and spring back into place when the stops 1906 align with the recesses 1908. Additionally, in some embodiments the stop channel 1910 is able to be sized to receive a retention spring 2106 (see FIG. 21) in order to facilitate the coupling of the tab 1904 with the retention spring 2106. In such embodiments, the stops 1906 are able to replace or supplement the tab protrusions 2108. Accordingly, the bone fusion device 1900 provides the advantage of better securing the tabs 1904 within the body 1902 of the device 1900. Also, it is understood that the differences to the bone fusion device 1900 described in FIGS. 19 and 20 are able to be incorporated with and/or replace components of each of the other bone fusion devices described herein.

Figure 21A:
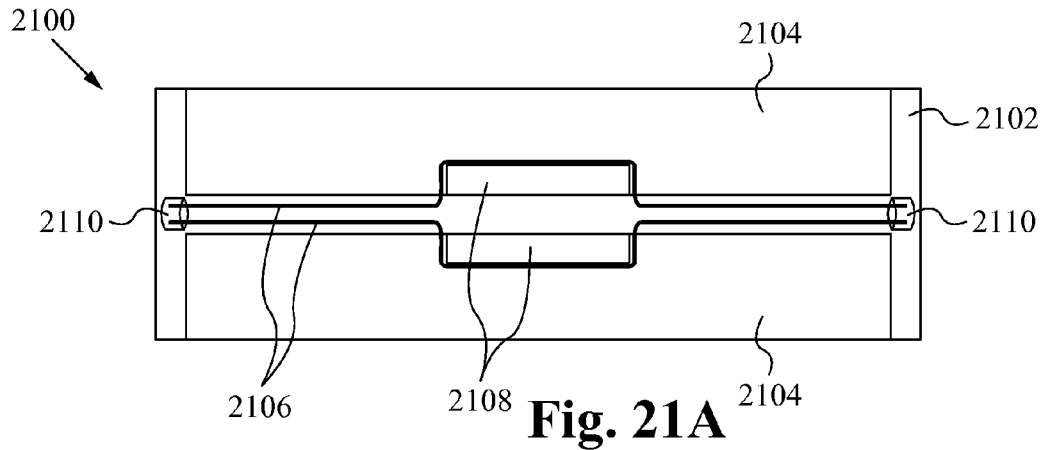
FIG. 21A illustrates a side cross-sectional view of a contracted bone fusion device having one or more retention springs according to some embodiments.
Figure 21B:
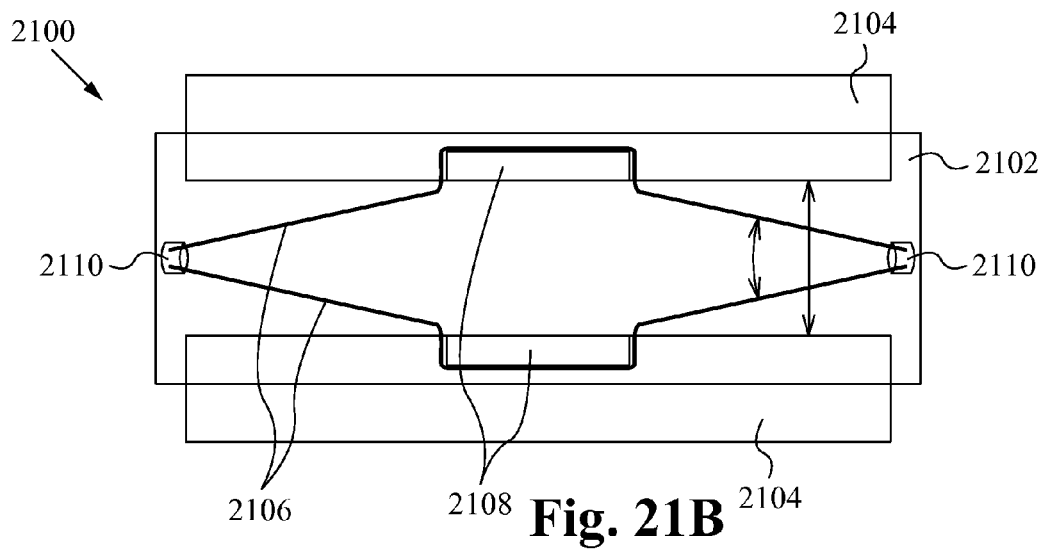
FIG. 21B illustrates a side cross-sectional view of an extended bone fusion device having one or more retention springs according to some embodiments.

FIGS. 21A-21J illustrate views of a bone fusion device 2100 having one or more retention springs according to some embodiments. The bone fusion device 2100 shown in FIGS. 21A-21J is substantially similar to the bone fusion device 1500 except for the differences described herein. Further, it is understood that although FIGS. 21A-21J illustrate a number of tabs and retention springs, any number of tabs and retention springs are contemplated. FIGS. 21A and 21B illustrate side cross-sectional views of a bone fusion device 2100 having tabs in the contracted and extended positions, respectively. As shown in FIGS. 21A and 21B the bone fusion device 2100 comprises a body 2102 having one or more spring receptors 2110, one or more tabs 2104 having tab protrusions 2108 and one or more retention springs 2106. In some embodiments, the retention springs 2106 comprise a wire such as a nitinol wire. Alternatively, the retention springs 2106 are able to comprises other dimensions and/or materials as are well known in the art. In some embodiments, the device 2100 comprises at least one retention spring 2106 for each tab 2104. Alternatively, a single retention spring 2106 is able to contact and/or be coupled to multiple tabs 2104. The ends of the retention springs 2106 are positioned and/or coupled within the spring receptors 2110 such that the ends of the retention springs 2106 do not move with respect to the body 2102. The middle of the retention springs 2106 is coupled to and/or positioned such that it blocks the outward movement of the tab protrusions 2108 of each of the tabs 2104 in order to resist the movement of the tabs 2104 into the extended position. As shown in FIG. 21B, when a user causes the tabs 2104 and their corresponding tab protrusions 2108 move/extend out of the body 2102, the protrusions 2108 cause the retention springs 2106 to flex. As a result, the resistance to this flexure by the retention springs 2106 biases the tabs 2104 toward the retracted position such that when the user retracts the tabs 2104 they do not get stuck in the extended position. Thus, the bone fusion device 2100 provides the benefit of ensuring that the tabs 2104 retract properly when retracted from an extended position.

Figure 21C:
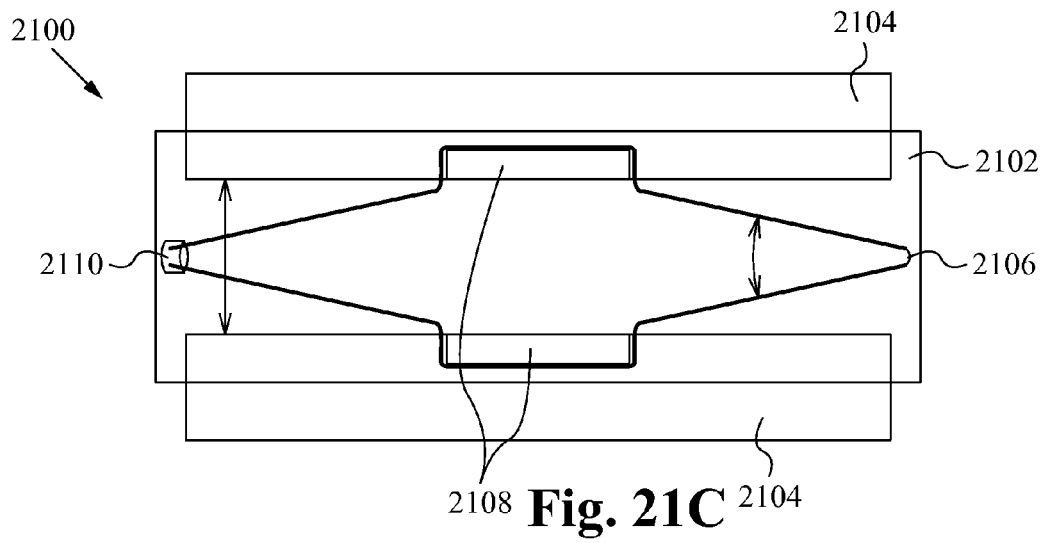
FIG. 21C illustrates a side cross-sectional view of an extended bone fusion device having one or more retention springs according to some embodiments.
Figure 21D:
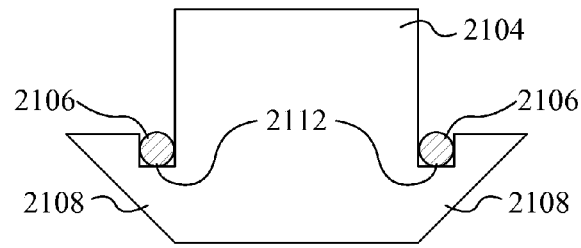
FIG. 21D illustrates a front cross-sectional view of a tab of a bone fusion device having one or more retention springs according to some embodiments.
Figure 21E:
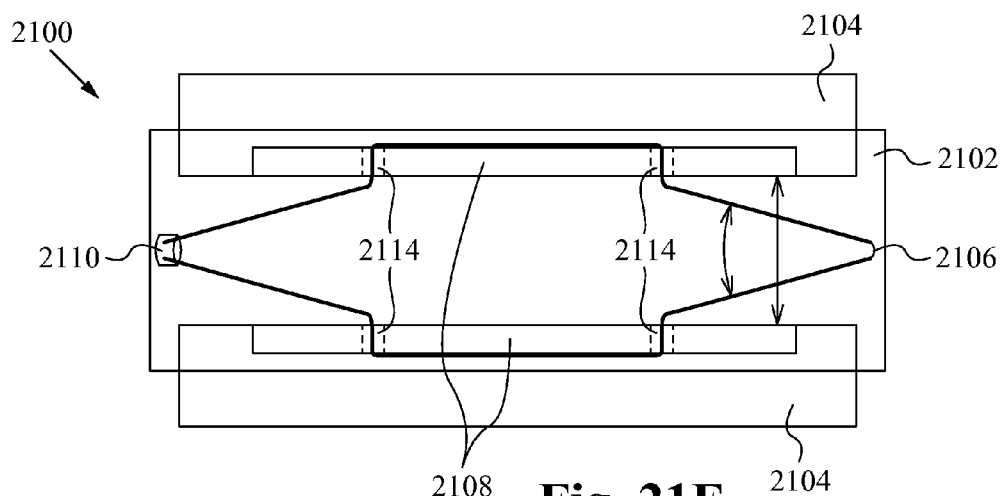
FIG. 21E illustrates a side cross-sectional view of an extended bone fusion device having one or more retention springs according to some embodiments.

As shown FIGS. 21A and 21B, the each retention spring 2106 is coupled/associated with a single tab 2104 and/or tab protrusion 2108. Alternatively, as shown in FIG. 21C, the bone fusion device 2100 is able to comprise a single continuous retention spring 2106 that couples with multiple tabs 2104 and/or tab protrusions 2108. In some embodiments, as shown in FIG. 21D, the tab protrusions 2108 each comprise a protrusion channel 2112 that is configured for receiving the retention springs 2106. As a result, the channels 2112 are able to ensure that the retention springs 2106 do not slip off of the protrusions 2108 during operation. In some embodiments, as shown in FIG. 21E, the tab protrusions 2108 comprise one or more protrusion apertures 2114 that are configured to receive the retention springs 2106. As a result, the protrusion apertures 2114 enable the retention springs 2106 to be secured to the tab protrusions 2108.

Figure 21F:
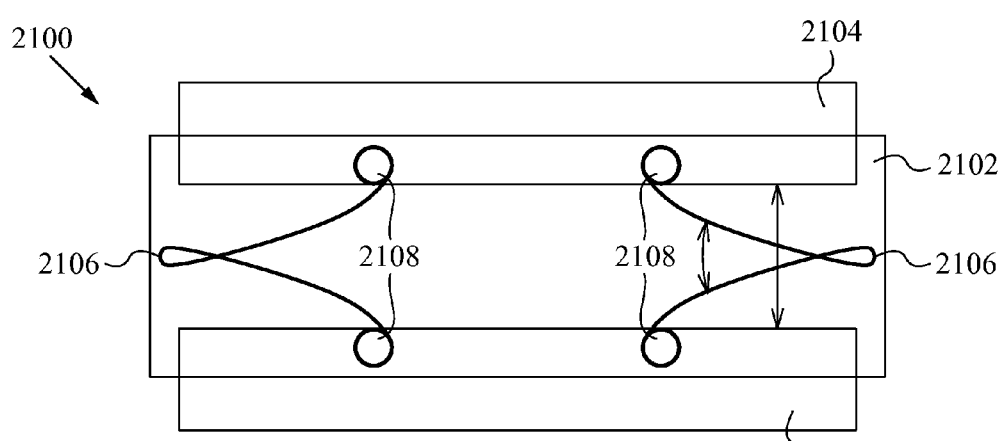
FIG. 21F illustrates a side cross-sectional view of an extended bone fusion device having one or more retention springs according to some embodiments.

FIG. 21F illustrates a side cross-sectional view of the bone fusion device 2100 having one or more retention springs according to some embodiments. As shown in FIG. 21F, instead of coupling between the body 2102 of the device 2100 and the tab protrusions 2108, the retention springs 2106 of FIG. 21F are coupled between a tab protrusion 2108 of a first tab 2104 and the tab protrusion 2108 of a second tab 2104. As a result, the resistance provided by the retention springs 2106 in order to bias the tabs 2104 into the retracted position is able to be increased as the retention springs 2106 are flexed in both directions by the oppositely moving tabs 2104.

Figure 21G:
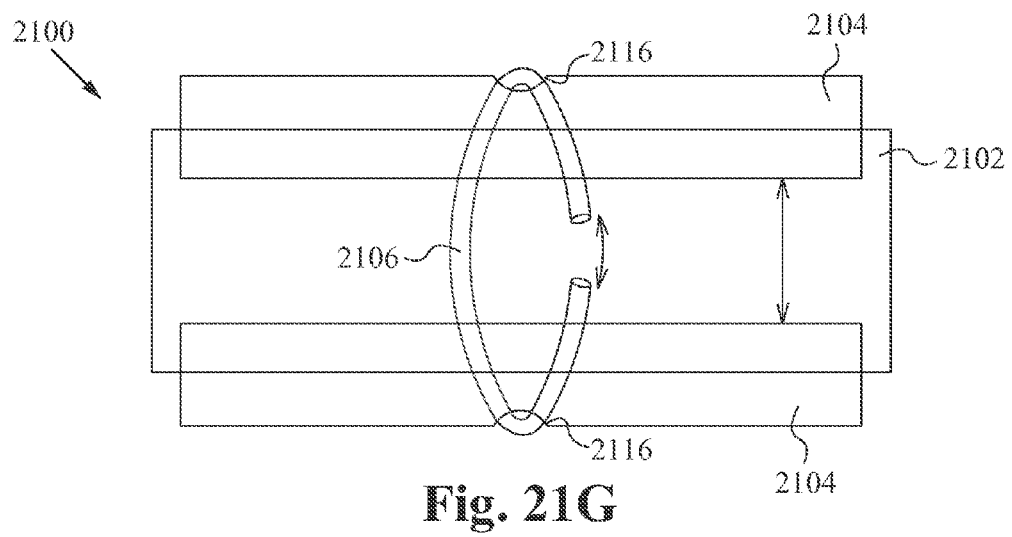
FIG. 21G illustrates a side cross-sectional view of an extended bone fusion device having one or more retention springs according to some embodiments.

FIG. 21G illustrates a side cross-sectional view of the bone fusion device 2100 having one or more retention springs according to some embodiments. As shown in FIG. 21G, instead of tab protrusions 2108 and/or spring receptors 2110, the bone fusion device 2100 comprises tabs 2104 having tab channels 2116 and one or more ring or looped retention springs 2106. Specifically, the ring or looped retention springs 2106 are able to be wrapped around the tabs 2104 one or more times in order to bias the tabs 2104 in the retracted position. Further, the tab channels 2116 are able to be configured to receive at least a portion of the ring or looped retention springs 2106 in order to prevent the springs 2106 from sliding off and/or moving with respect to the tab 2104. Although a single ring or looped retention spring 2106 looped around the tabs 2104 once is shown in FIG. 21G, any number of retention springs 2106 looped any number of times is contemplated.

Figure 21H:
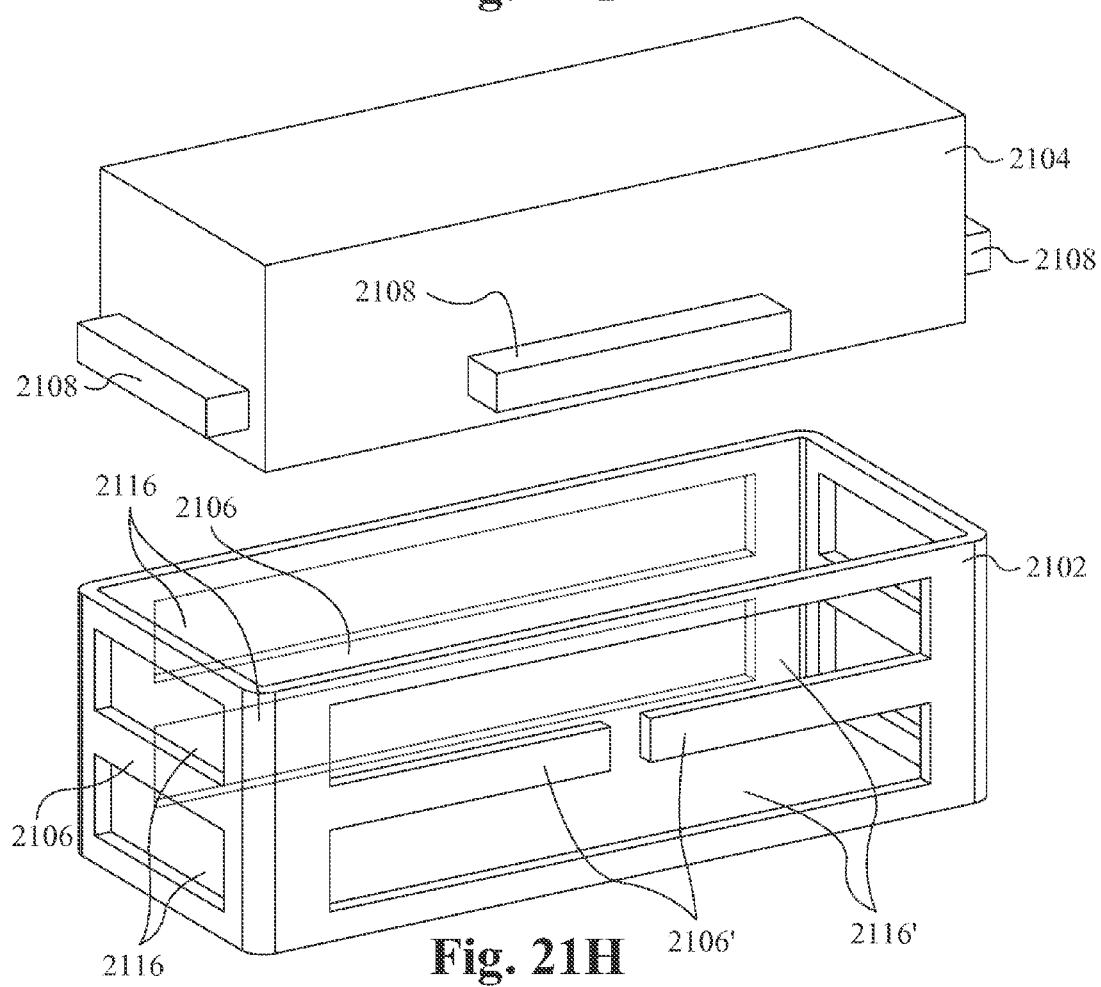
FIG. 21H illustrates a perspective view of a bone fusion device having one or more retention springs according to some embodiments.
Figure 21I:
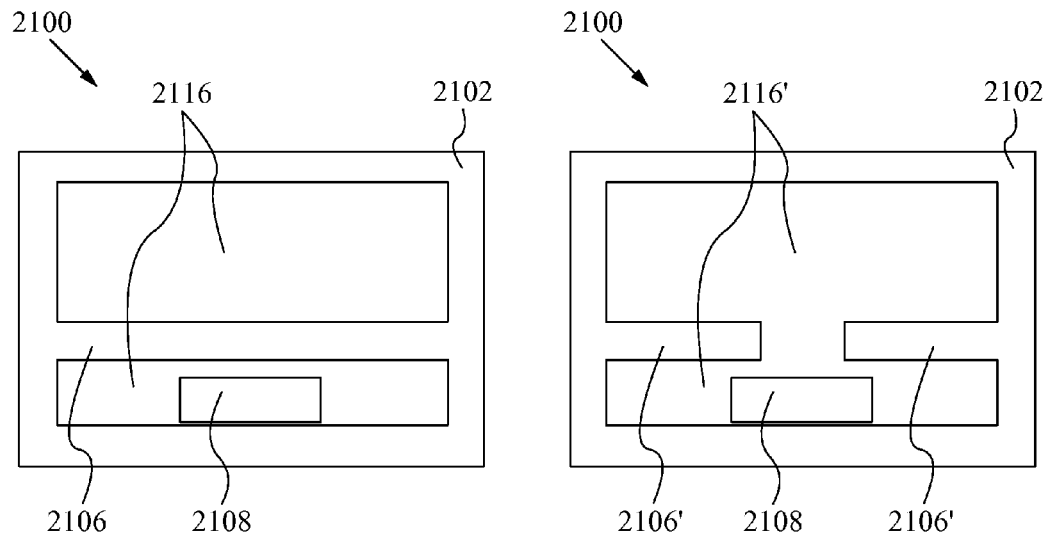
FIG. 21I illustrates a cross-sectional view of a retracted bone fusion device having one or more retention springs according to some embodiments.
Figure 21J:
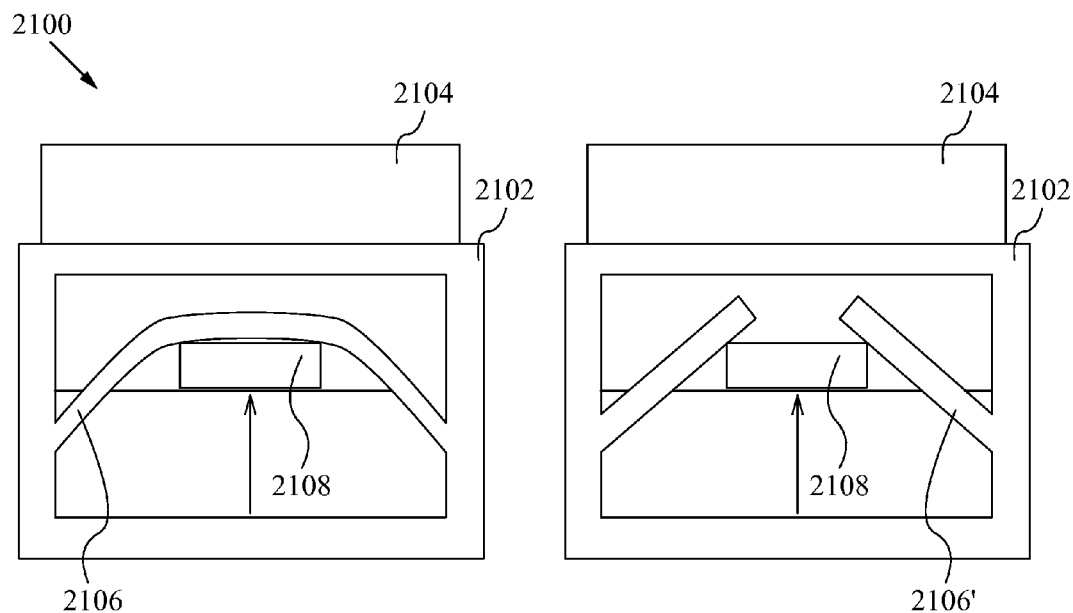
FIG. 21J illustrates a cross-sectional view of an extended bone fusion device having one or more retention springs according to some embodiments.

FIG. 21H illustrates a perspective view and FIGS. 21I and 21J illustrate cross-sectional side views of the bone fusion device 2100 wherein the retention springs are incorporated into the body according to some embodiments. As shown in FIGS. 21H-21J, the body 2102 comprises a plurality of wall cavities 2116, 2116' wherein the retention springs 2106, 2106' are coupled to the body 2102 and positioned within the wall cavities 2116, 2116'. Specifically, the tab protrusions 2108 are configured to fit within the wall cavities 2116, 2116' below the retention springs 2106, 2106' such that, as shown in FIGS. 21I and 21J, when a user moves the tabs 2104 into an extended position, the retention springs 2106, 2106' are flexed within the wall cavities 2116, 2116' causing the springs 2106, 2106' to apply an opposite biasing force. This biasing force ensures that the tabs 2104 properly retract when a user manipulates the bone fusion device 2100 in order to retract the tabs 2104. In some embodiments, the retention springs 2106 are continuous such that the retention spring 2106 continues from a connection to the body 2102 on one side of the cavity 2116 to a connection to the body 2102 on the opposite side of the cavity 2116. Alternatively, one or more of the retention springs 2106' are able to be discontinuous such that two or more separate retention springs 2106' couple to the opposite sides of the cavity 2116' of the body 2102 and meet approximately in the middle of the cavity 2116'. In either case, the retention springs 2106, 2106' are configured, positioned and coupled within the cavities 2116, 2116' such that they bias the tabs 2104 in the retracted position. As a result, the bone fusion device 2100 of FIGS. 21H-21J provides the advantage of ensuring the tabs 2104 are able to be properly retracted via biasing using retention springs. In some embodiments, the retention springs 2106 comprise PEEK or PEEKsil. Alternatively, the retention springs 2106 are able to comprise other bio-compatible materials with springing properties as are well known in the art. It is understood that the differences to the bone fusion device 2100 described in FIGS. 21A-21J are able to be incorporated with and/or replace components of each of the other bone fusion devices described herein.

Figure 22A:
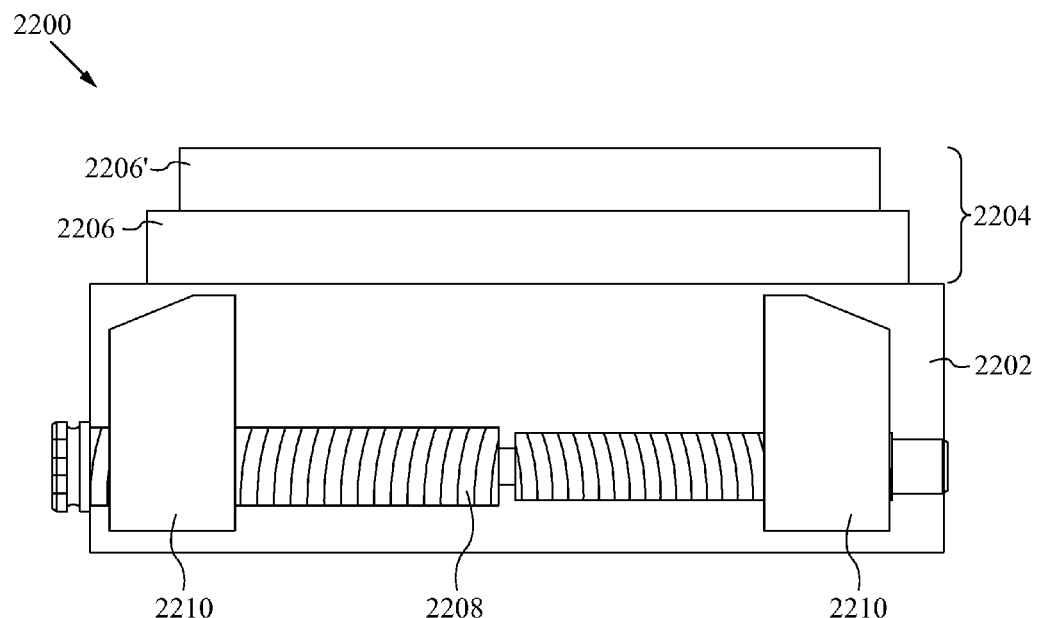
FIG. 22A illustrates a side cross-sectional view of a bone fusion device having one or more tabs with telescoping levels according to some embodiments.
Figure 22B:
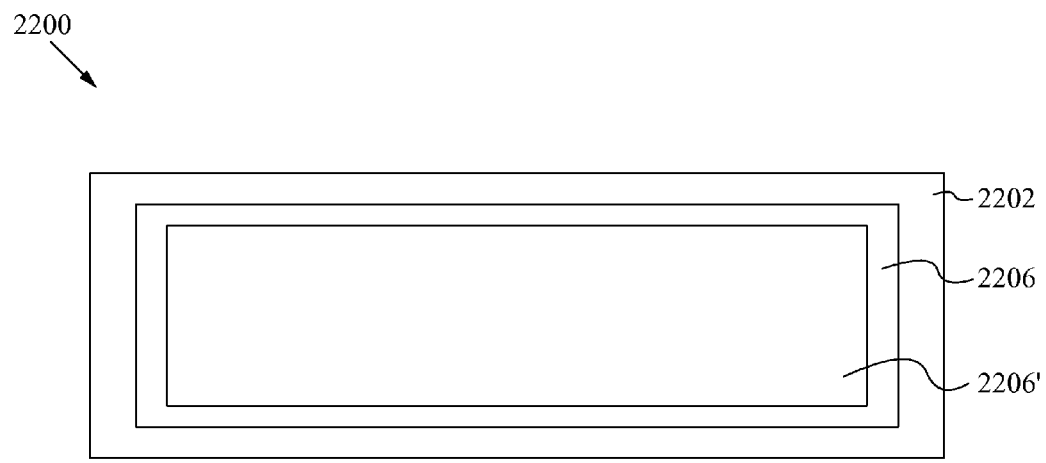
FIG. 22B illustrates a top view of a bone fusion device having one or more tabs with telescoping levels according to some embodiments.

FIGS. 22A-22G illustrate views of a bone fusion device 2200 having one or more tabs with telescoping levels according to some embodiments. The bone fusion device 2200 shown in FIGS. 22A-22G is substantially similar to the bone fusion device 1500 except for the differences described herein. Further, it is understood that although FIGS. 22A-22G illustrate a number of tabs with telescoping levels, any number of tabs with any number of telescoping levels is contemplated. FIGS. 22A-22D illustrate side, top, exploded side and bottom cross-sectional views of a bone fusion device 2200 having one or more tabs with telescoping levels according to some embodiments. As shown in FIGS. 22A-22D, the bone fusion device 2200 comprises a body 2202, one or more tabs 2204 each having a plurality of tab levels 2206, 2206', one or more positioning elements 2208 and one or more extending blocks 2210. As shown in FIG. 22B, the levels 2206, 2206' of each tab 2204 are nested such that an innermost level 2206' is surrounding by one or more outer levels 2206. Alternatively, the outer levels 2206' are able to be positioned adjacent to but not surrounding the relatively inner levels 2206, 2206'.

Figure 22C:
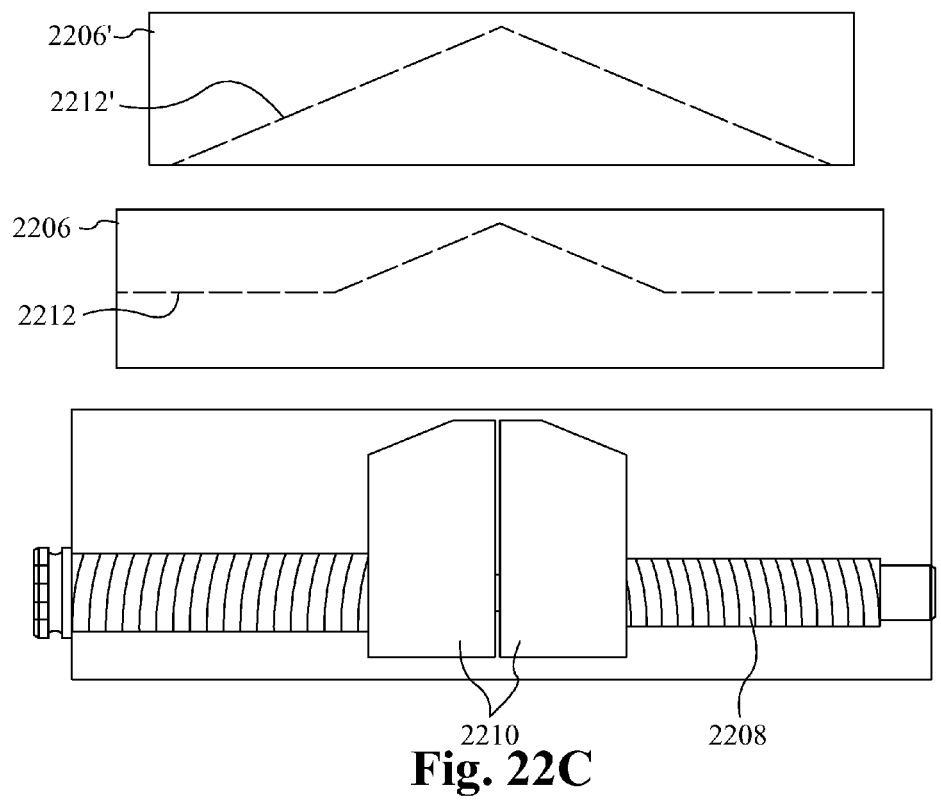
FIG. 22C illustrates an exploded side cross-sectional view of a bone fusion device having one or more tabs with telescoping levels according to some embodiments.
Figure 22D:
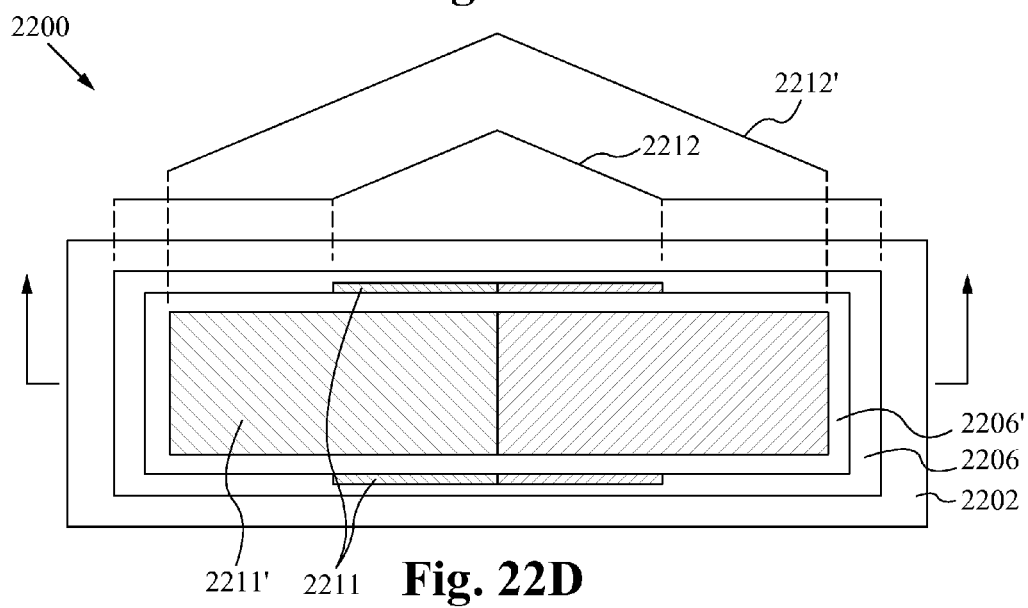
FIG. 22D illustrates a bottom cross-sectional view of a bone fusion device having one or more tabs with telescoping levels according to some embodiments.

As shown in FIGS. 22C and 22D, each of the levels 2206, 2206' have an inner surface 2211, 2211' having an inner surface profile 2212, 2212' that is contoured in a manner that controls the extension and retraction of the associated level 2206, 2206' when pushed by the extending blocks 2210. In some embodiments, as shown in FIGS. 22C and 22D, the inner surface profiles 2212, 2212' and/or the extending blocks 2210 are able to be configured such that as the extending blocks 2210 separate both the innermost and outer level 2206, 2206' simultaneously extend to a first extended height beyond which the outer level 2206 stops and the innermost level 2206' continues to extend to a second extended height. Conversely, when the extending blocks 2210 are moved closer together, the innermost level 2206' retracts from the second extended height to the first extended height beyond which both the innermost and the outer levels 2206, 2206' simultaneously retract until in the retracted position. Alternatively, the inner surface profiles 2212, 2212' and/or the extending blocks 2210 are able to be configured such that each of the innermost and outer levels 2206, 2206' move simultaneously or separately to any desired heights when the extending blocks 2210 are separated/moved together. In particular, each level 2206, 2206' is able to have a differently contoured inner surface 2211, 2211' having an inner surface profile 2212, 2212' that aligns with a differently angled and/or sized extending block surface such that the movement of each level 2206, 2206' is individually customizable. As a result, the bone fusion device 2200 provides the benefit of enabling the tab levels to extend in a telescoping or other type of extending action to various heights and at various rates as desired. This is able to be used to achieve desired extension heights as well as to provide increased lateral support to the innermost level 2206' when extended to the maximum extended position due to the support provided to the innermost level 2206' by the outer levels 2206 positioned at less than maximum extended positions.

Figure 22E:
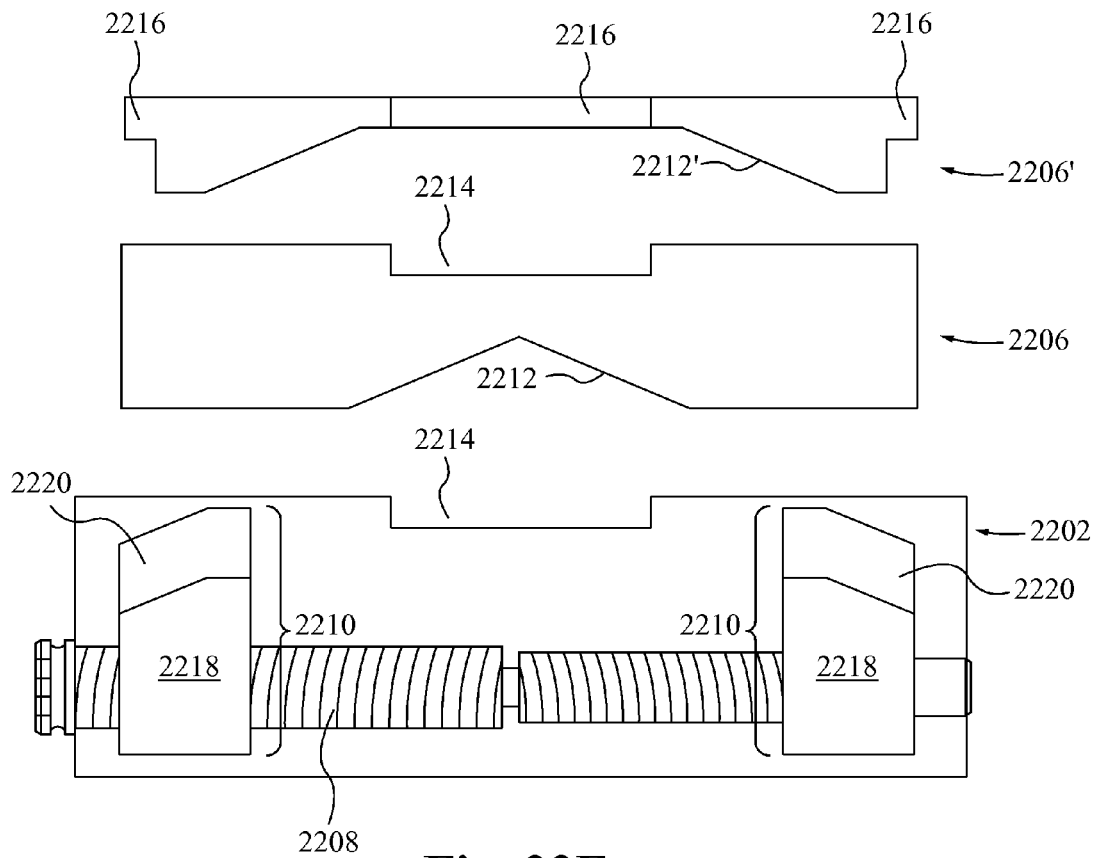
FIG. 22E illustrates a side cross-sectional view of a bone fusion device having one or more tabs with telescoping levels with tongues according to some embodiments.
Figure 22F:
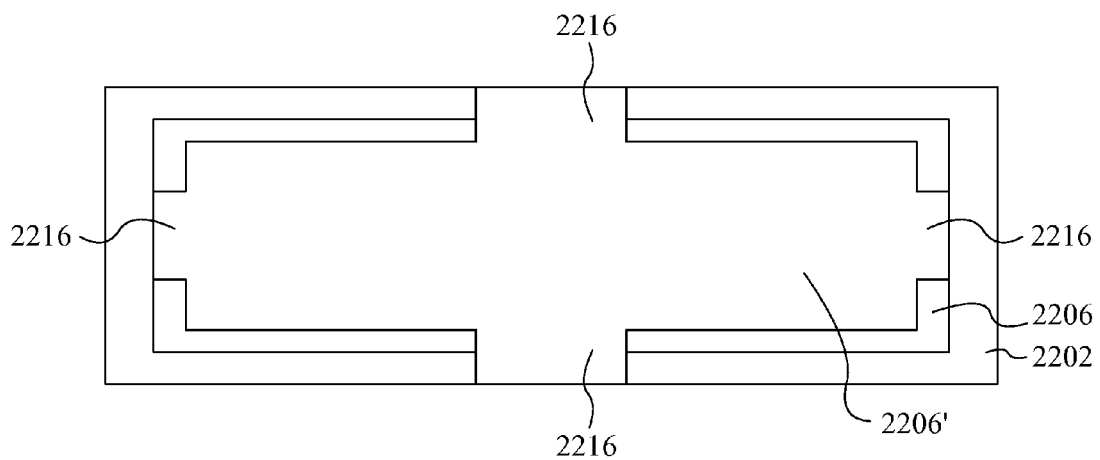
FIG. 22F illustrates a top view of a bone fusion device having one or more tabs with telescoping levels with tongues according to some embodiments.
Figure 22G:
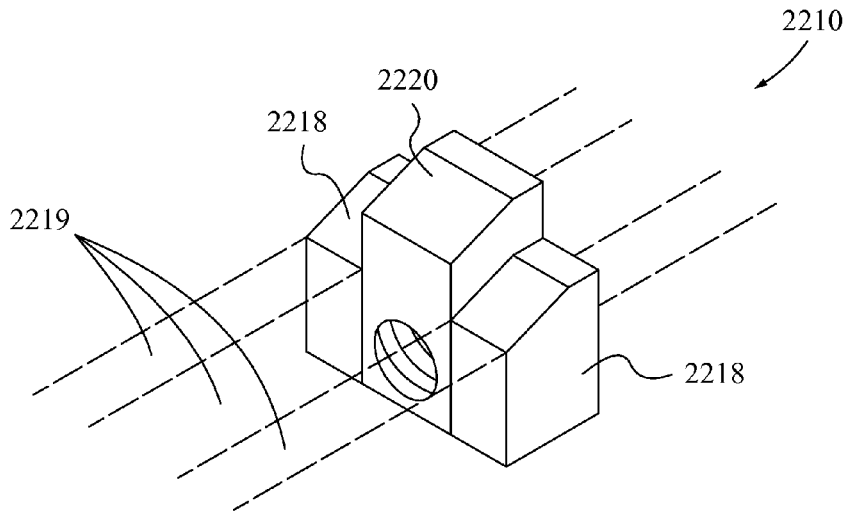
FIG. 22G illustrates a perspective view of a extending block of a bone fusion device having one or more tabs with telescoping levels according to some embodiments.

FIGS. 22E and 22F illustrate an exploded side and a top view of the bone fusion device 2200 having nested tab levels with tongues according to some embodiments. As shown in FIG. 22E, the extending blocks 2210 comprise a plurality of upper surfaces 2218, 2220 at different heights and/or angles. In particular, as shown in FIG. 22G which illustrates a perspective view of a extending block 2210 according to some embodiments, the extending block 2210 comprises a plurality of rows 2219 that each correspond to one or more of the inner surfaces 2211, 2211' of the levels 2206, 2206', wherein each row 2219 is able to have a different height and/or angle that corresponds to the corresponding inner surfaces 2211, 2211' in order to control the manner in which the levels 2206, 2206' are extended/retracted by the device 2200. In some embodiments, as shown in FIGS. 22E and 22G, the blocks 2210 are able to comprise a raised upper surface 2220 that is centered and corresponds to the profile 2212' of the innermost level 2206' and one or more lower upper surfaces 2218 that are off-center and correspond to the profile 2212 of the outer level 2206. Alternatively, as shown in FIGS. 22A and 22C above, one or more of the extending blocks 2210 are able to comprise a single row having a constant height and/or angle.

As shown in FIGS. 22E and 22F, the innermost tab level 2206' comprises one or more tongues 2216 that extend over the outer levels 2206 and/or the body 2202. Specifically, the outer levels 2206 and/or the body 2202 comprise one or more notches 2214 that are configured to receive the tongues 2216 of the innermost tab level 2206 such that in the retracted position that tongues 2216 slide within the notches 2214 in order to minimize the size of the bone fusion device 2200. Further, as a result of the tongues 2216, when the innermost level 2206' is extended further than one or more of the body 2202 and/or the outer levels 2206, the innermost level 2206' is able to obtain the benefit of an increased top surface area for contacting and fusing to the bone. Moreover, the tongues 2216 provide the benefit of enabling the extending of the outer levels 2206 to simultaneously extend the innermost level 2206' because as the outer levels 2206 are extended they push up the tongues 2216 of the innermost level 2206' thereby raising the levels 2206, 2206' simultaneously. As a result, the inner surface profile 2212' of the innermost level 2206' does not need to be configured until the outer levels 2206 have reached their most extended height. For example, as shown in FIG. 22E, the middle portion of the inner surface profile 2212 of the outer level 2206 is able to be configured to extend both the inner and outer levels 2206, 2206' and the thus only the outer portion of the inner surface profile 2212' of the innermost level 2206' needs to be configured to extend the innermost level 2206' beyond that point. As shown in FIG. 22G, the tongues 2216 and corresponding notches 2214 are able to extend over the body 2202 and all the outer levels 2206 or extend over less than the body 2202 and/or one or more of the outer levels 2206. Additionally, the tongues 2216 are able to each have different widths, lengths and heights, and be positioned anywhere along the perimeter of the innermost level 2206'. It is understood that the differences to the bone fusion device 2200 described in FIGS. 22A-22G are able to be incorporated with and/or replace components of each of the other bone fusion devices described herein.

Figure 23:
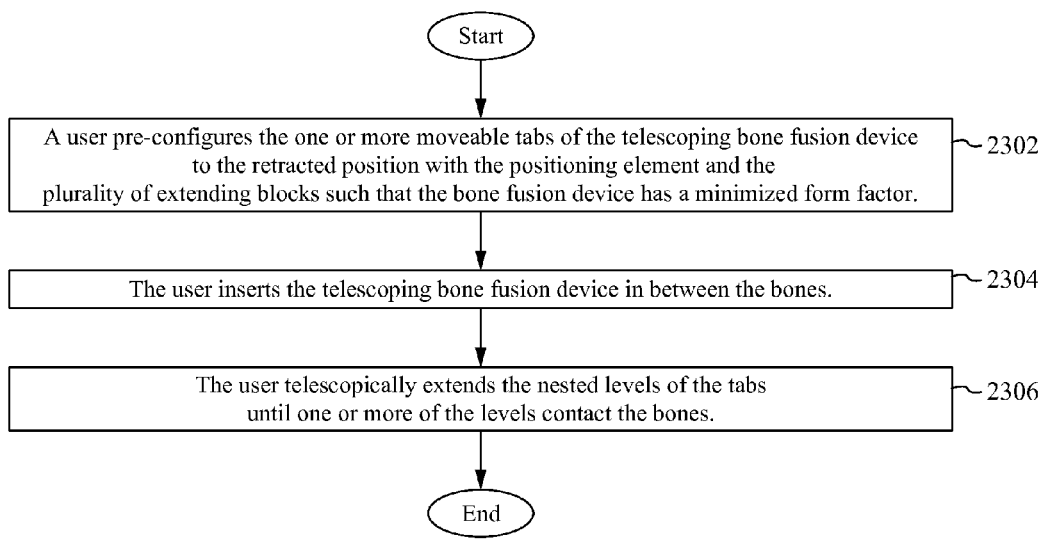
FIG. 23 illustrates a flow chart of a method of implanting a telescoping bone fusion device between bones according to some embodiments.

FIG. 23 illustrates a flow chart of a method of implanting a telescoping bone fusion device between bones according to some embodiments. A user pre-configures the one or more moveable tabs 2204 of the telescoping bone fusion device 2200 to the retracted position with the positioning element 2208 and the plurality of extending blocks 2210 such that the bone fusion device 2200 has a minimized form factor at the step 2302. The user inserts the telescoping bone fusion device 2200 in between the bones at the step 2304. The user telescopically extends the nested levels 2206, 2206' of the tabs 2204 until one or more of the levels 2206, 2206' contact the bones at the step 2306. In some embodiments, each of the nested levels 2206, 2206' of each tab 2204 has a maximum extended position that is different than the maximum extended position of the other nested levels 2206, 2206' of the tabs 2204. In some embodiments, the distance from the body of the maximum extended position for each of the nested levels 2206, 2206' of each tab 2204 increases from the outermost nested level 2206 to the innermost nested level 2206'. In some embodiments, the telescopically extending comprises moving one or more extending blocks 2210 with a positioning element 2208 such that the extending blocks 2210 push against the inner surface profile 2212, 2212' of one or more of the nested tab levels 2206, 2206'. In some embodiments, the innermost nested level 2206' of each tab 2204 comprises one or more tongues 2216 that extend from the top surface of the innermost nested level 2206' to the perimeter of the tab 2204. In some embodiments, the non-innermost nested levels 2206 of each tab 2204 comprise one or more recesses 2214 that align with the one or more tongues 2216 such that when the innermost nested level 2206' is nested within one or more of the non-innermost nested levels 2206 the tongues 2216 slide within the recesses 2214. As a result, the method is able to provide the benefits of a minimally invasive surgery due to the minimized form factor of the telescoping bone fusion device in the retracted position and a more stable bone fusion device with increased extension due to the telescoping and intermediate extensions of the nested tab levels.

Figure 24:
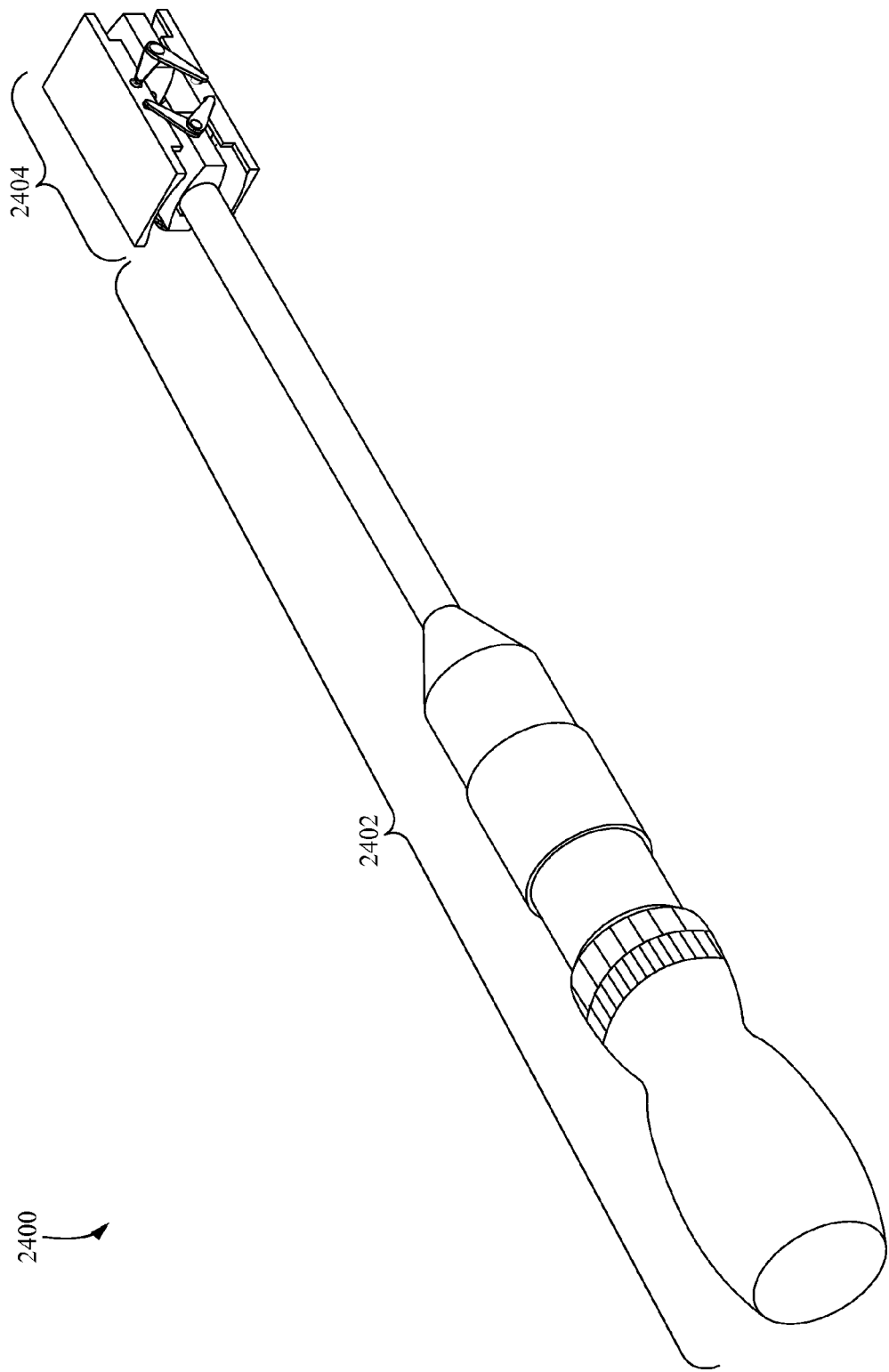
FIG. 24 illustrates a perspective view of a distraction instrument for measuring the space to be filled by a bone fusion device according to some embodiments.
Figure 25:
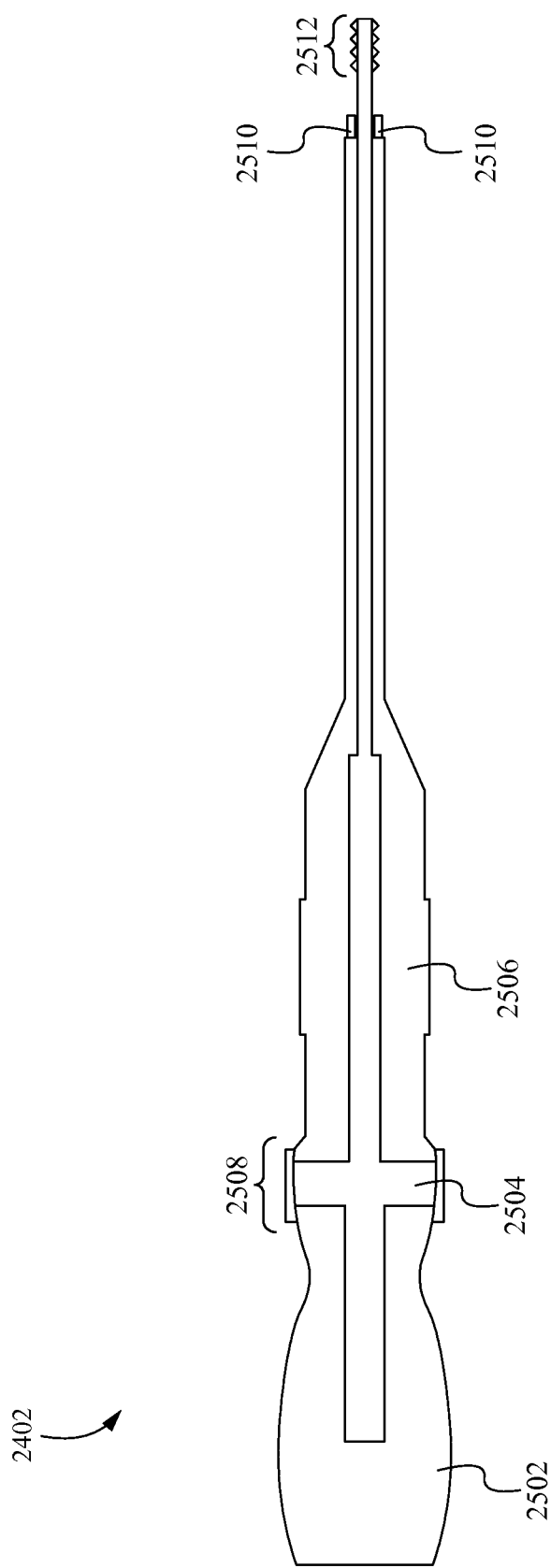
FIG. 25 illustrates a top cross sectional view of the distraction body according to some embodiments.

FIG. 24 illustrates a perspective view of a distraction instrument 2400 for measuring the space to be filled by a bone fusion device according to some embodiments. As shown in FIG. 24, the distraction instrument 2400 comprises a distraction body 2402 and a distraction head 2402 operably coupled together. FIG. 25 illustrates a top cross sectional view of the distraction body 2402 according to some embodiments. As shown in FIG. 25, the distraction body 2402 comprises a handle 2502, a engaging element 2504 and a guide element 2506. The handle 2502 is coupled with the engaging element 2504 which is positioned within the guide element 2506 such that a user is able to rotate, push and/or pull the handle 2502 in order to rotate, extend and/or retract the engaging element 2504 within or further out of the guide element 2506. In some embodiments, the handle 2502 and/or guide element 2506 comprise one or more gripping ridges enabling a user to rotate or otherwise move the handle 2502 with respect to the guide element 2506 without slipping. In some embodiments, the instrument 2400 is able to comprise an electric motor and control interface (not shown) such that the movement of the handle 2502 is able to be effectuated by a user controlling the operation of the electric motor via the control interface. In some embodiments, the guide element 2506 comprises one or more a stop pins 2510 that couple to the stop apertures 2617 of the rear fitting 2614 of the rear jack assembly 2604 (see FIG. 26). When coupled within the stop apertures 2617, the stop pins 2510 are able to prevent the distraction head 2402 from rotating with the engaging element 2504 as well as keeping the rear fitting 2614 of the rear jack assembly 2604 abut the end of the guide element 2506. In some embodiments, the engaging element 2504 comprises a threaded portion 2512 positioned along the end of the engaging element 2504 such that the threaded portion 2512 is able to operably coupling with the threads 2618 of the front fitting 2615 of the front jack assembly 2606 (see FIG. 26). As a result, when the engaging element 2504 is rotated, the threaded portion 2512 is able to engage the threads 2618 of the front fitting 2615 causing the front fitting 2615 to slide toward or away from the rear fitting 2614. Alternatively, the threaded portion 2512 and the threads 2618 are able to be omitted and the end of the engaging element 2504 is able to be coupled to the front fitting 2615 such that when the engaging element 2504 is pulled into or pushed out of the guide element 2506 the coupling causes the front fitting 2615 to also slide toward or away from the rear fitting 2614. Alternatively, the threaded portion 2512 is a female thread such that when the engaging element 2504 is rotated, the threading 2512 causes the engaging element 2504 to retract into the guide element 2506 and the front fitting 2615 to slide toward the rear fitting 2614. In such embodiments, the threading 2512 is able to be positioned in other places along the engaging element 2504.

Figure 26:
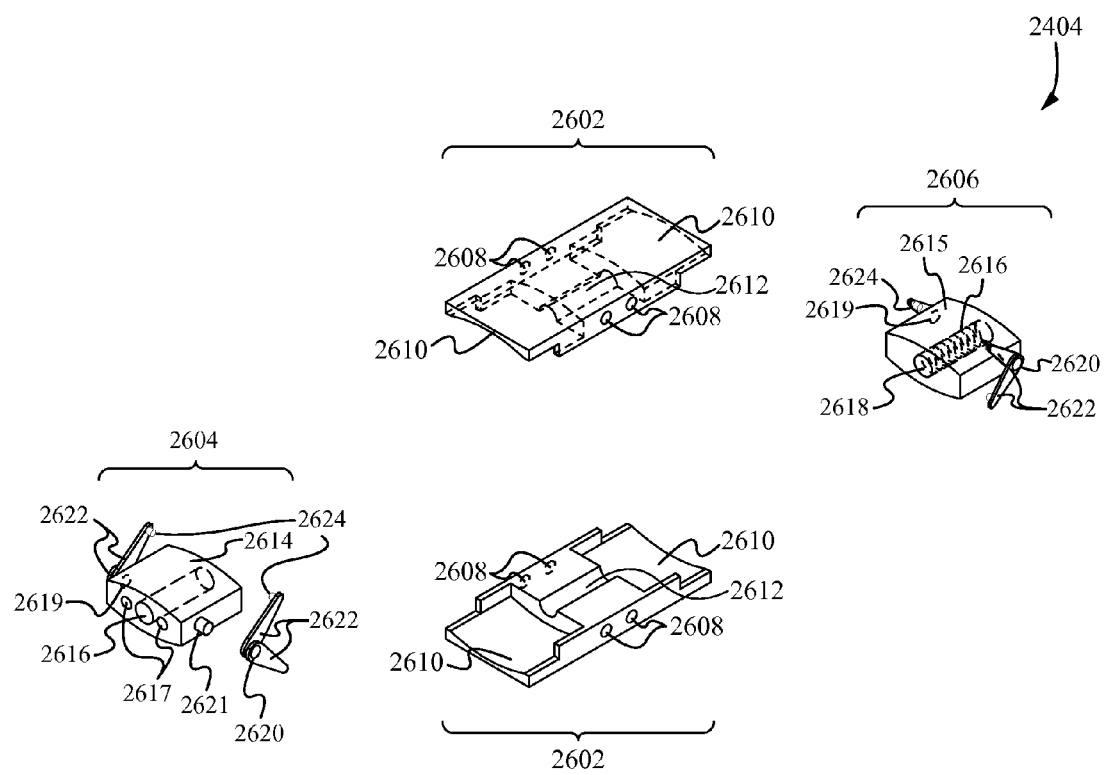
FIG. 26 illustrates a perspective view of the components of the retraction head of the retraction instrument according to some embodiments.

In some embodiments, one or more of the handle 2502, engaging element 2504 and/or the guide element 2506 comprise one or more indicators 2508 that indicate values corresponding to the current separation between the plates 2602 of the head 2404 (see FIG. 26). In some embodiments, the indicators 2508 comprise first markings on the visually exposed surface of the engaging element 2504 and/or handle 2502 that move relative to corresponding second markings on the guide element 2502 when the engaging element 2504 is rotated or otherwise moved. As a result, based on the alignment of the first and second markings the current separation between the plates 2602 of the head 2404 is able to be determined. Alternatively, the indicators 2508 are able to comprise a digital or analog readout/display that indicates the current level of distraction of the instrument 2400. In some embodiments, the motion of the handle 2502 is effectuated by an electrical motor and the indicators 2508 are able to include the control interface for controlling the operation of the electrical motor. Alternatively, other types of indicating elements 2508 corresponding to the current separation of the plates 2602 are able to be used as are well known in the art.

In some embodiments, the indicators 2508 indicate a number of revolutions or rotations that the positioning element of a bone fusion device will require in order to extend the tabs to the height indicated by the separation of the plates 2602. For example, in some embodiments the a user is able to input or the instrument 2400 is able to be pre-programmed with the type of bone fusion device to be used and based on this data, the indicators 2508 are able to indicate the number of rotations/revolutions that the positioning element of a bone fusion device will require in order to extend the tabs to the height indicated by the separation of the plates 2602. In some embodiments, based on the determined current separation of the plates 2602, the indicators 2508 are able to indicate a recommended size and/or type of bone fusion device to be used for filling the measured space. As a result, the distraction instrument 2400 provides the advantage of indicating the best type/size of bone fusion device to use and/or the exact amount of rotation needed to a user of a bone fusion device such that the user does not overextend the tabs of the bone fusion device.

In some embodiments, the instrument 2400 comprises a force measurement component (not shown) and/or the indicators 2508 indicate the amount of force on the plates 2602 that is resisting the expansion/distraction of the plates 2602. In such embodiments, the distraction instrument 2400 is able to be configured to prevent the user from further extending/distracting the plates 2602 when a predefined and/or adjustable force threshold value is detected by the force measurement component. For example, if the distraction is effectuated by an electronically controlled motor the distraction system is able to be configured to automatically stop when the force threshold value is detected. Alternatively, the force measurement component is able to be implemented mechanically such that the components of the instrument 2400 that effectuate the distraction of the plates 2602 prevent further distraction when a predetermined and/or adjustable amount of resistance is present. As a result, the distraction instrument 2400 provides the benefit of enabling a user to manually stop, automatically stopping and/or preventing the user for continuing to distract the plates 2602 when the force measurement component and/or indicators 2508 indicate that a predetermined amount of expansion resistant force is detected on the plates 2602. Thus, the distraction instrument 2400 prevents over distraction that which results in inaccurate measurements and possible injury.

FIG. 26 illustrates a perspective view of the components of the retraction head 2404 of the retraction instrument 2400 according to some embodiments. As shown in FIG. 26, the retraction head 2404 comprises a pair of retraction plates 2602 coupled together by a rear jack assembly 2604 and a front jack assembly 2606. The rear and front jack assemblies 2604, 2605 each comprise a rear/front fitting 2614, 2615 having a fitting conduit 2616 and coupled to a plurality of legs 2622 via one or more fitting pins 2620. Specifically, the plurality of legs 2622 each have a leg pin 2624 and a leg aperture 2619, wherein the leg apertures 2619 are configured to slide onto a pair of fitting protrusions 2621 such that the legs 2622 are able to pivot/rotate about the fitting protrusions 2621 and are prevented from sliding off the protrusions 2621 by the fitting pins 2620. As shown in FIG. 26, two fitting protrusions are each rotatably coupled to a pair of legs 2622. Alternatively, more of less fitting protrusions 2621 are able to be rotatably coupled to more or less legs 2622. Alternatively, the protrusions 2621 and/or fitting pins 2620 are able to be omitted and the legs 2622 are able to be rotatably coupled to the fittings 2614, 2615 via other coupling mechanisms as are well known in the art.

In some embodiments, the conduit 2616 of the rear fitting 2614 is bare whereas the conduit 2616 of the front fitting 2615 has an inner threading 2618 that is operably coupled to the threaded portion 2512 of the engaging element 2504 when the engaging element 2504 is positioned within the conduits 2616 of the retraction head 2404. As a result, the engaging element 2504 is able to freely move independent of the rear fitting 2614, but causes the front fitting 2615 to move toward or away from the rear fitting 2614 along the engaging element 2504 when rotated. Alternatively, the threading 2618 of the conduit 2616 of the front fitting 2615 is able to be omitted and the engaging element 2504 is able to be otherwise coupled to the front fitting 2615 such that when the engaging element 2504 is pulled into or pushed out of the guide element 2506 the coupling causes the front fitting 2615 to correspondingly slide toward or away from the rear fitting 2614. In some embodiments, the rear fitting 2614 comprises one or more stop apertures 2617 that couple with the stop pins 2510 in order to prevent the distraction head 2402 from rotating with the engaging element 2504 and to keep the rear fitting 2614 of the rear jack assembly 2604 in contact with the end of the guide element 2506. Alternatively, the stop pins 2510 and stop apertures 2617 are able to be omitted and the rear fitting 2614 is able to be coupled to the guide element 2506 via other coupling mechanisms as are well known in the art.

The retraction plates 2602 each comprise one or more leg pin apertures 2608, a pair of fitting cavities 2610 and a plate channel 2612. The leg pin apertures 2608 are configured to rotationally couple to the leg pins 2624 such that the plates 2602 are coupled together via the front and rear jack assemblies 2604, 2606. Specifically, when the legs 2622 are caused to rotate about the protrusions 2621 (due to movement of the engaging element 2504), the legs 2622 also rotate within the leg pin apertures 2608 about the leg pins 2624 causing the plates 2602 to selectively move apart or come together. When the plates 2602 are positioned together the fitting cavities 2610 and plate channels 2612 of the upper plate 2602 align with the fitting cavities 2610 and plate channel 2612 of the lower plate 2602. As a result, the height of the retraction head 2404 in the retracted position is minimized because the rear and front fittings 2614, 2615 are able to fit within the aligned fitting cavities 2610 and the engaging element 2612 is able to fit within the aligned plate channels 2612. This provides the advantage of minimizing the size of the required surgical incision for the bone fusion surgery measurement operation.

Figure 27A:
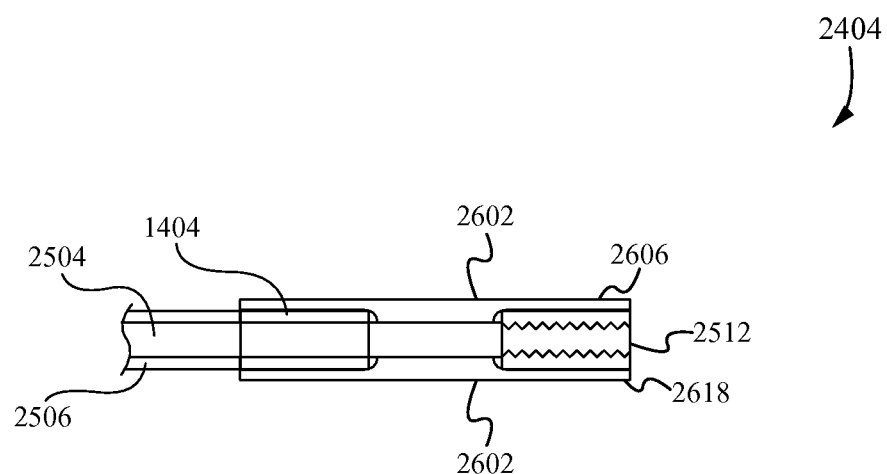
FIG. 27A illustrates cross sectional view of the head of the retraction instrument with the plates fully retracted according to some embodiments.
Figure 27B:
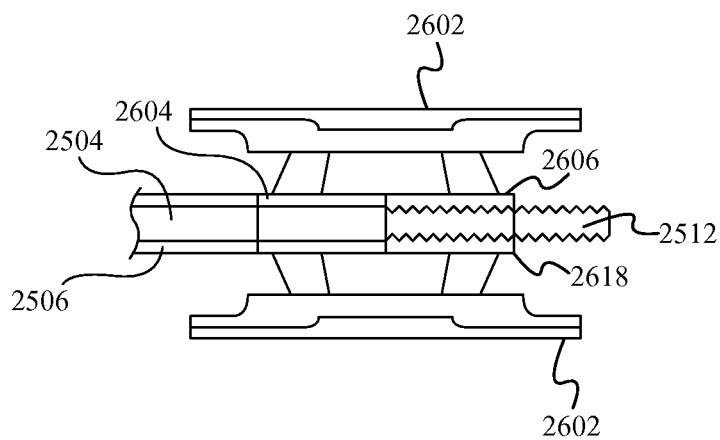
FIG. 27B illustrates cross sectional view of the head of the retraction instrument with the plates fully extended according to some embodiments.

FIGS. 27A and 27B illustrate cross sectional view of the head 2404 of the retraction instrument 2400 with the plates 2602 fully retracted and fully extended, respectively, according to some embodiments. As shown in FIG. 27A, when the retraction instrument 2400 is in the retracted position, the plates 2602 are in contact such that the fittings 2614, 2615 are all or partially housed within/between the plates 2602. While in this position, the retraction instrument 2400 creates the smallest profile possible and thus is able to be surgically inserted between two vertebrae of a patient with a minimally invasive procedure. As shown in FIG. 27B, once in position, the user is able to rotate or otherwise move the engaging element 2504 within the guide element 2506 and head 2404 by manipulating the handle 2502. This manipulation causes the front fitting 2615 to selectively move closer to the rear fitting 2614 and correspondingly the plates 2602 to move away from each other until the desired measurement has been made or the maximum height has been reached due to the front fitting 2615 contacting the rear fitting 2614 along the engaging element 2504. The, user is then able to retract the plates 2602 back together for removal using the opposite rotation and/or opposite other movement of the engaging element 2504 via the handle 2502. Accordingly, the retraction instrument 2400 provides the advantage of a minimized retracted profile that enables a surgeon to measure the size of the space needed to be filled by a bone fusion device or other device while minimizing the surgical incision required to take the measurement.

Figure 28:
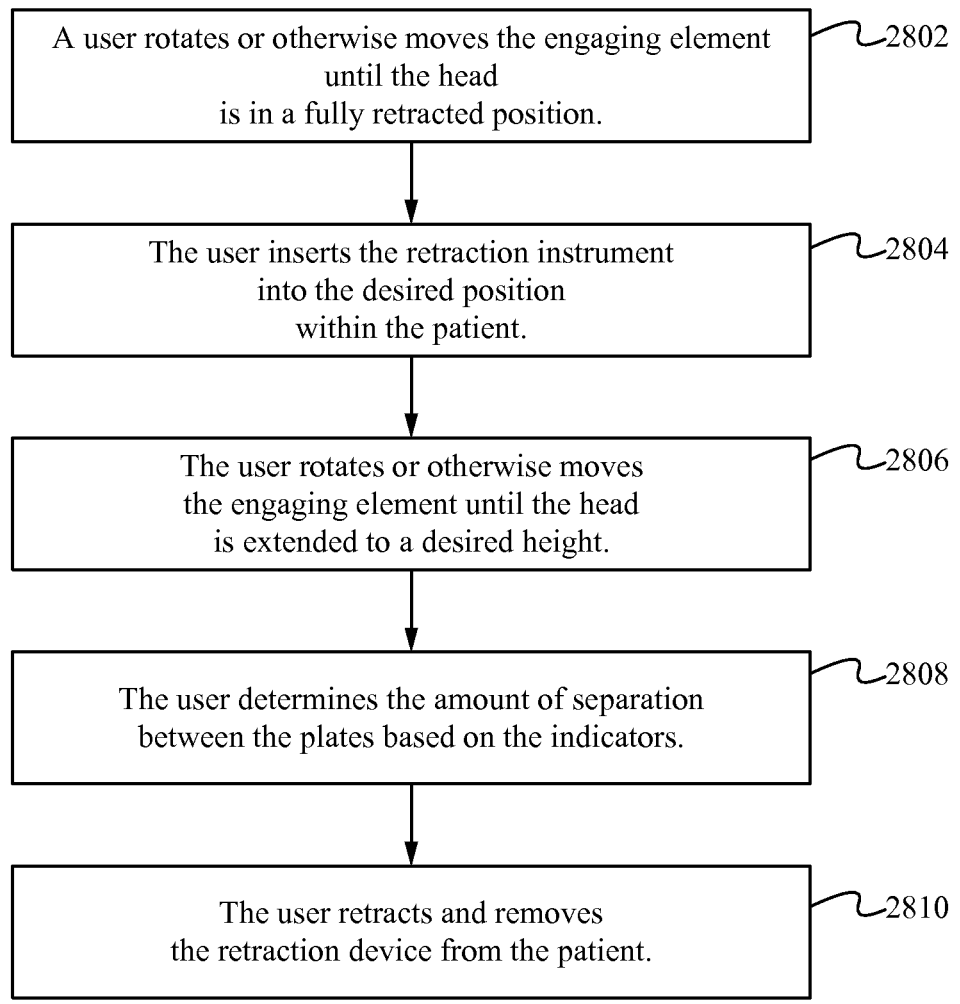
FIG. 28 illustrates a flow chart of a method of operating the retraction instrument according to some embodiments.

FIG. 28 illustrates a flow chart of a method of operating the retraction instrument 2400 according to some embodiments. A user rotates or otherwise moves the engaging element 2504 until the head 2404 is in a fully retracted position at the step 2802. The user inserts the retraction instrument 2400 into the desired position within the patient at the step 2804. In some embodiments, the desired position comprises between or adjacent to one or more vertebrae. In some embodiments, the retraction instrument 2400 is inserted anteriorly. Alternatively, the retraction instrument 2400 is able to be inserted posteriorly, lateral, far-lateral or transforaminaly. The user rotates or otherwise moves the engaging element 2504 until the head 2404 is extended to a desired height at the step 2806. In some embodiments, the desired height comprises the height required such that the lower and upper plates 2602 abut the vertebrae. The indicators 2508 indicate the amount of separation between the plates 2602 at the step 2808. In some embodiments, the indicators 2508 indicate a type and/or size of bone fusion device to utilize to fill the measured space. In some embodiments, the indicators 2508 indicate a number of rotations/revolutions that the positioning element of a bone fusion device will require in order to extend the tabs to the height indicated by the amount of separation of the plates 2602. In some embodiments, the indicators 2508 indicate the current amount of expansion resisting force on the plates 2602. In some embodiments, the desired height comprises the height or separation of the lower and upper plates 2602 when the indicators 2508 indicate the plates 2602 are experiencing a predetermined expansion resisting force threshold value. The user retracts and removes the retraction device 2400 from the patient at the step 2810. In some embodiments, the user then inserts the a bone fusion device into the desired position and extends the tabs such that the bone fusion device fills the indicated height. In some embodiments, the user extends the tabs such that the bone fusion device fills the indicated height by rotating the positioning element of the bone fusion device a number of times indicated by the indicators 2508. In some embodiments, the bone fusion device inserted was selected based on size and/or type of bone fusion device indicated by the indicators 2508. Therefore, the retraction instrument 2400 provides the advantage of determining the size of the space within the patient while only requiring a small incision and minimally invasive (arthroscopic) surgical procedure which advantageously promotes health and rapid recovery by the patient. Further, by determining the size of the space to be filled, the instrument 2400 provides the advantage of enabling the user to select a bone fusion device of the appropriate size to fit within the space and enables the user to pre-configure the tabs of the bone fusion device to near the height required to fill the space such that minimal extension of the tabs is required when the device is in place within the patient.

The bone fusion device, system and method described herein has numerous advantages. Specifically, the RFID chips provide the advantage of enabling identifying and other data to be retrieved from the chips. The stops provide the advantage of preventing the tabs and/or nested levels of the tabs from falling or extending too far out of the body of the device. The retention springs provide the advantage of biasing the tabs in the retracted position such that they do not get stuck or otherwise not properly retract when the extending blocks are moved to the retracted position. The nested tab levels provide the advantage of providing increased lateral support to the tab as it is extended as well as enabling increased stable extension while still minimizing the form factor of the device in the retracted position. The tongues provide the advantage of maintaining an increased surface area of the innermost tab level for increased contact with the bones as well as enabling the inner surface profiles of the tab levels to be simplified as the raising of the outer tabs also raises the inner tabs due to the tongues. Moreover, as mentioned above, the small incision and minimally invasive (arthroscopic) surgical procedure advantageously promote health and rapid recovery by the patient. Preferably, bone growth occurs around the bone fusion device and particularly at the locations of the extended tabs, such that the bone fusion device is further secured by the bone growth, which further promotes a superior, robust bone fusion result.

The present invention has been described in terms of specific embodiments incorporating details to facilitate the understanding of principles of construction and operation of the invention. Such reference herein to specific embodiments and details thereof is not intended to limit the scope of the claims appended hereto. It will be apparent to those skilled in the art that modification may be made in the embodiments chosen for illustration without departing from the spirit and scope of the invention.

What is claimed is:

1. A bone fusion device for insertion into a desired location, comprising:
   a. a body having a first end, an interior cavity and an inner surface having one or more recesses;
   b. one or more tabs each having one or more stops protruding from a perimeter of the tabs, wherein the tabs are configured to selectively move from a retracted position within the body to an extended position extending out of the body in order to brace the bone fusion device in the desired location;
   c. a positioning element positioned through the first end of the body and substantially within the interior cavity of the body; and
   d. one or more extending blocks coupled to the positioning element for moving the one or more tabs between the retracted position and the extended position;
   wherein the recesses are configured to receive the stops when the tabs are inserted into the body and to prevent the tabs from separating from the body by blocking the outward movement of the stops when the tabs are in the extended position.

2. The device of claim 1, wherein the bottom of the outward surface of each of the stops is closer to the perimeter of the tabs than the top of the outward surface of each of the stops such that each the stop comprises an angled outward face with respect to the perimeter of the tabs in order to facilitate the insertion of the stops into the recesses of the body.

3. The device of claim 2, wherein a top portion of each of the stops is separated from the perimeter of the tabs such that the top portion is able to flex toward the perimeter of the tabs in order to facilitate the insertion of the stops into the recesses of the body.

4. The device of claim 3, further comprising one or more retention springs configured to apply a force to the stops of the tabs thereby biasing the tabs in the retracted position.

5. The device of claim 4, wherein the retention springs comprise one or more wires coupled to the body and positioned such that the wires impede the stops of the tabs from moving to the extended position thereby biasing the tabs in the retracted position.

6. The device of claim 4, wherein the retention springs comprise one or more wires coupled to the body and the stops of the tabs such that the wires resist movement of the tabs with respect to the body thereby biasing the tabs in the retracted position.

7. The device of claim 4, wherein the retention springs comprise one or more wires each coupled to the stops of two or more of the tabs such that the wires resist separation of the two or more tabs thereby biasing the tabs in the retracted position.

8. The device of claim 4, wherein the retention springs comprise one or more flexible portions of the body positioned such that the flexible portions of the body impede the stops of the tabs from moving within the recesses when the tabs are moving toward the extended position thereby biasing the tabs in the retracted position.

* * * * *